United States Patent
Kastelein et al.

(10) Patent No.: US 12,018,085 B2
(45) Date of Patent: Jun. 25, 2024

(54) INTERFERON-GAMMA R2 (IFNGR2) BINDING MOLECULES COMPRISING SINGLE-DOMAIN ANTIBODIES AND METHOD OF USE THEREOF TO TREAT AUTOIMMUNE AND INFLAMMATORY DISEASES

(71) Applicant: Synthekine, Inc., Menlo Park, CA (US)

(72) Inventors: Robert Kastelein, Menlo Park, CA (US); Patrick J. Lupardus, Menlo Park, CA (US); Deepti Rokkam, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 0 days.

(21) Appl. No.: 18/019,001

(22) PCT Filed: Aug. 5, 2021

(86) PCT No.: PCT/US2021/044610
§ 371 (c)(1),
(2) Date: Jan. 31, 2023

(87) PCT Pub. No.: WO2022/031890
PCT Pub. Date: Feb. 10, 2022

(65) Prior Publication Data
US 2023/0279128 A1 Sep. 7, 2023

Related U.S. Application Data

(60) Provisional application No. 63/135,884, filed on Jan. 11, 2021, provisional application No. 63/078,745, filed on Sep. 15, 2020, provisional application No. 63/061,562, filed on Aug. 5, 2020.

(51) Int. Cl.
| | |
|---|---|
| *C07K 16/28* | (2006.01) |
| *A61P 37/02* | (2006.01) |
| *C07K 14/715* | (2006.01) |
| *C07K 16/46* | (2006.01) |
| *C12N 15/63* | (2006.01) |
| *C12N 15/86* | (2006.01) |
| *A61K 39/00* | (2006.01) |

(52) U.S. Cl.
CPC .......... *C07K 16/2866* (2013.01); *A61P 37/02* (2018.01); *C07K 14/7155* (2013.01); *C07K 16/2803* (2013.01); *C07K 16/46* (2013.01); *C07K 16/468* (2013.01); *C12N 15/63* (2013.01); *C12N 15/86* (2013.01); *A61K 2039/505* (2013.01); *C07K 2317/22* (2013.01); *C07K 2317/24* (2013.01); *C07K 2317/31* (2013.01); *C07K 2317/33* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/567* (2013.01); *C07K 2317/569* (2013.01)

(58) Field of Classification Search
CPC .......... C07K 16/2866; C07K 2317/565; C07K 2317/567; C07K 2317/569; C12N 15/86
See application file for complete search history.

(56) References Cited

U.S. PATENT DOCUMENTS

| | | |
|---|---|---|
| 8,258,268 B2 | 9/2012 | Wu et al. |
| 8,921,528 B2 | 12/2014 | Holt et al. |
| 8,975,382 B2 | 3/2015 | Revets et al. |
| 9,334,331 B2 | 5/2016 | Igawa et al. |
| 10,421,807 B2 | 9/2019 | Gonzales et al. |
| 10,927,186 B2 | 2/2021 | Roobrouck et al. |
| 2006/0002935 A1 | 1/2006 | Brewis et al. |
| 2006/0024295 A1 | 2/2006 | Brunetta |
| 2009/0220511 A1 | 9/2009 | Kotenko et al. |
| 2010/0297127 A1 | 11/2010 | Ghilardi et al. |
| 2011/0028695 A1 | 2/2011 | Revets et al. |
| 2011/0053865 A1 | 3/2011 | Saunders et al. |
| 2011/0142831 A1 | 6/2011 | Cua et al. |
| 2011/0177081 A1 | 7/2011 | Thiry et al. |
| 2011/0250213 A1 | 10/2011 | Tso et al. |
| 2012/0201746 A1 | 8/2012 | Liu et al. |
| 2012/0225081 A1 | 9/2012 | Gschwind et al. |
| 2012/0316324 A1 | 12/2012 | Adams et al. |
| 2013/0189262 A1 | 7/2013 | Wong et al. |
| 2014/0065142 A1 | 3/2014 | Roschke et al. |
| 2014/0099708 A1 | 4/2014 | Carballido Herrera et al. |
| 2014/0154256 A1 | 6/2014 | Wu et al. |
| 2014/0170154 A1 | 6/2014 | Presta |
| 2014/0302038 A1 | 10/2014 | Dimasi et al. |

(Continued)

FOREIGN PATENT DOCUMENTS

| | | |
|---|---|---|
| CN | 103396482 A | 11/2013 |
| CN | 111018985 A | 6/2019 |

(Continued)

OTHER PUBLICATIONS https://www.biocompare.com/pfu/110447/soids/22483/Antibodies/IFNGR2 (retrieved from the internet Jul. 10, 2023).*
https://www.ncbi.nlm.nih.gov/gene/3460 (accessed on the internet Sep. 16, 2023).*
https://www.thermofisher.com/antibody/product/IFNGR2-Antibody-clone-7-Recombinant-Monoclonal/MA5-31154 (accessed on the internet Sep. 17, 2023).*
https://www.abcam.com/products/primary-antibodies/ifn-gamma-receptor-betaaf-1-antibody-epr8813-ab171081.html (accessed on the internet Sep. 17, 2023).*

(Continued)

*Primary Examiner* — Robert S Landsman
(74) *Attorney, Agent, or Firm* — Kilpatrick Townsend & Stockton LLP

(57) ABSTRACT

The present disclosure relates to biologically active molecules comprising a single domain antibody (sdAb) that specifically binds to the extracellular domain of human IFNgR2, compositions comprising such antibodies, and methods of use thereof.

109 Claims, No Drawings
Specification includes a Sequence Listing.

(56) References Cited

U.S. PATENT DOCUMENTS

| | | |
|---|---|---|
| 2015/0079088 A1 | 3/2015 | Lowman et al. |
| 2016/0017387 A1 | 1/2016 | Hsieh et al. |
| 2016/0046730 A1 | 2/2016 | Ghayur et al. |
| 2016/0251440 A1 | 9/2016 | Roobrouck et al. |
| 2017/0106051 A1 | 4/2017 | Oh et al. |
| 2017/0298149 A1 | 10/2017 | Baeuerle et al. |
| 2018/0362655 A1 | 12/2018 | Wang et al. |
| 2018/0362668 A1 | 12/2018 | Xu |
| 2019/0185562 A1 | 6/2019 | Gromada et al. |
| 2019/0315864 A1 | 10/2019 | Xu et al. |
| 2019/0352404 A1 | 11/2019 | Xu et al. |
| 2019/0382500 A1 | 12/2019 | Abujoub et al. |
| 2020/0055912 A1 | 2/2020 | Kley et al. |
| 2020/0071716 A1 | 3/2020 | Raab et al. |
| 2020/0087624 A1 | 3/2020 | Wood et al. |
| 2020/0148772 A1 | 5/2020 | Ting et al. |
| 2020/0157237 A1 | 5/2020 | Regev et al. |
| 2020/0399382 A1 | 12/2020 | Blanchetot et al. |
| 2023/0137672 A1 | 5/2023 | Perna |

FOREIGN PATENT DOCUMENTS

| | | |
|---|---|---|
| CN | 111040035 A | 4/2020 |
| WO | 2008/011081 A2 | 1/2008 |
| WO | 2009/068631 A1 | 6/2009 |
| WO | 2010142551 A2 | 12/2010 |
| WO | 2011051327 A2 | 5/2011 |
| WO | 2011095604 A1 | 8/2011 |
| WO | 2013/006544 A1 | 1/2013 |
| WO | 2013/059299 A1 | 4/2013 |
| WO | 2015142675 A2 | 9/2015 |
| WO | 2016/097313 A1 | 6/2016 |
| WO | 2017/198212 A1 | 11/2017 |
| WO | 2018233624 A1 | 12/2018 |
| WO | 2019/129221 A1 | 7/2019 |
| WO | 2019242632 A1 | 12/2019 |
| WO | 2020052543 A1 | 3/2020 |
| WO | 2020094834 A1 | 5/2020 |
| WO | 2020094836 A1 | 5/2020 |
| WO | 2020/144164 A1 | 7/2020 |
| WO | 2020/187711 A1 | 9/2020 |
| WO | 2022031871 A1 | 2/2022 |
| WO | 2022055641 A2 | 3/2022 |

OTHER PUBLICATIONS https://www.biocompare.com/pfu/110447/soids/22483/Antibodies/IFNGR2 (accessed on the internet Sep. 17, 2023).*

Langer V, et al. (2019) J Clin Invest. 129(11):4691-4707. (https://doi.org/10.1172/JCI124884).*

Lu B, et al. (Jul. 1998) Proc. Natl. Acad. Sci. USA. 95:8233-8238.*

Naves R, et al. (2013) J Immunol. 191(6):2967-2977. (https://doi.org/10.4049/jimmunol.1300419).*

Pollard KM, et al. (Sep. 2013) Discov Med. 16(87):123-131.*

Tosevski V. (2014) Dissertation—The Effects of Interferon Gamma Deficiency on the Autoimmune Inflammation of the Central Nervous System.*

Sosa RA, et al. (published online Aug. 24, 2015) PNAS. E5038-E5047. (www.pnas.org/cgi/doi/10.1073/pnas.1505955112).*

Tichauer JE, et al. (Jun. 2, 2023) Front. Immunol. 14:1191838. 22 pages. (https://doi.org/10.3389/fimmu.2023.1191838).*

Pingwara et al. IFN-λ Modulates the Migratory Capacity of Canine Mammary Tumor Cells via Regulation of the Expression of Matrix Metalloproteinases and Their Inhibitors. Cells. Apr. 23, 2021;10(5):999.

ISA/USA; International Search Report and Written Opinion; PCT/US21/44610, dated Jan. 5, 2022; 11 pgs.

U.S. Appl. No. 18/019,042, filed Aug. 5, 2021, Kastelein et al.

U.S. Appl. No. 18/019,081, filed Jan. 31, 2023, Kastelein et al.

IFNLR1 Interferon Lambda Receptor 1 [*Homo Sapiens* (Human)], National Library of Medicine, Gene ID: 163702, Accessed from Internet on Sep. 12, 2023, 9 pages.

Biolegend, "PE Anti-Mouse IL-23R Antibody", BioLegend, Available Online at: https://biolegend.com/en-us/global-elements/pdf-popup/pe-anti-mouse-il-23r-antibody-13084?filename=PE%20anti-mouse%201L-23R%20Antibody.pdf&pdfoen=true, Mar. 28, 2016, 2 pages.

"UniProtKB—A0A066RQT8", Uncharacterized Protein, Available Online at: https://www.uniprot.org/uniprot/A0A066RQT8, Sep. 3, 2014, 3 pages.

U.S. Appl. No. 18/006,484, Non-Final Office Action, dated Sep. 28, 2023, 12 pages.

Cairo et al., "Control of Multivalent Interactions by Binding Epitope Density", Journal of the American Chemical Society, vol. 124, No. 8, Feb. 2, 2002, pp. 1615-1619.

Crepaldi et al., "Up-Regulation of IL-10R1 Expression is Required to Render Human Neutrophils Fully Responsive to IL-10", The Journal of Immunology, vol. 167, No. 4, Aug. 15, 2001, pp. 2312-2322.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody", Journal of Immunology, vol. 169, No. 6, Sep. 15, 2002, pp. 3076-3084.

De Weerd et al., "The Interferons and Their Receptors—Distribution and Regulation", Immunology & Cell Biology, vol. 90, No. 5, May 2012, pp. 483-491.

Delgoffe et al., "Interpreting Mixed Signals: The Cell's Cytokine Conundrum", Current Opinion in Immunology, vol. 23, No. 5, Oct. 2011, pp. 1-13.

Donnelly et al., "The Expanded Family of Class II Cytokines that Share the IL-10 Receptor-2 (IL-10R2) Chain", Journal of Leukocyte Biology, vol. 76, No. 2, Aug. 2004, pp. 314-321.

Fan et al., "Bispecific Antibodies and their Applications", Journal of Hematology & Oncology, vol. 8, No. 130, Dec. 21, 2015, pp. 1-14.

Franke et al., "Human and Murine Interleukin 23 Receptors are Novel Substrates for a Disintegrin and Metalloproteases ADAM10 and ADAM17", The Journal of Biological Chemistry, vol. 291, No. 20, May 13, 2016, pp. 10551-10561.

Fu et al., "Comparison of Camelus Bactrianus VHH Sequences from Conventional and Heavy Chain Antibodies", National Center for Biotechnology Information, Available Online at: https://www.ncbi.nlm.nih.gov/nucleotide/KF179376.1, GenBank: KF179376.1, Sep. 21, 2013, 1 page.

Goel et al., "Plasticity within the Antigen-Combining Site May Manifest as Molecular Mimicry in the Humoral Immune Response", The Journal of Immunology, vol. 173, No. 12, Dec. 15, 2004, pp. 7358-7367.

Heldin, "Dimerization of Cell Surface Receptors in Signal Transduction", Cell, vol. 80, No. 2, Jan. 27, 1995, pp. 213-223.

Jiang et al., "Regulation of Interleukin-10 Receptor Ubiquitination and Stability by Beta-TrCP-Containing Ubiquitin E3 Ligase", PLoS One, vol. 6, No. 11, Nov. 2011, pp. 1-14.

Khan et al., "Adjustable Locks and Flexible Keys: Plasticity of Epitope-Paratope Interactions in Germline Antibodies", Journal of Immunology, vol. 192, No. 11, Jun. 1, 2014, pp. 5398-5405.

Kontermann, "Dual Targeting Strategies with Bispecific Antibodies", mABs, vol. 4, No. 2, Mar.-Apr. 2012, pp. 182-197.

Lloyd et al., "Modelling the Human Immune Response: Performance of a 1011 Human Antibody Repertoire Against a Broad Panel of Therapeutically Relevant Antigens", Protein Engineering, Design and Selection, vol. 22, No. 3, Mar. 2009, pp. 159-168.

Lo et al., "Conformational Epitope Matching and Prediction Based on Protein Surface Spiral Features", BMC Genomics, vol. 22, May 31, 2021, pp. 1-16.

Lundin et al., "Production and Partial Characterization of Mouse Monoclonal Antibodies Recognizing Common Cytokine Receptor Gamma Chain (γc) of Human, Mouse and Primate Origin", Acta Pathologica, Microbiologica, et Immunologica Scandinavica, vol. 109, No. 10, Oct. 2001, pp. 647-655.

MacCallum et al., "Antibody-Antigen Interactions: Contact Analysis and Binding Site Topography", Journal of Molecular Biology, vol. 262, No. 5, Oct. 11, 1996, pp. 732-745.

(56) References Cited

OTHER PUBLICATIONS

Marks et al., "How Repertoire Data are Changing Antibody Science", Journal of Biological Chemistry, vol. 295, No. 29, Jul. 17, 2020, pp. 9823-9837.
Nie et al., "Biology Drives the Discovery of Bispecific Antibodies as Innovative Therapeutics", Antibody Therapeutics, vol. 3, No. 1, Feb. 17, 2020, pp. 18-62.
Application No. PCT/US2021/044575, International Search Report and Written Opinion, dated Feb. 2, 2022, 14 pages.
Application No. PCT/US2021/044576, International Search Report and Written Opinion, dated Jan. 12, 2022, 12 pages.
Application No. PCT/US2021/044602, International Search Report and Written Opinion, dated Feb. 2, 2022, 13 pages.
Application No. PCT/US2021/044610, International Preliminary Report on Patentability, dated Feb. 16, 2023, 7 pages.
PCT/US2021/044610, "Invitation to Pay Additional Fees and, Where Applicable, Protest Fee", Nov. 4, 2021, 2 pages.
Application No. PCT/US2021/044674, International Search Report and Written Opinion, dated Jan. 19, 2022, 12 pages.
Application No. PCT/US2021/044695, International Search Report and Written Opinion, dated Feb. 2, 2022, 14 pages.
Application No. PCT/US2021/044698, International Search Report and Written Opinion, dated Feb. 1, 2022, 13 pages.
Application No. PCT/US2021/044730, International Preliminary Report on Patentability, dated Feb. 16, 2023, 10 pages.
Application No. PCT/US2021/044730, "Invitation to Pay Additional Fees and, Where Applicable, Protest Fee", Apr. 21, 2022, 4 pages.
Application No. PCT/US2021/044730, International Search Report and Written Opinion, dated Jun. 21, 2022, 16 pages.
Application No. PCT/US2021/044734, International Preliminary Report on Patentability, dated Feb. 16, 2023, 9 pages.
PCT/US2021/044734, "Invitation to Pay Additional Fees and, Where Applicable, Protest Fee", Nov. 16, 2021, 2 pages.
Application No. PCT/US2021/044734, International Search Report and the Written Opinion, dated Feb. 2, 2022, 13 pages.
Application No. PCT/US2021/044802, International Search Report and Written Opinion, dated Feb. 3, 2022, 13 pages.
Application No. PCT/US2021/044803, International Search Report and Written Opinion, dated Jan. 26, 2022, 11 pages.
Application No. PCT/US2021/044834, International Search Report and Written Opinion, dated Feb. 2, 2022, 15 pages.
Application No. PCT/US2021/044835, International Search Report and Written Opinion, dated Feb. 8, 2022, 17 pages.
Application No. PCT/US2021/044837, International Search Report and Written Opinion, dated Dec. 20, 2021, 11 pages.
Application No. PCT/US2021/044837, International Preliminary Report on Patentability, dated Feb. 16, 2023, 8 pages.
Application No. PCT/US2021/044841, International Search Report and Written Opinion, dated Dec. 17, 2021, 10 pages.
Application No. PCT/US2021/044850, International Search Report and Written Opinion, dated Jan. 6, 2022, 9 pages.
Application No. PCT/US2021/044853, International Search Report and Written Opinion, dated Dec. 17, 2021, 10 pages.
Application No. PCT/US2021/044855, International Search Report and Written Opinion, dated Dec. 16, 2021, 11 pages.
Saerens et al., "Single-Domain Antibodies as Building Blocks for Novel Therapeutics", Current Opinion in Pharmacology, vol. 8, No. 5, Oct. 2008, pp. 600-608.
Shahangain et al., "VHH Against VEGF-RBD", GenBank: BAR73350.1, Available Online at: https://www.ncbi.nlm.nih.gov/protein/BAR73350.1, May 12, 2015, 2 pages.
Shouval et al., "Interleukin 10 Receptor Signaling: Master Regulator of Intestinal Mucosal Homeostasis in Mice and Humans", Advances in Immunology, vol. 122, 2014, pp. 1-29.
Watzka et al., "Guided Selection of Antibody Fragments Specific for Human Interferon Gamma Receptor 1 from a Human VH- and VL-Gene Repertoire", Immunotechnology, vol. 3, Issue 4, Jan. 1998, pp. 279-291.
Weidle et al., "The Intriguing Options of Multispecific Antibody Formats for Treatment of Cancer", Cancer Genomics & Proteomics, vol. 10, No. 1, Jan.-Feb. 2013, pp. 1-18.
Wilton et al., "sdAb-DB: The Single Domain Antibody Database", ACS Synthetic Biology, vol. 7, No. 11, Nov. 16, 2018, pp. 2480-2484.
Hoey et al., "Structure and Development of Single Domain Antibodies as Modules for Therapeutics and Diagnostics", Experimental Biology and Medicine, vol. 244, No. 17, Dec. 2019, pp. 1568-1576.

* cited by examiner

INTERFERON-GAMMA R2 (IFNGR2) BINDING MOLECULES COMPRISING SINGLE-DOMAIN ANTIBODIES AND METHOD OF USE THEREOF TO TREAT AUTOIMMUNE AND INFLAMMATORY DISEASES

CROSS-REFERENCES TO RELATED APPLICATIONS

This application is a 371 National Phase Application of PCT/US2021/044610, filed Aug. 5, 2021, which application claims priority to U.S. Provisional Application No. 63/061,562, filed Aug. 5, 2020, U.S. Provisional Application No. 63/078,745, filed Sep. 15, 2020, and U.S. Provisional Application No. 63/135,884, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Aug. 31, 2021, is named 106249-1258372_SL.txt and is 99,045 bytes in size.

FIELD OF THE INVENTION

The present disclosure relates to biologically active molecules comprising a single domain antibody that specifically binds to the extracellular domain of the Interferon-γ R2 (IFNgR2), compositions comprising such single domain antibodies, and methods of use thereof.

BACKGROUND

Interferon gamma is homodimer of two 17 kDa subunits. The IFN-γ receptor is tetramer comprising two ligand-binding IFNγR1 subunits which associated two signal-transducing IFNγR2 subunits. IFN-γ binding results in the oligomerization of the intracellular domains of IFNγR2 and activation of intracellular signaling vi JAK1 and JAK2. Phosphorylation of the intracellular domain of the IFNγR2 creates binding sites for STAT1 which is in turn phosphorylated which dimerize and translocate to the nucleus. The IFNγ signaling pathway results in a variety of biological responses primarily associated with host defense and immune surveillance. IFNγ results upregulation of the major histocompatibility complex (MHC) molecules as well as the upregulation MHC I and II antigen processing and presentation machinery.

IFN-γ is a major product of Th1-mediated immune response. Upregulation of cell surface MHC class I by IFN-γ is an essential element in the response to intracellular pathogens and tumor cells. IFN-γ acts as a cytotoxic CD8 T cell differentiation signal and is essential for CD8T cell proliferation. IFN-γ also upregulates cell surface MHC class II on antigen presenting cells and activation of CD4 T cells and activates. The central role of IFN-γ in the immune response can be illustrated by its involvement in more 290 genes related to cytokine and chemokine receptors, cell activation markers, cellular adhesion proteins, MHC proteins, proteasome formation, protein turnover, and signaling mediators and regulators.

As a result of the central role of IFNγ in the immune response, inhibition of IFNγ is associated with significant downregulation of immunity and morbidity. IFNγR1 deficiency is a life-threatening autosomal recessive immune disorder and affected children frequently die of infection in the absence of bone marrow transplantation. Affected children invariably die of mycobacterial infection, unless bone marrow transplantation is undertaken. Even then, survivors are susceptible to severe infection from environmental factors.

Although monoclonal antibodies are the most widely used reagents for the detection and quantification of proteins, monoclonal antibodies are large molecules of about 150 kDa and it sometimes limits their use in assays with several reagents competing for close epitopes recognition. A unique class of immunoglobulin containing a heavy chain domain and lacking a light chain domain (commonly referred to as heavy chain" antibodies (HCAbs) is present in camelids, including dromedary camels, Bactrian camels, wild Bactrian camels, llamas, alpacas, vicuñas, and guanacos as well as cartilaginous fishes such as sharks. The isolated variable domain region of HCAbs is known as a VHH (an abbreviation for "variable-heavy-heavy" reflecting their architecture) or Nanobody® (Ablynx). Single domain VHH antibodies possesses the advantage of small size (~12-14 kD), approximately one-tenth the molecular weight a conventional mammalian IgG class antibody) which facilitates the binding of these VHH molecules to antigenic determinants of the target which may be inaccessible to a conventional monoclonal IgG format (Ingram et al., 2018). Furthermore, VHH single domain antibodies are frequently characterized by high thermal stability facilitating pharmaceutical distribution to geographic areas where maintenance of the cold chain is difficult or impossible. These properties, particularly in combination with simple phage display discovery methods that do not require heavy/light chain pairing (as is the case with IgG antibodies) and simple manufacture (e.g., in bacterial expression systems) make VHH single domain antibodies useful in a variety of applications including the development of imaging and therapeutic agents.

SUMMARY OF THE INVENTION

The present disclosure provides polypeptides that specifically bind to the extracellular domain of IFNgR2.

The present disclosure provides a IFNgR2 binding molecule that specifically bind to the extracellular domain of IFNgR2 (e.g., human IFNgR2).

In some embodiments, the IFNgR2 binding molecule comprises a single domain antibody (sdAb) that specifically binds to the extracellular domain of the human IFNgR2.

In some embodiments, the IFNgR2 binding molecule is a sdAb, the sdAb comprising a set of CDRs corresponding to CDR1, CDR2, and CDR3 as shown in a row of Table 1 below.

In some embodiments, the IFNgR2 binding molecule comprises a CDR1, a CDR2, and a CDR3 as described in a row of Table 1 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 below.

In some embodiments, the IFNgR2 binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 100% identity to a polypeptide sequence of any one of SEQ ID NOS: 2-33, as shown in Table 1 below.

TABLE 1

| Name | Sequence (CDRs underlined) | CDR1 | CDR2 | CDR3 |
|------|---------------------------|------|------|------|
| DR927 | QVQLVESGGGLVQAGGSLRLSCAASGRTFTSYAMNWFRQAPGKEREFVAAISWSSGNTYVADSVKGRFAISRDKAKNTMYLQMNSLAPEDTAVYYCAATTIATMSDEYTYWGQGTQVTVSS (SEQ ID NO: 2) | RTFTSYAMN (SEQ ID NO: 34) | AISWSSGNTYVADSVKG (SEQ ID NO: 35) | TTIATMSDEYTY (SEQ ID NO: 36) |
| DR928 | QVQLVESGGGLVQAGGSLRLSCAASGRTFSNYRMGWFRQAPGKEREFVAAISRGGGTTLYADSVKGRFTISRDNAKNTVDLQMNRLKPEDTAVYFCAAGDFSTTWDEYNYWGQGTQVTVSS (SEQ ID NO: 3) | RTFSNYRMG (SEQ ID NO: 37) | AISRGGGTTLYADSVKG (SEQ ID NO: 38) | GDFSTTWDEYNY (SEQ ID NO: 39) |
| DR929 | QVQLVESGGGLVQAGGSLRLSCVASGRTFSSYAMGWFRQTPGKEREFVSAISRGGGSTDYADSVKGRFTISRDNAKNTVYLQMNNLKSEDTAVYYCALRAYSGRYYQFLEYDYWGQGTQVTVSS (SEQ ID NO: 4) | RTFSSYAMG (SEQ ID NO: 40) | AISRGGGSTDYADSVKG (SEQ ID NO: 41) | RAYSGRYYQFLEYDY (SEQ ID NO: 42) |
| DR930 | EVQLVESGGGLVQAGGSLRLSCTVSGRTFSSYAVAWFRQAPGNVRELAAALSRGGGSAYYTDSVKGRFTISRDNAKNTVYLQMNSLKPEDTAVYYCAARNYDGTYYQENQYNYWGQGTQVTVSS (SEQ ID NO: 5) | RTFSSYAVA (SEQ ID NO: 43) | ALSRGGGSAYYTDSVKG (SEQ ID NO: 44) | RNYDGTYYQENQYNY (SEQ ID NO: 45) |
| DR931 | QVQLVESGGGLVQAGGSLLLSCAASGRTFSTYAMGWFRQAPGKERMFVAAISVNGGSTYYADSVTGRFTISRDNAKNTMYLQMNNLKPGDTAVYYCAARRPYPGSDFLTWASYDYRGQGTLVTVSS (SEQ ID NO: 6) | RTFSTYAMG (SEQ ID NO: 46) | AISVNGGSTYYADSVTG (SEQ ID NO: 47) | RRPYPGSDFLTWASYDY (SEQ ID NO: 48) |
| DR932 | QVQLVESGGGLVQAGGFLRLSCAASGRTFSYTTIGWFRQAPGKEREFVAVISAGGGSRDYADALKGRFTISRDNAKKMVYLQMNNLKPEDTAVYYCAVRRNTDTYTTTGDYDYWGQGTQVTVSS (SEQ ID NO: 7) | RTFSYTTIG (SEQ ID NO: 49) | VISAGGGSRDYADALKG (SEQ ID NO: 50) | RRNTDTYTTTGDYDY (SEQ ID NO: 51) |
| DR933 | QVQLVESGGGLVQPGDSLRLSCVASGGTISSLAMGWFRQAPGKEREFVAAISWSGRSTYYVDSVKGRFTISTDNAKNTVYLQMNSLKPEDTAVYYCVAGEDGHSEYDYWGQGTQVTVSS (SEQ ID NO: 8) | GTISSLAMG (SEQ ID NO: 52) | AISWSGRSTYYVDSVKG (SEQ ID NO: 53) | GEDGHSEYDY (SEQ ID NO: 54) |
| DR934 | QVQLVESGGGLVQAGGSLRLSCAASGRSFANYAMGWFRQAPGKERETVAAISRGGGSTWYADSVKGRFTISKDNAKNTVYLQMNSLKPEDTAIYYCAARSYGSYTYSFGEYDYWGQGTQVTVSS (SEQ ID NO: 9) | RSFANYAMG (SEQ ID NO: 55) | AISRGGGSTWYADSVKG (SEQ ID NO: 56) | RSYSGSYTYSFGEYDY (SEQ ID NO: 57) |

TABLE 1-continued

IFNqR3 VHHs and CDRs

| Name | Sequence (CDRs underlined) | CDR1 | CDR2 | CDR3 |
|---|---|---|---|---|
| DR935 | QVQLVESGGGLVQAGGSLRL SCAASGRAFSTYALGWFRQA PGKEREFIAAISRGGGSTDYA DSVKGRFTISRDNAKSTVYLQ MNSLKPEDTAVYYCAARSYS SSYYYSQYEYDYWGQGTQVT VSS (SEQ ID NO: 10) | RAFSTYALG (SEQ ID NO: 58) | AISRGGGST DYADSVKG (SEQ ID NO: 59) | RSYSSSYYYSQ YEYDY (SEQ ID NO: 60) |
| DR936 | EVQLVESGGGLVQAGGSLRLS CAASGRTFSSVAMAWFRQAP GKEREFVSAISSGGGSTDYAD SVKGRFTISKDNAKNTMYLQ MDSLKPEDTAVYYCAARDYS SRRYYQSRYEYDLWGLGTQV TVSS (SEQ ID NO: 11) | RTFSSVAMA (SEQ ID NO: 61) | AISSGGGSTD YADSVKG (SEQ ID NO: 62) | RDYSSRRYYQS RYEYDL (SEQ ID NO: 63) |
| DR937 | QVQLVESGGGLVQPGGSLRLS CAASGRTFRSYSMGWFRQAP GKEREFVAAISWYSGTTYYA DPVKGRFTISRDDAKNTLYLQ MNSLKPEDTAVYYCAANEIA TMESSNDYWGQGTQVTVSS (SEQ ID NO: 12) | RTFRSYSMG (SEQ ID NO: 64) | AISWYSGTT YYADPVKG (SEQ ID NO: 65) | NEIATMESSNDY (SEQ ID NO: 66) |
| DR938 | QVQLVESGGGLVQPGGSLRLS CTASGRPRTTYAMGWFRQAP GKEREIVAAISKAGGSTYVAD SAKGRFAISKDNAKNTVYLQ MNSLKPEDTAVYYCAARAGF AAQIFEYDYWGQGTLVTVSS (SEQ ID NO: 13) | RPRTTYAMG (SEQ ID NO: 67) | AISKAGGST YVADSAKG (SEQ ID NO: 68) | RAGFAAQIFEYDY (SEQ ID NO: 69) |
| DR939 | EVQLVESGGGLVQAGGSMRL SCANSGRTFGTYAMGWFRQS PGKERERVASIDRDGSMSYYA DSVKGRFTISGDNAKNTVYLQ MNSLKPEDTAVYYCAASRRA VISLQTVDYWGQGTQVTVSS (SEQ ID NO: 14) | RTFGTYAMG (SEQ ID NO: 70) | SIDRDGSMS YYADSVKG (SEQ ID NO: 71) | SRRAVISLQTVDY (SEQ ID NO: 72) |
| DR940 | EVQLVESGGRLVQTGGSLRLS CAASGRTFSNYAMGWFRQAP GKEREFVAAISWYSGNTYYA DSVKGRFTISRDNAKNTMYL QMNSLKPEDTAVYYCAANQI ATMISVGDYWGQGTLVTVSS (SEQ ID NO: 15) | RTFSNYAMG (SEQ ID NO: 73) | AISWYSGNT YYADSVKG (SEQ ID NO: 74) | NQIATMISVGDY (SEQ ID NO: 75) |
| DR941 | QVQLVESGGGLVEAGGSLRL ACAASGSIFRLNLMGWYRQA PGKQRELVAHVGTTGNTAYA DSVKGRFTISKDDAKNMVFL QMNSLKPEDTAVYYCYADR WGQFSWGQGTQVTVSS (SEQ ID NO: 16) | SIFRLNLMG (SEQ ID NO: 76) | HVGTTGNTA YADSVKG (SEQ ID NO: 77) | DRWGQFS (SEQ ID NO: 78) |
| DR942 | QVQLVESGGGLVQAGGSLRL SCVASGRTFTGYAMGWFRQA PGKEREFVAVITWSGATTYYS ASVKGRFTLSRDNAKNTVYL QMNSLKSEDTAVYYCAIRIRD GVSPENPNEYGYWGQGTQVT VSS (SEQ ID NO: 17) | RTFTGYAMG (SEQ ID NO: 79) | VITWSGATT YYSASVKG (SEQ ID NO: 80) | RIRDGVSPENP NEYGY (SEQ ID NO: 81) |
| DR943 | QVQLVESGGGLVQAGGSLRL SCVASGRTVGYGMAWFRQAP GKQRDVVAAITWSGTSTYYP DSVKGRFTISRDNAKNTMYL QMSSLKPEDTAVYYCAAGSR RRVGVDVGGYDYWGQGTQV TVSS (SEQ ID NO: 18) | RTVGYGMA (SEQ ID NO: 82) | AITWSGTST YYPDSVKG (SEQ ID NO: 83) | GSRRRVGVDV GGYDY (SEQ ID NO: 84) |

TABLE 1-continued

IFNgR3 VHHs and CDRs

| Name | Sequence (CDRs underlined) | CDR1 | CDR2 | CDR3 |
|---|---|---|---|---|
| DR944 | QVQLVESGGGLVQAGDSLRL SCAASGRTFTFSTHNMGWFR QAPGKEREFVGGIMWTSRAS YADSVKGRFTVSRDNAKNTV YLQMNSLKPEDTAVYYCAAA WYGNSGASYDYWGQGTQVT VSS (SEQ ID NO: 19) | RTFTFSTHNMG (SEQ ID NO: 85) | GIMWTSRAS YADSVKG (SEQ ID NO: 86) | AWYGNSGASYDY (SEQ ID NO: 87) |
| DR945 | QVQLVESGGGLVQLVQAGGS LRLSCAASGRTFSGYNMGWF RQAPGKEREFVAAIAWAGSR TYYTDSVKGRFTISRDNAKNT MYLQMNTLRPEDTAVYYCAA HDETYYRLDRVDLYTHWGQ GTQVTVSS (SEQ ID NO: 20) | RTFSGYNMG (SEQ ID NO: 88) | AIAWAGSRT YYTDSVKG (SEQ ID NO: 89) | HDETYYRLDRV DLYTH (SEQ ID NO: 90) |
| DR946 | QVQLVESGGGLVQPGESLRLS CAASGPFTRYAMGWFRQAPG KEREFVAAISWSSGNTYYVDS VKGRFTISRDNAKNTMYLQM NSLKPEDTAVYYCAANEVAT MSGPDDYWGQGTQVTVSS (SEQ ID NO: 21) | PFTRYAMG (SEQ ID NO: 91) | AISWSSGNT YYVDSVKG (SEQ ID NO: 92) | NEVATMSGPDDY (SEQ ID NO: 93) |
| DR947 | QVQLVESGGGLVQAGGSLRL SCAASGGSFGRYTMGWYRQA PGKEREFVAVISWSGTNTYYA DSVKGRFTISRDNAKNTMYL QMNDLKPEDTAVYYCAARET YYSHWDERMEYDYWGQGTQ VTVSS (SEQ ID NO: 22) | GSFGRYTMG (SEQ ID NO: 94) | VISWSGTNT YYADSVKG (SEQ ID NO: 95) | RETYYSHWDE RMEYDY (SEQ ID NO: 96) |
| DR948 | QVQLVESGGGLVQAGDSLRL SCVASGSIDSSYYVSWFRQAP GKERDLVAAINWGDSRTAYA DSVKGRFTISRDNAKNTVYLQ MHSLRPNDTAVYYCASRIGLG GPVVAAPTRYPYWGQGTLVT VSS (SEQ ID NO: 23) | SIDSSYYVS (SEQ ID NO: 97) | AINWGDSRT AYADSVKG (SEQ ID NO: 98) | RIGLGGPVVAA PTRYPY (SEQ ID NO: 99) |
| DR949 | QVQLVESGGGLVQAGGSLRL SCAASESILRFNVMSWLRQAP GKQRELVAVITSGGSTNYADS VKGRFTISRDNAKNTVYLQM NSLKPEDTAVYYCAADESGQ YYWGQGTQVTVSS (SEQ ID NO: 24) | SILRFNVMS (SEQ ID NO: 100) | VITSGGSTN YADSVKG (SEQ ID NO: 101) | DESGQYY (SEQ ID NO: 102) |
| DR950 | QVQLVESGGGLVQAGGSLRL SCAASGLTTSSAALAWFRQAP GKERELDPTITSGGGSTYYAD SVKGRFTISKDNAKNTLYLQM SSLKPEDTAVYYCAARFYSTT YYYREHEYSDWGQGTQVTVSS (SEQ ID NO: 25) | LTTSSAALA (SEQ ID NO: 103) | TITSGGGSTY YADSVKG (SEQ ID NO: 104) | RFYSTTYYYRE HEYSD (SEQ ID NO: 105) |
| DR951 | QVQLVESGGGLVQAGGSLRL SCAASGRTFGTSFGSLSMGWF RQAPGKEREFVAAISRNIGRT YYADSVKDRFTISRDNAKNTA SLQMNSLEPEDTAVYNCAAT NSYDDLRRSYAYDYWGQGT QVTVSS (SEQ ID NO: 26) | RTFGTSFGSLSMG (SEQ ID NO: 106) | AISRNIGRTY YADSVKD (SEQ ID NO: 107) | TNSYDDLRRSY AYDY (SEQ ID NO: 108) |

TABLE 1-continued

IFNgR3 VHHs and CDRs

| Name | Sequence (CDRs underlined) | CDR1 | CDR2 | CDR3 |
|---|---|---|---|---|
| DR952 | QVQLVESGGGLVQAGGFLRL SCAASGRTFSSLAMAWFRQA PGKEREFVAAISRSGGSTDYA DSVKGRFTISRDNAKSTLYLQ MSSLKPEDTAVYYCAARDYS TLQYYNEYEYSDWGQGTLVT VSS (SEQ ID NO: 27) | RTFSSLAMA (SEQ ID NO: 109) | AISRSGGSTD YADSVKG (SEQ ID NO: 110) | RDYSTLQYYNE YEYSD (SEQ ID NO: 111) |
| DR953 | QVQLVESGGGLVQAGDSLRL SCAASGPTFSTYAMAWFRQA PGKEREFVAAITQSGRTTYYE DSVKGRFTISKDNAKNTLYLQ MNSLQPEDTAVYYCAARDLW SDSPDDWRIYSFWGQGTQVT VSS (SEQ ID NO: 28) | PTFSTYAMA (SEQ ID NO: 112) | AITQSGRTT YYEDSVKG (SEQ ID NO: 113) | RDLWSDSPDD WRIYSF (SEQ ID NO: 114) |
| DR954 | QVQLVESGGGLVQAGGSLRL SCAAARRTLHNFAMAWFRQA PGKEREFVAAISKGGGSADYA DSVKGRFTISRDNAKNTVYLQ MNSLKPEDTAVYYCAANDLA SYSDSSYTSTSRYDYWGQGT QVTVSS (SEQ ID NO: 29) | RTLHNFAMA (SEQ ID NO: 115) | AISKGGGSA DYADSVKG (SEQ ID NO: 116) | NDLASYSDSSY TSTSRYDY (SEQ ID NO: 117) |
| DR955 | QVQLVESGGGLVQTGGSLRLS CAASGRTFSSYAMAWFRQAP GKEREFVAAISILGGSADYEDS VQGRFTISRDNAKNTMYLQM NSLKPEDTAVYYCAARRPAPS DSYWSSTSYAYWGQGTLVTV SS (SEQ ID NO: 30) | RTFSSYAMA (SEQ ID NO: 118) | AISILGGSAD YEDSVQG (SEQ ID NO: 119) | RRPAPSDSYWS STSYAY (SEQ ID NO: 120) |
| DR956 | EVQLVESGGGLVQAGGSLRLS CAASGRTFSSLAMAWFRQAP GKEREFVAATTILGGSADYGD PVKGRFTISRDNAKNTVYLQ MNSLKPEDTAVYYCTGRRPA PSDNYWSPASYAYWGQGTQV TVSS (SEQ ID NO: 31) | RTFSSLAMA (SEQ ID NO: 121) | ATTILGGSA DYGDPVKG (SEQ ID NO: 122) | RRPAPSDNYWS PASYAY (SEQ ID NO: 123) |
| DR957 | QVQLVESGGGLVQAGGSLRL SCAPSGRTFSSYAMAWFRQPP GKEREFVAAITVSGASTYYAD SVKGRFTISRDNAKNSMYLQ MNSLKPEDTAVYYCAAGGPG TIFPDYDYWGQGTQVTVSS (SEQ ID NO: 32) | RTFSSYAMA (SEQ ID NO: 124) | AITVSGAST YYADSVKG (SEQ ID NO: 125) | GGPGTIFPDYDY (SEQ ID NO: 126) |
| DR958 | QVQLVESGGGLVQAGDSLTL SCTASGRTFSGYNMGWFRQA PGKERDFVAAINWIGGATYY ADSVKGRFTISRDNAKNTVYL QMNSLKPEDTAVYYCHRYSE KFYSGKDYYTRDYDWGQG TQVTVSS (SEQ ID NO: 33) | RTFSGYNMG (SEQ ID NO: 127) | AINWIGGAT YYADSVKG (SEQ ID NO: 128) | YSEKFYSGKDY YTRDYDY (SEQ ID NO: 129) |

In some embodiments, the foregoing sets of CDRs are incorporated in a humanized VHH framework to provide "humanized" sdAb IFNgR2 binding molecules.

The disclosure further provides methods of chemical or recombinant processes for the preparation of the IFNgR2 binding molecules of the present disclosure.

The disclosure further provides nucleic acids encoding the IFNgR2 binding molecules. Table 2 below provides examples of DNA sequences encoding IFNgR2 binding molecules as described herein.

TABLE 2

DNA Sequences Encoding IFNgR2 VHHs

| NAME | DNA Sequence |
| --- | --- |
| DR927 | CAGGTGCAGCTGGTGGAGAGCGGAGGCGGACTGGTACAAGCAGGG<br>GGTTCTCTCAGGCTGAGCTGTGCGGCTTCCGGGAGGACTTTCACCTC<br>TTATGCTATGAATTGGTTCCGCCAGGCCCCTGGGAAGGAAAGGGAG<br>TTTGTGGCAGCCATCTCTTGGTCCAGCGGCAATACCTACGTGGCCGA<br>CTCCGTCAAGGGTAGGTTCGCCATCAGCCGGGACAAAGCTAAGAAT<br>ACTATGTACTTGCAGATGAACAGCCTCGCGCCGGAAGATACTGCGG<br>TGTATTACTGCGCCGCTACTACCATCGCCACGATGTCCGACGAGTAT<br>ACATATTGGGACAGGGAACTCAGGTTACAGTATCCTCC<br>(SEQ ID NO: 130) |
| DR928 | CAGGTCCAGCTGGTCGAATCCGGTGGCGGGTTGGTACAGGCGGGTG<br>GCTCCCTGCGCCTGAGCTGCGCCGCGAGTGGGCGTACATTTTCTAAC<br>TACAGAATGGGCTGGTTCAGGCAGGCTCCGGGAAAGGAGCGTGAGT<br>TCGTGGCTGCCATTTCACGCGGAGGTGGCACCACACTGTACGCCGAC<br>TCTGTCAAAGGCCGCTTCACCATCTCTCGCGACAACGCTAAGAATAC<br>TGTTGATCTCCAGATGAACCGCCTGAAGCCGGAAGACACCGCAGTTT<br>ACTTTTGTGCCGCAGGCGATTTCTCTACCACTTGGGACGAGTATAAC<br>TACTGGGGCAGGGAACACAAGTGACCGTGTCCAGT<br>(SEQ ID NO: 131) |
| DR929 | CAGGTTCAACTGGTGGAGAGCGGTGGGGCCTGGTGCAGGCAGGCG<br>GGAGCTTGCGGCTTTCATGTGTTGCATCTGGCCGCACCTTCTCAAGC<br>TATGCGATGGGCTGGTTCCGTCAGACTCCGGGGAAAGAGAGGGAGT<br>TCGTGAGCGCGATTTCTCGCGGTGGAGGCAGCACCGACTATGCCGAT<br>TCCGTGAAGGGCAGGTTTACGATCTCCAGAGATAACGCCAAGAACA<br>CAGTTTATTTGCAGATGAATAACCTGAAATCCGAGGACACCGCAGT<br>GTATTACTGCGCCCTGCGGGCCTATTCAGGCCGCTATTACCAGTTCC<br>TGGAGTACGATTACTGGGGCCAGGGCACACAGGTGACTGTGTCCTCC<br>(SEQ ID NO: 132) |
| DR930 | GAGGTTCAGTTGGTGGAGTCTGGGGGCGGTCTGGTCCAGGCTGGTG<br>GATCATTGCGCCTGAGCTGTACCGTTTCAGGCAGGACTTTTTCTAGC<br>TACGCCGTAGCTTGGTTCCGCCAGGCACCTGGCAACGTCCGGGAGCT<br>GGCGGCTGCCCTGAGTCGCGGGGGAGGCTCTGCTTACTATACAGAC<br>AGTGTCAAGGGTCGCTTCACTATTAGCCGCGACAATGCGAAAAACA<br>CCGTCTACCTTCAGATGAACAGTCTGAAGCCCGAAGACACTGCGGT<br>GTATTACTGCGCGGCCAGGAACTACGACGGCACCTATTACCAGGAA<br>AACCAATACAATTACTGGGGCAGGGAACCCAGGTGACCGTCAGCAGC<br>(SEQ ID NO: 133) |
| DR931 | CAGGTCCAGCTGGTGGAATCAGGCGGAGGCTTGGTGCAGGCCGGGG<br>GCAGTCTGTTGCTGTCTTGCGCCGCGAGCGGACGCACATTCTCCACC<br>TACGCTATGGGGTGGTTCCGCCAGGCACCTGGAAAAGAACGCATGT<br>TTGTCGCGGCCATCTCCGTTAACGGAGGCAGTACCTACTATGCAGAT<br>TCTGTTACGGGCCGTTTCACCATTAGCCGCGACAATGCGAAAAACAC<br>CATGTATTTGCAAATGAATAACCTGAAGCCTGGTGACACAGCCGTGT<br>ATTACTGCGCAGCGCGTCGCCCCTACCCCGGTTCCGACTTTCTCACA<br>TGGGCCTCCTACGATTACAGGGGCCAGGGCACCCTGGTGACCGTGTC<br>TAGT<br>(SEQ ID NO: 134) |
| DR932 | CAGGTTCAGCTGGTCGAATCTGGCGGTGGACTGGTGCAAGCTGGTG<br>GGTTCCTGCGCCTCAGCTGTGCCGCTAGTGGCCGTACCTTTAGCTAT<br>ACAACCATCGGCTGGTTCCGCCAGGCTCCAGGGAAGGAACGCGAGT<br>TCGTCGCCGTGATCTCAGCAGGAGGCGGTTCCCGCGATTACGCGGAC<br>GCCCTCAAAGGACGCTTTACAATCTCTCGCGATAACGCTAAAAAGAT<br>GGTTTATTTGCAAATGAATAACTTGAAGCCCGAGGATACCGCCGTGT<br>ATTACTGCGCCGTGAGGCGGAATACTGACACATATACCACAACCGG<br>CGACTACGACTACTGGGGTCAGGGCACCCAGGTTACCGTTTCATCC<br>(SEQ ID NO: 135) |
| DR933 | CAAGTTCAGCTTGTAGAGTCTGGCGGGGGCCTGGTGCAACCCGGTG<br>ACTCACTGAGGCTGTCTTGTGTGGCCTCCGGGGGTACAATTTCCTCA |

TABLE 2-continued

DNA Sequences Encoding IFNgR2 VHHs

| NAME | DNA Sequence |
|---|---|
| | CTGGCTATGGGTTGGTTCAGGCAGGCTCCGGGTAAGGAGAGGGAGT<br>TTGTCGCAGCCATCAGCTGGTCTGGCCGCTCAACATATTACGTGGAT<br>AGCGTGAAAGGCCGCTTCACTATTTCTACTGATAACGCGAAGAATAC<br>CGTGTATCTCCAAATGAACTCCCTGAAACCGGAGGACACAGCGGTG<br>TACTATTGCGTCGCAGGCGAGGATGGACACAGCGAGTATGACTATT<br>GGGGCCAAGGCACCCAGGTCACAGTGTCCTCA<br>(SEQ ID NO: 136) |
| DR934 | CAGGTGCAGCTTGTGGAGAGCGGAGGCGGGCTGGTGCAGGCCGGGG<br>GTAGCTTGCGCCTCAGCTGTGCTGCCTCTGGACGCTCATTTGCCAAC<br>TACGCAATGGGCTGGTTCCGTCAGGCTCCTGGGAAAGAGCGCGAGA<br>CCGTGGCGGCCATCAGTCGCGGGGAGGCAGCACGTGGTACGCGGA<br>CTCAGTCAAGGGGAGGTTTACTATTTCCAAGGATAACGCTAAGAAC<br>ACCGTGTATCTGCAAATGAACAGCCTCAAGCCCGAGGACACAGCAA<br>TCTACTATTGCGCGGCCCGCAGTTACTCCGGCTCCTACACTTATTCCT<br>TCGGCGAGTACGACTACTGGGGTCAGGGCACCCAAGTTACCGTGTC<br>CTCC<br>(SEQ ID NO: 137) |
| DR935 | CAGGTGCAGCTGGTTGAGTCTGGAGGCGGTCTTGTCCAGGCTGGTGG<br>CTCCTTGCGCCTGAGCTGTGCCGCTTCCGGGAGAGCTTTCTCCACAT<br>ACGCTCTCGGCTGGTTCAGGCAGGCCCCCGGAAAGGAGCGCGAGTT<br>CATCGCTGCAATCAGCCGGGGCGGTGGCAGCACTGATTATGCAGAT<br>TCTGTGAAGGGACGCTTCACCATCTCTCGTGATAACGCCAAGTCTAC<br>CGTATATTTGCAGATGAATAGTCTGAAGCCCGAAGACACCGTGTGT<br>ATTACTGTGCAGCGCGTAGCTACTCCTCTAGTTACTATTACTCTCAGT<br>ACGAGTACGACTACTGGGGACAGGGTACTCAGGTGACTGTGTCCAGC<br>(SEQ ID NO: 138) |
| DR936 | GAGGTCCAGCTCGTGGAGAGTGGCGGTGGCCTCGTGCAGGCCGGGG<br>GCTCCCTGAGACTGAGTTGTGCCGCTTCTGGCCGCACCTTCAGTTCA<br>GTCGCTATGGCTTGGTTTCGGCAGGCCCTGGCAAGGAGCGCGAGTT<br>CGTGTCCGCTATCAGTTCTGGAGGCGGTTCCACGGATTACGCTGATA<br>GCGTGAAGGGCAGATTCACTATCAGCAAGGACAACGCTAAGAACAC<br>CATGTATCTCCAGATGGACTCTCTTAAACCCGAGGATACCGCCGTGT<br>ATTACTGCGCCGCTCGCGACTATTCTAGCCGTCGCTATTACCAGTCC<br>CGGTACGAGTACGACCTCTGGGGCCTGGGAACCCAAGTCACAGTCT<br>CCTCC<br>(SEQ ID NO: 139) |
| DR937 | CAGGTGCAGTTGGTGGAGTCCGGTGGGGGCCTGGTGCAGCCAGGTG<br>GAAGCCTCCGCCTGTCCTGTGCTGCAAGTGGCCGCACCTTTAGGTCC<br>TACTCAATGGGCTGGTTTCGTCAGGCTCCAGGAAAGGAACGGGAGT<br>TCGTTGCCGCTATTTCCTGGTATTCCGGGACAACGTACTATGCCGAC<br>CCAGTCAAGGGTAGATTCACTATCAGCCGGGACGATGCAAAGAACA<br>CTCTCTACTTGCAGATGAACTCCCTGAAGCCCGAGGACACCGCCGTG<br>TATTACTGCGCGGCTAACGAGATCGCCACAATGGAATCCTCTAACGA<br>TTACTGGGGCCAGGGGACCCAGGTTACCGTCTCTAGC<br>(SEQ ID NO: 140) |
| DR938 | CAGGTGCAGCTGGTCGAGAGTGGAGGGGGATTGGTCCAGCCTGGTG<br>GCTCTCTGCGCCTGTCATGCACTGCTTCAGGCCGCCCCCGTACAACG<br>TATGCAATGGGCTGGTTCCGTCAGGCTCCCGGCAAGGAGCGCGAGA<br>TCGTGGCGGCTATTTCCAAAGCCGGAGGCTCTACCTACGTGGCCGAC<br>TCTGCGAAAGGCCGCTTTGCCATCTCTAAGGACAACGCCAAGAATA<br>CCGTCTATCTGCAAATGAACAGCCTCAAGCCTGAGGATACCGCAGTT<br>TATTACTGTGCAGCTCGCGCAGGCTTCGCTGCCCAAATCTTCGAGTA<br>CGACTACTGGGGACAGGGCACCCTGGTGACAGTGTCTAGC<br>(SEQ ID NO: 141) |
| DR939 | GAGGTTCAACTGGTCGAGTCCGGGGGCGGGCTCGTGCAGGCCGGAG<br>GTTCCATGCGCCTGTCCTGTGCCAATTCCGGTAGAACCTTTGGGACC<br>TATGCTATGGGCTGGTTCCGCCAGTCACCCGGCAAAGAGCGCGAGC<br>GGGTCGCGTCCATCGACCGTGACGGTTCTATGTCCTATTACGCCGAC<br>AGCGTGAAAGGCAGGTTCACAATCAGCGGAGACAATGCGAAGAAC<br>ACCGTGTATCTCCAGATGAACTCCCTGAAACCTGAGGACACCGCCGT<br>CTATTACTGCGCGGCTTCAAGACGCGCCGTTATTTCTCTCCAGACAG<br>TTGATTACTGGGGCCAGGGAACCCAGGTGACTGTGTCCAGC<br>(SEQ ID NO: 142) |
| DR940 | GAAGTGCAGCTCGTGGAGTCTGGTGGCCGTTTGGTCCAGACCGGAG<br>GCAGCTTGAGGCTCTCATGCGCTGCCTCTGGCAGGACATTTTCCAAT<br>TATGCAATGGGATGGTTTCGTCAGGCTCCTGGCAAGGAGAGGGAGT<br>TCGTGGCTGCAATCTCTTGGTACAGCGGCAACACATACTATGCCGAC<br>TCCGTGAAAGGCAGGTTTACCATCAGCCGGGATAACGCCAAAAACA<br>CTATGTATCTCCAGATGAACTCCCTGAAGCCAGAGGATACGGCGGTC |

TABLE 2-continued

DNA Sequences Encoding IFNgR2 VHHs

| NAME | DNA Sequence |
|------|--------------|
|  | TATTACTGTGCAGCCAATCAAATCGCCACTATGATTAGCGTGGGCGA<br>CTACTGGGGCCAAGGCACCCTGGTGACAGTGTCATCC<br>(SEQ ID NO: 143) |
| DR941 | CAGGTGCAGTTGGTCGAGTCAGGAGGGGGCCTGGTCGAGGCCGGGG<br>GCTCCCTGAGGCTCGCTTGCGCTGCGAGTGGATCAATCTTCCGTTTG<br>AACCTGATGGGATGGTATAGACAGGCTCCTGGCAAGCAGCGTGAAC<br>TGGTCGCACACGTGGGTACTACAGGAAACACCGCCTACGCCGACTC<br>TGTCAAGGGGCGCTTTACCATCTCAAAGGACGATGCTAAGAACATG<br>GTGTTTCTCCAGATGAACTCCCTCAAGCCCGAGGATACTGCCGTCTA<br>TTACTGCTATGCGGACCGCTGGGGTCAGTTCTCCTGGGGCCAGGGAA<br>CACAGGTAACCGTTTCTTCA<br>(SEQ ID NO: 144) |
| DR942 | CAGGTGCAGCTCGTGGAGTCTGGCGGTGGCCTGGTCCAGGCCGGAG<br>GCAGCCTCCGGTTGAGCTGTGTAGCTAGTGGCCGTACCTTTACGGGC<br>TACGCGATGGGCTGGTTCAGACAAGCGCCTGGCAAGGAGAGGGAGT<br>TCGTCGCCGTGATTACTTGGTCCGGGGCCACTACCTATTACTCCGCTT<br>CCGTGAAGGGCCGTTTCACGCTGAGCCGGGATAACGCCAAAAACAC<br>AGTGTACCTCCAGATGAACTCCCTGAAGTCCGAGGACACTGCCGTTT<br>ATTACTGCGCCATTCGCATCCGGGACGGAGTGTCTCCTGAAAACCCT<br>AACGAGTACGGTTACTGGGGCCAGGGCACCCAGGTAACCGTGTCCTCA<br>(SEQ ID NO: 145) |
| DR943 | CAGGTCCAGCTCGTGGAGTCCGGCGGGGGCTTGGTTCAGGCTGGGG<br>GAAGCCTGCGTCTGTCATGCGTGGCGAGCGGGAGGACCGTCGGCTA<br>CGGCATGGCTTGGTTTAGGCAGGCTCCTGGCAAGCAACGCGATGTTG<br>TGGCCGCGATCACTTGGTCCGGCACTTCCACCTATTACCCCGACTCA<br>GTCAAGGGGCGCTTCACCATCTCCAGAGATAACGCCAAGAACACTA<br>TGTATCTCCAGATGTCATCTCTGAAGCCAGAAGATACCGCTGTATAT<br>TACTGCGCCGCTGGCTCCCGTCGCCGGGTGGGCGTGGACGTGGGTG<br>GATACGACTACTGGGGCCAAGGCACTCAGGTGACCGTCTCCAGC<br>(SEQ ID NO: 146) |
| DR944 | CAGGTGCAGCTCGTCGAGAGCGGGGCGGACTGGTACAGGCTGGCG<br>ACTCCTTGCGTCTGAGCTGCGCCGCGTCCGGCAGGACGTTCACCTTC<br>TCAACTCACAATATGGGCTGGTTCCGTCAGGCACCGGGTAAGGAGA<br>GAGAGTTCGTCGGAGGCATCATGTGGACCAGCCGGGCAAGTTACGC<br>CGATTCTGTGAAGGGTCGTTTCACCGTAAGCCGTGATAACGCGAAG<br>AACACTGTCTACTTGCAGATGAACTCTCTGAAGCCCGAGGACACTGC<br>GGTTTACTATTGCGCTGCCGCATGGTATGGTAACAGCGGAGCCTCCT<br>ACGACTACTGGGGTCAAGGAACTCAGGTCACGGTCAGCTCC<br>(SEQ ID NO: 147) |
| DR945 | CAGGTCCAACTGGTCGAGTCTGGCGGAGGCCTCGTGCAACTTGTTCA<br>AGCCGGGGGCAGCCTGCGCCTTTCTTGTGCTGCGAGTGGCCGCACCT<br>TTTCCGGGTATAACATGGGTTGGTTTCGTCAGGCCCCAGGTAAGGAG<br>CGCGAGTTCGTGGCTGCCATTGCTTGGGCAGGCAGCAGGACATATTA<br>CACCGATAGCGTCAAGGGGCGGTTTACTATCTCGCGACAATGCAA<br>AAAACACTATGTACCTCCAGATGAACACCCTGCGTCCTGAGGATAC<br>AGCCGTGTATTACTGCGCAGCCCATGACGAGACCTATTACCGCCTTG<br>ACCGGGTGGACCTCTATACCCACTGGGGCCAGGGAACCCAGGTCAC<br>TGTGTCCTCC<br>(SEQ ID NO: 148) |
| DR946 | CAGGTGCAACTGGTTGAGTCCGGGGGCGGACTGGTGCAACCTGGCG<br>AGAGTCTGCGCCTGTCCTGCGCGGCCTCCGGTCCTTTTACTAGATAT<br>GCGATGGGTTGGTTCCGTCAAGCGCCTGGGAAGGAGCGTGAGTTCG<br>TCGCGGCTATCAGCTGGTCATCTGGAAATACGTATTACGTGGATTCC<br>GTGAAGGGCAGGTTCACTATTTCCAGAGACAACGCTAAGAACACAA<br>TGTACTTGCAGATGAACAGCCTGAAGCCAGAGGACACAGCGGTTTA<br>CTATTGTGCTGCAAACGAGGTCGCCACCATGAGTGGACCCGATGACT<br>ATTGGGGACAAGGTACACAAGTCACTGTGTCCTCT<br>(SEQ ID NO: 149) |
| DR947 | CAGGTGCAGCTGGTGGAGTCTGGAGGTGGGCTGGTGCAGGCGGGAG<br>GCTCTCTGCGTCTGTCTTGTGCTGCCAGCGGCGGTTCCTTTGGCCGGT<br>ACACAATGGGATGGTATCGTCAAGCGCCTGGTAAGGAGCGCGAGTT<br>TGTTGCTGTGATCTCATGGAGCGGCACAAACACGTACTATGCGGACA<br>GCGTGAAGGGTCGCTTTACCATTTCCCGTGATAACGCGAAGAATACC<br>ATGTACCTGCAAATGAACGATTTGAAACCCGAAGATACCGCAGTTT<br>ATTACTGTGCTGCGCGTGAGACTTATTACTCACACTGGGACGAAAGG<br>ATGGAGTATGACTATTGGGGCCAGGGCACCCAGGTTACAGTATCTTCC<br>(SEQ ID NO: 150) |

TABLE 2-continued

DNA Sequences Encoding IFNgR2 VHHs

| NAME | DNA Sequence |
|---|---|
| DR948 | CAGGTCCAGCTCGTAGAAAGCGGAGGTGGCCTTGTCCAAGCTGGCG<br>ACAGCCTGCGCCTTTCCTGCGTTGCCAGCGGCTCCATCGACTCATCC<br>TATTACGTGTCTTGGTTCCGTCAGGCACCAGGCAAGGAACGTGATCT<br>GGTAGCTGCCATCAACTGGGGCGATTCTCGCACCGCCTATGCTGACT<br>CCGTTAAGGGCCGGTTCACGATCTCCCGTGATAACGCGAAAAATACT<br>GTGTATCTCCAGATGCACTCCCTGCGCCCCAACGATACCGCAGTGTA<br>TTACTGTGCCAGCAGAATTGGGCTGGGCGGCCGGTGGTTGCGGCC<br>CCCACCCGTTATCCCTATTGGGGCCAGGGCACCCTGGTAACCGTGTC<br>TTCC<br>(SEQ ID NO: 151) |
| DR949 | CAAGTGCAACTGGTAGAGTCAGGCGGTGGCCTTGTGCAGGCCGGTG<br>GCTCTCTGCGCCTGTCTTGCGCTGCCTCTGAGTCTATCTTGCGGTTTA<br>ACGTGATGTCATGGTTGCGTCAGGCACCAGGGAAACAGCGTGAGCT<br>GGTGGCAGTCATCACTAGCGGTGGCAGCACGAATTATGCAGACTCC<br>GTGAAAGGCCGCTTCACGATCTCTCGTGACAACGCTAAAAACACCG<br>TGTATCTCCAGATGAACAGCCTGAAGCCAGAAGACACTGCCGTGTA<br>TTACTGTGCTGCCGACGAGAGCGGGCAGTATTACTGGGGACAGGGC<br>ACTCAGGTGACAGTCAGCAGC<br>(SEQ ID NO: 152) |
| DR950 | CAGGTCCAGCTCGTGGAGTCTGGGGGCGGTCTCGTCCAGGCTGGGG<br>GTTCCCTGCGGCTGAGCTGTGCCGCTTCTGGCTTGACGACCAGTAGC<br>GCCGCTCTGGCTGGTTTCGTCAGGCTCCTGGCAAGGAGCGTGAGCT<br>TGATCCAACTATTACCAGCGGCGGAGGCTCTACCTACTATGCCGACA<br>GCGTTAAGGGTCGGTTTACCATCAGCAAAGACAACGCTAAGAACAC<br>TCTTTATCTCCAGATGTCAAGCCTCAAACCTGAGGACACCGCCGTCT<br>ACTATTGCGCCGCTCGCTTTTATAGCACCACTTACTATTACCGCGAA<br>CACGAGTATAGTGACTGGGGGCAGGGCACCCAAGTCACAGTGAGCAGC<br>(SEQ ID NO: 153) |
| DR951 | CAGGTGCAACTGGTGGAATCTGGGGGTGGCTTGGTGCAGGCTGGCG<br>GTCTCTGCGTCTGTCCTGTGCGGCTTCAGGACGCACTTTCGGCACC<br>AGCTTTGGCAGCCTGAGCATGGGCTGGTTCAGACAAGCCCCCGGCA<br>AAGAGCGTGAGTTCGTGGCTGCCATCTCTCGCAACATTGGCCGTACT<br>TATTACGCAGATTCCGTGAAAGACAGGTTTACGATCTCTCGCGACAA<br>CGCTAAGAATACCGCCTCTCTTCAGATGAACTCTCTGGAGCCCGAAG<br>ACACTGCTGTCTATAATTGTGCCGCGACAAACTCCTACGATGACCTT<br>AGGCGCTCCTACGCCTACGACTACTGGGGACAGGGCACCCAGGTGA<br>CAGTCAGCTCC<br>(SEQ ID NO: 154) |
| DR952 | CAGGTCCAGCTGGTGGAGAGCGGCGGTGGGCTGGTTCAGGCTGGAG<br>GCTTCCTGCGCCTGTCTTGCGCTGCCTCAGGTCGTACTTTTTCCTCTT<br>TGGCAATGGCTTGGTTCCGTCAAGCTCCCGGCAAGGAGCGCGAGTTC<br>GTAGCCGCTATCTCCCGCTCTGGAGGCTCTACCGACTACGCTGACAG<br>CGTCAAGGGACGCTTCACCATCTCTCGGGACAACGCCAAGTCCACCC<br>TGTACTTGCAGATGTCTAGCCTGAAACCTGAGGATACAGCGGTGTAT<br>TACTGCGCTGCACGTGACTACTACTCTCCAGTATTACAATGAGTA<br>TGAATACTCCGACTGGGGCCAAGGCACTCTGGTCACTGTGTCCTCA<br>(SEQ ID NO: 155) |
| DR953 | CAGGTGCAGCTCGTAGAGTCTGGCGGTGGCCTGGTCCAGGCTGGGG<br>ACTCACTGCGTCTGAGTTGTGCCGCGTCCGGCCCTACCTTCAGTACG<br>TATGCAATGGCCTGGTTTCGCCAAGCTCCAGGTAAGGAACGCGAGTT<br>CGTGGCTGCCATTACCCAGAGTGGTCGCACCACTTACTATGAAGATT<br>CTGTGAAGGGGCGGTTCACCATTAGCAAGGATAATGCCAAGAACAC<br>CCTCTATCTCCAGATGAACAGCCTCCAGCCTGAAGATACGGCGGTGT<br>ATTACTGCGCGGCCCGCGACTTGTGGTCTGATTCTCCCGATGACTGG<br>AGAATTTACTCTTTCTGGGGACAGGGGACCCAAGTAACAGTCAGTTCC<br>(SEQ ID NO: 156) |
| DR954 | CAGGTTCAGCTTGTGGAGTCCGGTGGCGGTCTGGTCCAGGCAGGTG<br>GCTCCCTGCGGCTGTCTTGCGCAGCCGCTCGTCGCACACTGCACAAC<br>TTCGCAATGGCGTGGTTTCGCCAGGCCCCTGGTAAGGAGAGGGAGT<br>TTGTGGCTGCCATTTCTAAGGGAGGCGGTTCCGCCGACTACGCCGAT<br>AGCGTTAAGGGGCGCTTTACCATTAGTAGGGACAACGCTAAGAACA<br>CAGTGTACCTCCAGATGAACAGCCTCAAGCCAGAGGATACCGCAGT<br>TTACTATTGCGCTGCCAACGATCTGGCTTCTTATAGCGACAGCTCTT<br>ACACATCCACAAGCCGCTACGACTACTGGGGTCAGGGCACCCAGGT<br>TACAGTGTCCTCT<br>(SEQ ID NO: 157) |
| DR955 | CAGGTGCAGCTCGTCGAGTCTGGCGGGGGACTGGTGCAGACTGGTG<br>GCTCCCTGCGCCTCTCTTGCGCGGCCTCTGGCCGCACCTTCTCATCCT |

TABLE 2-continued

| DNA Sequences Encoding IFNgR2 VHHs | |
|---|---|
| NAME | DNA Sequence |
| | ATGCTATGGCTTGGTTCCGTCAAGCGCCCGGTAAAGAGAGGGAGTTT GTGGCCGCTATCTCTATCCTCGGTGGCAGCGCTGACTACGAGGATTC CGTTCAGGGACGCTTCACTATCTCAAGAGATAACGCCAAGAACACT ATGTACCTTCAGATGAACTCCCTCAAGCCAGAGGACACCGCTGTGTA TTACTGTGCCGCTCGCAGACCGGCTCCCTCCGACAGCTACTGGAGCA GTACAAGTTACGCATACTGGGGACAGGGGACCCTGGTGACAGTGTC CAGT (SEQ ID NO: 158) |
| DR956 | GAGGTACAGCTGGTCGAATCCGGTGGCGGTCTGGTGCAGGCTGGCG GAAGCCTGCGCTTGAGCTGTGCGGCCTCTGGCCGCACTTTCAGCTCT CTTGCAATGGCGTGGTTCCGCCAGGCCCCTGGAAAGGAGCGCGAGT TCGTGGCCGCGACCACAATCCTCGGAGGCTCCGCCGACTACGGCGA CCCGGTCAAGGGCCGCTTCACAATCTCCCGCGATAATGCTAAGAAC ACGGTGTATCTCCAGATGAACTCACTGAAGCCAGAGGATACCGCCG TTTATTACTGCACTGGGAGACGCCCCGCTCCATCCGACAACTACTGG TCCCCTGCCAGCTATGCTTACTGGGGACAAGGCACCCAAGTTACCGT GAGCAGT (SEQ ID NO: 159) |
| DR957 | CAGGTGCAGTTGGTGGAAAGCGGCGGTGGCCTTGTGCAGGCTGGCG GTTCACTGCGCCTCAGCTGCGCACCTTCCGGTCGCACCTTCTCCTCTT ACGCGATGGCGTGGTTTCGCCAGCCTCCAGGCAAGGAACGGGAGTT TGTGGCTGCCATTACCGTTTCCGGCGCAAGTACCTATTACGCTGACT CTGTTAAGGGCCGTTTCACCATCTCTCGCGATAATGCGAAAAACTCT ATGTACCTTCAGATGAACTCTTTGAAACCGGAGGATACCGCTGTGTA CTATTGTGCAGCTGGCGGTCCCGGAACCATCTTCCCAGACTATGATT ACTGGGGTCAGGGTACTCAGGTCACCGTCTCCTCC (SEQ ID NO: 160) |
| DR958 | CAAGTACAGCTCGTCGAATCCGGCGGTGGACTGGTGCAGGCCGGAG ATTCCCTTACCCTGTCTTGCACCGCTTCCGGTCGCACCTTTTCAGGTT ACAATATGGGCTGGTTCAGGCAGGCCCCTGGTAAGGAGCGCGACTT CGTCGCTGCCATCAACTGGATCGGAGGTGCTACCTATTACGCGGATA GCGTGAAAGGCCGCTTTACCATTAGCAGGGATAATGCCAAGAACAC TGTCTACCTGCAAATGAACAGCCTGAAGCCCGAGGATACTGCCGTGT ATTACTGCCATCGCTATTCCGAGAAGTTCTACAGCGGGAAGGACTAC TATACTCGTGACTACGACTACTGGGGTCAGGGTACACAGGTAACTGT GTCCTCA (SEQ ID NO: 161) |

The disclosure further provides recombinant viral and non-viral vectors comprising a nucleic acid encoding the IFNgR2 binding molecules of the present disclosure or the CDRs of the IFNgR2 binding molecules of the present disclosure.

The disclosure further provides host cells comprising recombinant viral and non-viral vectors comprising a nucleic acid the IFNgR2 binding molecules of the present disclosure or the CDRs of the IFNgR2 binding molecules of the present disclosure.

The disclosure further provides host cells comprising recombinant viral and non-viral vectors comprising a nucleic acid the IFNgR2 binding molecules of the present disclosure or the CDRs of the IFNgR2 binding molecules of the present disclosure.

The disclosure further provides pharmaceutical formulations comprising the recombinant viral and non-viral vectors comprising a nucleic acid the IFNgR2 binding molecules of the present disclosure and methods of use thereof in the treatment or prevention of diseases, disorders or conditions in a mammalian subject.

The disclosure further provides kits comprising the IFNgR2 binding molecules of the present disclosure.

In another aspect, the present disclosure provides constructs for the targeted delivery of therapeutic agents to a cell expressing the IFNgR2 receptor, wherein the IFNgR2 binding molecule is conjugated to one or more therapeutic agents, optionally through a chemical or polypeptide linker.

In some embodiments, the IFNgR2 binding molecules of the present disclosure are useful to inhibit the activity of interferon gamma in vitro and/or in vivo. In some embodiments, the IFNgR2 binding molecules of the present disclosure are useful in the treatment of autoimmune diseases. The disclosure further provides methods of use of the foregoing in the treatment of an autoimmune disease in a subject, the method comprising administering to the subject a therapeutically effective amount IFNgR2 binding molecule of the present disclosure. In some embodiments, the IFNgR2 binding molecules of the present disclosure may be used alone or in combination with one or more supplementary therapeutic agents. In some embodiments, the diseases amenable to treatment are diseases, disorders or conditions associated with signaling from receptor comprising the IFNgR2. In some embodiments, the IFNgR2 binding molecules of the present disclosure are useful in the treatment of diseases associated with dysregulated T cell or B cell activity. In some embodiments, the IFNgR2 binding molecules of the present disclosure are useful in the treatment of autoimmune diseases. In some embodiments, the IFNgR2 binding molecule of the present disclosure is administered to a subject in a pharmaceutically acceptable formulation. In some embodiments, the IFNgR2 binding molecule of the present disclosure is administered by the administration to the subject of a composition comprising a recombinant viral or non-viral vector comprising a nucleic acid sequence encoding the IFNgR2 binding molecule of the present disclosure.

In another aspect, the present disclosure provides constructs for the identification of cells expressing the IFNgR2 receptor wherein the IFNgR2 binding molecule is conjugated to one or more imaging agents, optionally through a chemical or polypeptide linker. The disclosure further provides methods of use of the foregoing in the identification of cells expressing the IFNgR2 receptor in a subject, the method comprising the administration of an effective amount of the IFNgR2 binding molecule conjugated to the imaging agent to a subject in need of treatment and evaluating the subject for the presence of the imaging agent that is conjugated to the IFNgR2 binding molecule.

In another aspect, the present disclosure provides IFNgR2 binding molecules which have been modified for extended duration of action in vivo wherein the IFNgR2 binding molecule is conjugated to one or more carrier molecules.

The present disclosure provides IFNgR2 binding molecules comprising a polypeptide sequence that specifically binds to the extracellular domain of the IFNgR2 and methods of use thereof in the isolation, depletion or enrichment of cells expressing the IFNgR2 receptor in a biological sample.

DETAILED DESCRIPTION OF THE INVENTION

Introduction

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this disclosure is not limited to particular method or composition described, as such may, of course, vary.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms “a”, “an”, and “the” include plural referents unless the context clearly dictates otherwise. Thus, for example, reference to “a cell” includes a plurality of such cells and reference to “the peptide” includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated that throughout this disclosure reference is made to amino acids according to the single letter or three letter codes. For the reader’s convenience, the single and three letter amino acid codes are provided in Table 3 below:

TABLE 3

Amino Acid Abbreviations

| Single Letter Abbreviation | Name | 3-letter abbreviation |
|---|---|---|
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g., an assay) or biological or chemical property (e.g., the degree of binding of the molecule to another molecule) or of a physical property of a material or cell (e.g., modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [proliferation]/[mg protein], plaque forming units (pfu), etc. As used herein, the term proliferative activity refers to an activity that promotes cell proliferation and replication, including dysregulated cell division such as that observed in neoplastic diseases, inflammatory diseases, fibrosis, dysplasia, cell transformation, metastasis, and angiogenesis.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g., an a IFNgR2 binding molecule or an engineered cell expressing an IFNgR2 binding molecule, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, intracranial injection, intratumoral injection, transdermal, transmucosal, iontophoretic delivery, intralymphatic injection, intragastric infusion, intraprostatic injection, intravesical infusion (e.g., bladder), inhalation (e.g respiratory inhalers including dry-powder inhalers), intraocular injection, intraabdominal injection, intralesional injection, intraovarian injection, intracerebral infusion or injection, intracerebroventricular injection (ICVI), and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant $K_D$, a ratio of the dissociation rate constant between the molecule and the its target ($k_{off}$) and the association rate constant between the molecule and its target ($k_{on}$).

Agonist: As used herein, the term "agonist" refers to a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state resulting in a biological response that mimics the effect of the endogenous ligand of the receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that can produce a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist.

Antagonist: As used herein, the term "antagonist" or "inhibitor" refers to a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway including an immune checkpoint pathway, or cell.

Antibody: As used herein, the term "antibody" refers collectively to: (a) a glycosylated or non-glycosylated immunoglobulin that specifically binds to target molecule, and (b) immunoglobulin derivatives thereof, including but not limited to antibody fragments such as single domain antibodies. In some embodiments the immunoglobulin derivative competes with the immunoglobulin from which it was derived for binding to the target molecule. The term antibody is not restricted to immunoglobulins derived from any particular species and includes murine, human, equine, camelids, antibodies of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies, camelized (in the case of VHHs), or molecules comprising binding domains of antibodies (e.g., CDRs) in non-immunoglobulin scaffolds. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries. In one embodiment, an "antibody" is a mammalian immunoglobulin of the IgG1, IgG2, IgG3 or IgG4 class. In some embodiments, the antibody is a "full length antibody" comprising variable and constant domains providing binding and effector functions. The term "single domain antibody" (sdAb) as used herein refers an antibody fragment consisting of a monomeric variable antibody domain that is able to bind specifically to an antigen and compete for binding with the parent antibody from which it is derived. The term "single domain antibody" includes scFv and VHH molecules. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks.

Biological Sample: As used herein, the term "biological sample" or "sample" refers to a sample obtained (or derived) from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, tumor tissue, including immunoglobulin enriched or cell-type specific enriched fractions derived from one or more of such tissues.

IFNgR2 cell: The terms "IFNgR2 cell", "IFNgR2-expressing cell", "IFNgR2-positive cell" and "IFNgR2+" cell are used interchangeably herein to refer to a cell which expresses and displays the IFNgR2 antigen on the extracellular surface of the cell membrane. Similarly, the terms "IFNgR2-negative cell", "IFNgR2-cells" as are used interchangeably herein to describe cells which do not express or display IFNgR2 antigen on the cell surface.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., *J Biol. Chem.* 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. The term "Chothia Numbering" as used herein is recognized in the arts and refers to a system of numbering amino acid residues based on the location of the structural loop regions (Chothiaet al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs2 and 3 in the variable region of an antibody follows Kabat numbering or simply, "Kabat." The positioning of CDR1 in the variableregion of an antibody follows a hybrid of Kabat and Chothia numbering schemes.

Clonotype: A clonotype is defined as a collection of binding molecules that originate from the same B-cell progenitor cell. The term "clonotype" is used herein to refer to a collection of antigen binding molecules that belong to the same germline family, have the same CDR3 lengths, and have 70% or greater homology in CDR3 sequence Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 35%, alternatively by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Conservative Amino Acid Substitution: As used herein, the term "conservative amino acid substitution" refers to an amino acid replacement that changes a given amino acid to a different amino acid with similar biochemical properties (e.g., charge, hydrophobicity, and size). For example, the amino acids in each of the following groups can be considered as conservative amino acids of each other: (1) hydrophobic amino acids: alanine, isoleucine, leucine, tryptophan, phenylalanine, valine, proline, and glycine; (2) polar amino acids: glutamine, asparagine, histidine, serine, threonine, tyrosine, methionine, and cysteine; (3) basic amino acids: lysine and arginine; and (4) acidic amino acids: aspartic acid and glutamic acid.

Derived From: As used herein in the term "derived from", in the context of an amino acid sequence is meant to indicate that the polypeptide or nucleic acid has a sequence that is based on that of a reference polypeptide or nucleic acid and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological response observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (about 50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect.

Enriched: As used herein in the term "enriched" refers to a sample that is non-naturally manipulated so that a species (e.g., a molecule or cell) of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein (e.g., a cell surface receptor) which is external to of the plasma membrane of a cell. The cell surface protein may be transmembrane protein, a cell surface or membrane associated protein.

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as BLAST 2.0 algorithms, which are described in Altschul et al. (1990) *J Mol. Biol.* 215: 403-410 and Altschul, et al. (1977) *Nucleic Acids Res.* 25: 3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0). For amino acid sequences, a scoring matrix is used to calculate the cumulative score. Extension of the word hits in each direction are halted when: (a) the cumulative alignment score falls off by the quantity X from its maximum achieved value; the cumulative score goes to zero or below, due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) *PNAS (USA)* 89:10915-10919).

In An Amount Sufficient Amount to Cause a Response: As used herein the phrase "in an amount sufficient to cause a response" is used in reference to the amount of a test agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

In Need of Treatment: The term "in need of treatment" as used herein refers to a judgment made by a physician or other caregiver with respect to a subject that the subject requires or will potentially benefit from treatment. This judgment is made based on a variety of factors that are in the realm of the physician's or caregiver's expertise.

In Need of Prevention: As used herein the term "in need of prevention" refers to a judgment made by a physician or other caregiver with respect to a subject that the subject requires or will potentially benefit from preventative care.

This judgment is made based upon a variety of factors that are in the realm of a physician's or caregiver's expertise.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Intracellular Domain: As used herein the term "intracellular domain" or its abbreviation "ICD" refers to the portion of a cell surface protein (e.g., a cell surface receptor) which is inside of the plasma membrane of a cell. The ICD may include the entire cytoplasmic portion of a transmembrane protein or membrane associated protein, or intracellular protein.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

Kabat Numbering: The term "Kabat numbering" as used herein is recognized in the art and refers to a system of numbering amino acid residues which are more variable than other amino acid residues (e.g., hypervariable) in the heavy and light chain regions of immunoglobulins (Kabat, et al., (1971) *Ann. NY Acad. Sci.* 190:382-93; Kabat, et al., (1991) *Sequences of Proteins of Immunological Interest*, Fifth Edition, U.S. Department of Health and Human Services, NIH Publication No. 91-3242). For purposes of the present disclosure, unless otherwise specifically identified, the positioning of CDRs in the variable region of an antibody follows Kabat numbering or simply, "Kabat."

Ligand: As used herein, the term "ligand" refers to a molecule that specifically binds a receptor and causes a change in the receptor so as to effect a change in the activity of the receptor or a response in cell that expresses that receptor. In one embodiment, the term "ligand" refers to a molecule or complex thereof that can act as an agonist or antagonist of a receptor. As used herein, the term "ligand" encompasses natural and synthetic ligands. "Ligand" also encompasses small molecules, peptide mimetics of cytokines and antibodies. The complex of a ligand and receptor is termed a "ligand-receptor complex." A ligand may comprise one domain of a polyprotein or fusion protein (e.g., either domain of an antibody/ligand fusion protein).

Modulate: As used herein, the terms "modulate", "modulation" and the like refer to the ability of a test agent to cause a response, either positive or negative or directly or indirectly, in a system, including a biological system, or biochemical pathway. The term modulator includes both agonists (including partial agonists, full agonists and superagonists) and antagonists.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally, in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Parent Polypeptide: As used herein, the terms "parent polypeptide" or "parent protein" are used interchangeably to designate the source of a second polypeptide (e.g., a derivative, mutein or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g., glycosylated or PEGylated forms and/or fusion proteins comprising the parent polypeptide).

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Partial agonists can be used to activate receptors to give a desired submaximal response in a subject when inadequate amounts of the endogenous ligand are present, or they can reduce the overstimulation of receptors when excess amounts of the endogenous ligand are present. The maximum response (Emax) produced by a partial agonist is called its intrinsic activity and may be expressed on a percentage scale where a full agonist produced a 100% response. An partial agonist may have greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the reference polypeptide when evaluated at similar concentrations in a given assay system.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g., antigenic diphtheria or tetanus toxin or toxoid fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof. A course of action to prevent a disease, disorder or condition in a subject is typically applied in the context of a subject who is predisposed to developing a disease, disorder or condition due to genetic, experiential or environmental factors of developing a particular disease, disorder or condition. In certain instances, the terms "prevent", "preventing", "prevention" are also used to refer to the slowing of the progression of a disease, disorder or condition from an existing state to a more deleterious state.

Receptor: As used herein, the term "receptor" refers to a polypeptide having a domain that specifically binds a ligand that binding of the ligand results in a change to at least one biological property of the polypeptide. In some embodiments, the receptor is a cell membrane associated protein that comprises and extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of a cognate ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface receptor that is not associated with any intracellular signaling alone but upon ligand binding facilitates the formation of a heteromultimeric (including heterodimeric, heterotrimeric, etc.) or homomultimeric (including homodimeric, homotrimeric, homotetrameric, etc.) complex that results in a measurable biological effect in the cell such as activation of an intracellular signaling cascade (e.g., the Jak/STAT pathway). In some embodiments, a receptor is a membrane spanning single chain polypeptide comprising ECD, TM and ICD domains wherein the ECD, TM and ICD domains are derived from the same or differing naturally occurring receptor variants or synthetic functional equivalents thereof.

Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of cells present in culture as described in Crouch, et al. (1993) J. Immunol. Methods 160: 81-8 or using commercially available assays such as the CellTiter- Glo® 2.0 Cell Viability Assay or CellTiter-Glo® 3D Cell Viability kits commercially available from Promega Corporation, Madison WI 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art. For example, STAT5 phosphorylation may be measured using flow cytometric techniques as described in Horta, et al. supra., Garcia, et al., supra, or commercially available kits such as the Phospho-STAT5 (Tyr694) kit (commercially available from Perkin-Elmer, Waltham MA as Part Number 64AT5PEG) in performed in substantial accordance with the instructions provided by the manufacturer.

Significantly Reduced Binding: As used herein, the term "exhibits significantly reduced binding" is used with respect a variant of a first molecule (e.g., a ligand or antibody) which exhibits a significant reduction in the affinity for a second molecule (e.g., receptor or antigen) relative the parent form of the first molecule. With respect to antibody variants, an antibody variant "exhibits significantly reduced binding" if the affinity of the variant antibody for an antigen if the variant binds to the native form of the receptor with and affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent antibody from which the variant was derived. Similarly, with respect to variant ligands, a variant ligand "exhibits significantly reduced binding" if the affinity of the variant ligand binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived. Similarly, with respect to variant receptors, a variant ligand "exhibits significantly reduced binding" if the affinity of the variant receptors binds to a with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent receptor from which the variant receptor was derived.

Small Molecule(s): The term "small molecules" refers to chemical compounds (typically pharmaceutically active compounds) having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. The term "small molecule" is a term well understood to those of ordinary skill in the pharmaceutical arts and is typically used to distinguish organic chemical compounds from biologics.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair has the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant ($K_D$) between antibody and the antigen is lesser than about $10^{-6}$ M, alternatively lesser than about $10^{-8}$ M, alternatively lesser than about $10^{-10}$ M, alternatively lesser than about $10^{-11}$ M, lesser than about $10^{-12}$ M as determined by, e.g., Scatchard analysis (Munsen, et al. (1980) Analyt. Biochem. 107:220-239). In one embodiment where the ligand is an ILR binding sdAb and the receptor comprises an ILR, the ILR binding sdAb specifically binds if the equilibrium dissociation constant ($K_D$) of the ILR binding sdAb/ILR ECD is lesser than about $10^{-5}$M, alternatively lesser than about $10^{-6}$ M, alternatively lesser than about $10^{-7}$M, alternatively lesser than about $10^{-8}$M, alternatively lesser than about $10^{-9}$ M, alternatively lesser than about $10^{-10}$ M, or alternatively lesser than about $10^{-11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8+, Biacore S200, Biacore T200 (GE Healthcare Bio-Sciences, 100 Results Way, Marlborough MA 01752). In some embodiments, the present disclosure provides molecules (e.g., ILR binding sdAbs) that specifically bind to the hILR. As used herein, the binding affinity of an ILR binding molecule for the ILR, the binding affinity may be determined and/or quantified by surface plasmon resonance ("SPR"). In evaluating binding affinity of an ILR binding molecule for the ILR, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough MA as catalog number BR100407), as anti-His tag antibodies (e.g. anti-histidine CM5 chips commercially available from Cytiva, Marlborough MA), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising poly-histidine sequence (e.g., 6×His (SEQ ID NO: 165) or 8×His (SEQ ID NO: 166)) for retention on a chip conjugated with NTA. In some embodiments, the ILR binding molecule may be immobilized on the chip and ILR (or ECD fragment thereof) be provided in the mobile phase. Alternatively, the ILR (or ECD fragment thereof) may be immobilized on the chip and the ILR binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of ILR binding molecule for ILR using SPR, the ILR binding molecule may be derivatized by the C-terminal addition of a poly-His sequence (e.g., 6×His (SEQ ID NO: 165) or 8×His (SEQ ID NO: 166)) and immobilized on the NTA derivatized sensor chip and the ILR receptor subunit for which the ILR VHH's binding affinity is being evaluated is provided in the mobile phase. The means for incorporation of a poly-His sequence into the C-terminus of the ILR binding molecule produced by recombinant DNA technology is well known to those of skill in the relevant art of biotechnology. In some embodiments, the binding affinity of ILR binding molecule for an ILR comprises using SPR substantially in accordance with the teaching of the Examples.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95% of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95% of the total content of the composition.

Suffering From: As used herein, the term "suffering from" refers to a determination made by a physician with respect to a subject based on the available objective or subjective information accepted in the field for the identification of a disease, disorder or condition including but not limited to X-ray, CT-scans, conventional laboratory diagnostic tests (e.g., blood count, etc.), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

T-cell: As used herein the term "T-cell" or "T cell" is used in its conventional sense to refer to a lymphocytes that differentiates in the thymus, possess specific cell-surface antigen receptors, and include some that control the initiation or suppression of cell-mediated and humoral immunity and others that lyse antigen-bearing cells. In some embodiments the T cell includes without limitation naïve CD8+ T cells, cytotoxic CD8+ T cells, naïve CD4+ T cells, helper T cells, e.g., $T_H1$, $T_H2$, $T_H9$, $T_H11$, $T_H22$, $T_{FH}$; regulatory T cells, e.g., TRI, Tregs, inducible Tregs; memory T cells, e.g., central memory T cells, effector memory T cells, NKT cells, tumor infiltrating lymphocytes (TILs) and engineered variants of such T-cells including but not limited to CAR-T cells, recombinantly modified TILs and TCR-engineered cells. In some embodiments the T cell is a T cell expressing the IFNgR2 isoform referred to interchangeably as IFNgR2 cell, IFNgR2+ cell, IFNgR2 T cell, or IFNgR2+ T cell).

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Therapeutically Effective Amount: As used herein to the phrase "therapeutically effective amount" refers to the quantity of an agent when administered to a subject, either alone or as part of a pharmaceutical composition or treatment regimen, in a single dose or as part of a series of doses, provides a positive effect on any quantitative or qualitative symptom, aspect, or characteristic of a disease, disorder or condition. A therapeutically effective amount can be ascertained by measuring relevant physiological effects, and it may be adjusted in connection with a dosing regimen and in response to diagnostic analysis of the subject's condition. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, biomarkers (such as inflammatory cytokines, IFN-γ, granzyme, and the like), reduction in serum tumor markers, improvement in Response Evaluation Criteria In Solid Tumors (RECIST), improvement in Immune-Related Response Criteria (irRC), increase in duration of survival, extended duration of progression free survival, extension of the time to progression, increased time to treatment failure, extended duration of event free survival, extension of time to next treatment, improvement objective response rate, improvement in the duration of response, reduction of tumor burden, complete response, partial response, stable disease, and the like that that are relied upon by clinicians in the field for the assessment of an improvement in the condition of the subject in response to administration of an agent. In one embodiment, a therapeutically effective amount is an amount of an agent when used alone or in combination with another agent provides an provides a positive effect on any quantitative or qualitative symptom, aspect, or characteristic of a disease, disorder or condition and does not result in non-reversible serious adverse events in the course of administration of the agent to the mammalian subject.

Transmembrane Domain: The term “transmembrane domain” or “TM” refers to a polypeptide domain of a membrane spanning polypeptide (e.g., a transmembrane receptor) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treat: The terms “treat”, “treating”, treatment” and the like refer to a course of action (such as contacting the subject with pharmaceutical composition comprising a IFNgR2 binding sdAb alone or in combination with a supplementary agent) that is initiated with respect to a subject in response to a diagnosis that the subject is suffering from a disease, disorder or condition, or a symptom thereof, the course of action being initiated so as to eliminate, reduce, suppress, mitigate, or ameliorate, either temporarily or permanently, at least one of: (a) the underlying causes of such disease, disorder, or condition afflicting a subject; and/or (b) at least one of the symptoms associated with such disease, disorder, or condition. In some embodiments, treating includes a course of action taken with respect to a subject suffering from a disease where the course of action results in the inhibition (e.g., arrests the development of the disease, disorder or condition or ameliorates one or more symptoms associated therewith) of the disease in the subject.

Treg Cell or Regulatory T Cell. The terms “regulatory T cell”, “Treg cell”, or “Treg” are interchangeably herein to refers to a type of $CD4^+$ T cell that can suppress the responses of other T cells including but not limited to effector T cells ($T_{eff}$). Treg cells are typically characterized by expression of CD4 (CD4+), the CD25 subunit of the IL2 receptor (CD25+), and the transcription factor forkhead box P3 (FOXP3+) (Sakaguchi, Annu Rev Immunol 22, 531-62 (2004). In some instances, the term “conventional $CD4^+$ T cells” is used to distinguish non-Treg $CD4^+$ T cells from $CD4^+$ Tregs.

Variant: The terms “variant”, “protein variant” or “variant protein” or “variant polypeptide” are used interchangeably herein to refer to a polypeptide that differs from a parent polypeptide by virtue of at least one amino acid modification, substitution, or deletion. The parent polypeptide may be a naturally occurring or wild-type (WT) polypeptide or may be a modified version of a WT polypeptide. The term variant polypeptide may refer to the polypeptide itself, a composition comprising the polypeptide, or the nucleic acid sequence that encodes it. In some embodiments, the variant polypeptide comprises from about one to about ten, alternatively about one to about eight, alternatively about one to about seven, alternatively about one to about five, alternatively about one to about four, alternatively from about one to about three alternatively from one to two amino acid modifications, substitutions, or deletions, or alternatively a single amino acid amino acid modification, substitution, or deletion compared to the parent polypeptide. A variant may be at least about 99% identical, alternatively at least about 98% identical, alternatively at least about 97% identical, alternatively at least about 95% identical, or alternatively at least about 90% identical to the parent polypeptide from which the variant is derived.

Wild Type: By “wild type” or “WT” or “native” herein is meant an amino acid sequence or a nucleotide sequence that is found in nature, including allelic variations. A wild-type protein, polypeptide, antibody, immunoglobulin, IgG, etc. has an amino acid sequence or a nucleotide sequence that has not been modified by the hand of man.

IFNgR2

The IFNgR2 binding molecules of the present disclosure specifically bind to the extracellular domain of the IFNgR2.

Human IFNgR2

In one embodiment, specifically bind to the extracellular domain of the human IFNgR2 receptor subunit (hIFNgR2). hIFNgR2 is expressed as a 337 amino acid precursor comprising a 21 amino acid N-terminal signal sequence which is post-translationally cleaved to provide a 316 amino acid mature protein. The canonical full-length acid hIFNgR2 precursor (including the signal peptide) is a 337 amino acid polypeptide having the amino acid sequence:

```
                                            (SEQ ID NO: 1)
MRPTLLWSLLLLLGVFAAAAAAPPDPLSQLPAPQHPKIRLYNAEQVLSWE

PVALSNSTRPVVYQVQFKYTDSKWFTADIMSIGVNCTQITATECDFTAAS

PSAGFPMDFNVTLRLRAELGALHSAWVTMPWFQHYRNVTVGPPENIEVTP

GEGSLIIRFSSPFDIADTSTAFFCYYVVHYWEKGGIQQVKGPFRSNSISLD

NLKPSRVYCLQVQAQLLWNKSNIFRVGHLSNISCYETMADASTELQQVIL

ISVGTFSLLSVLAGACFFLVLKYRGLIKYWFHTPPSIPLQIEEYLKDPTQ

PILEALDKDSSPKDDVWDSVSIISFPEKEQEDVLQTL
```

For purposes of the present disclosure, the numbering of amino acid residues of the human IFNgR2 polypeptides as described herein is made in accordance with the numbering of this canonical sequence (UniProt Reference No. P38484, SEQ ID NO:1). Amino acids 1-21 of SEQ ID NO:1 are identified as the signal peptide of hIFNgR2, amino acids 22-247 of SEQ ID NO:1 are identified as the extracellular domain, amino acids 248-268 of SEQ ID NO:1 are identified as the transmembrane domain, and amino acids 269-337 of SEQ ID NO:1 are identified as the intracellular domain.

For the purposes of generating antibodies that bind to the ECD of IFNgR2, immunization may be performed with the extracellular domain of the hIFNgR2. The extracellular domain of hIFNgR2 is a 220 amino acid polypeptide of the sequence:

```
                                          (SEQ ID NO: 162)
SQLPAPQHPKIRLYNAEQVLSWEPVALSNSTRPVVYQVQFKYTDSKWFTA

DIMSIGVNCTQITATECDFTAASPSAGFPMDFNVTLRLRAELGALHSAWV

TMPWFQHYRNVTVGPPENIEVTPGEGSLIIRFSSPFDIADTSTAFFCYYV
```

-continued
HYWEKGGIQQVKGPFRSNSISLDNLKPSRVYCLQVQAQLLWNKSNIFRVG

HLSNISCYETMADASTELQQ.

Mouse IFNgR2

In one embodiment, specifically bind to the extracellular domain of the mouse or murine IFNgR2 receptor subunit (mIFNgR2). mIFNgR2 is expressed as a 332 amino acid precursor comprising a 19 amino acid N-terminal signal sequence which is post-translationally cleaved to provide a 313 amino acid mature protein. The canonical full-length acid mIFNgR2 precursor (including the 19 amino acid signal peptide) is a 332 amino acid polypeptide having the amino acid sequence:

(SEQ ID NO: 163)
MRPLPLWLPSLLLCGLGAAASSPDSFSQLAAPLNPRLHLYNDEQILTWEP

SPSSNDPRPVVYQVEYSFIDGSWHRLLEPNCTDITETKCDLTGGGRLKLF

PHPFTVFLRVRAKRGNLTSKWVGLEPFQHYENVTVGPPKNISVTPGKGSL

VIHFSPPFDVFHGATFQYLVHYWEKSETQQEQVEGPFKSNSIVLGNLKPY

RVYCLQTEAQLILKNKKIRPHGLLSNVSCHETTANASARLQQVILIPLGI

FALLLGLTGACFTLFLKYQSRVKYWFQAPPNIPEQIEEYLKDPDQFILEV

LDKDGSPKEDSWDSVSIISSPEKERDDVLQTP

For purposes of the present disclosure, the numbering of amino acid residues of the mIFNgR2 polypeptides as described herein is made in accordance with the numbering of this canonical sequence (UniProt Reference No. Q63953, SEQ ID NO:163). Amino acids 1-19 of SEQ ID NO:163 are identified as the signal peptide of mIFNgR2, amino acids 20-243 of SEQ ID NO: 163 are identified as the extracellular domain, amino acids 244-266 of SEQ ID NO:163 are identified as the transmembrane domain, and amino acids 267-332 of SEQ ID NO:163 are identified as the intracellular domain.

For the purposes of generating antibodies that bind to the ECD of IFNgR2, immunization may be performed with the extracellular domain of the mIFNgR2. The extracellular domain of the mIFNgR2 receptor is a 229 amino acid polypeptide of the sequence:

(SEQ ID NO: 164)
ASSPDSFSQLAAPLNPRLHLYNDEQILTWEPSPSSNDPRPVVYQVEYSFI

DGSWHRLLEPNCTDITETKCDLTGGGRLKLFPHPFTVFLRVRAKRGNLTS

KWVGLEPFQHYENVTVGPPKNISVTPGKGSLVIHFSPPFDVFHGATFQYL

VHYWEKSETQQEQVEGPFKSNSIVLGNLKPYRVYCLQTEAQLILKNKKIR

PHGLLSNVSCHETTANASARLQQV

Experimental

The single domain antibodies of the present disclosure were obtained from camels by immunization with an extracellular domain of a IFNgR2 receptor. IFNgR2 VHH molecules of the present disclosure of the present disclosure were generated in substantial accordance with the teaching of the Examples. Briefly, a camel was sequentially immunized with the ECD of the human IFNgR2 over a period several weeks of by the subcutaneous an adjuvanted composition containing a recombinantly produced fusion proteins comprising the extracellular domain of the IFNgR2, the human IgG1 hinge domain and the human IgG1 heavy chain Fc. Following immunization, RNAs extracted from a blood sample of appropriate size VHH-hinge-CH2-CH3 species were transcribed to generate DNA sequences, digested to identify the approximately 400 bp fragment comprising the nucleic acid sequence encoding the VHH domain was isolated. The isolated sequence was digested with restriction endonucleases to facilitate insertion into a phagemid vector for in frame with a sequence encoding a his-tag and transformed into *E. coli* to generate a phage library. Multiple rounds of biopanning of the phage library were conducted to identify VHHs that bound to the ECD of IFNgR2. Individual phage clones were isolated for periplasmic extract ELISA (PE-ELISA) in a 96-well plate format and selective binding confirmed by colorimetric determination. The IFNgR2 binding molecules that demonstrated specific binding to the IFNgR2 antigen were isolated and sequenced and sequences analyzed to identify VHH sequences, CDRs and identify unique VHH clonotypes. As used herein, the term "clonotypes" refers a collection of binding molecules that originate from the same B-cell progenitor cell, in particular collection of antigen binding molecules that belong to the same germline family, have the same CDR3 lengths, and have 70% or greater homology in CDR3 sequence. The VHH molecules demonstrating specific binding to the hIFNgR2 ECD antigen (anti-human IFNgR2 VHHs) and the CDRs isolated from such VHHs are provided in Table 1. Nucleic acid sequences encoding the VHHs of Table 1 are provide in Table 2.

In some instances, due to sequence or structural similarities between the extracellular domains of IFNgR2 receptors from various mammalian species, immunization with an antigen derived from a IFNgR2 of a first mammalian species (e.g., the hIFNgR2-ECD) may provide antibodies which specifically bind to IFNgR2 receptors of one or more additional mammalian species. Such antibodies are termed "cross reactive." For example, immunization of a camelid with a human derived antigen (e.g., the hIFNgR2-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR.

Consequently, the use of the term "human IFNgR2 VHH" or "hIFNgR2 VHH" merely denotes that the species of the IFNgR2 antigen used for immunization of the camelid from which the VHH was derived was the human IFNgR2 (e.g., the IFNgR2, ECD, SEQ ID NO:164 but should not be understood as limiting with respect to the specific binding affinity of the VHH for IFNgR2 molecules of other mammalian species. Similarly, the use of the term "mouse IFNgR2 VHH" or "mIFNgR2 VHH" merely denotes that the species of the IFNgR2 antigen used for immunization of the camelid from which the VHH was derived was the murine IFNgR2 (e.g., the mIFNgR2 ECD, SEQ ID NO:194) but should not be understood as limiting with respect to the specific binding affinity of the VHH for IFNgR2 molecules of other mammalian species.

The hIFNgR2 VHHs of Table 1 (SEQ ID NOS: 2-33) were evaluated for cross-reactivity with the mIFNgR2 by flow cytometry and were found to bind both the extracellular domain of hIFNgR2 (SEQ ID NO. 162) and the extracellular domain of mIFNgR2 (SEQ ID NO. 164). Consequently, the VHHs provided in Table 1 may be used in both murine and human applications avoiding the necessity of a surrogate anti-mIFNgR2 for anti-hIFNgR2 for in vivo models of efficacy, such as a mouse model of a human disease state.

IFNgR2 Binding Molecules and Single Domain Antibodies

In some embodiments, a IFNgR2 binding molecule of the present disclosure is a single domain antibody (sdAb). The present disclosure relates to IFNgR2 binding molecules comprising single domain antibodies (sdAbs) that specifically bind to the extracellular domain of the human IFNgR2 isoform (hIFNgR2) which are found on all IFNgR2-expressing cells.

A single-domain antibody (sdAb) is an antibody containing a single monomeric variable antibody domain. Like a full-length antibody, sdAbs are able to bind specifically to an antigenic determinant. hIFNgR2 binding VHH single-domain antibodies can be engineered from heavy chain antibodies isolated from Camelidae mammals (e.g., camels, llamas, dromedary, alpaca, and guanaco) immunized with the extracellular domain of hIFNgR2 or an immunologically active fragment thereof. Descriptions of sdAbs and VHHs can be found in, e.g., De Greve et al., (2019) Curr Opin Biotechnol. 61:96-101; Ciccarese, et al., (2019) Front Genet. 10:997: Chanier and Chames (2019) *Antibodies* (Basel) 8(1); and De Vlieger, et al. (2018) *Antibodies* (Basel) 8(1). Alternatively, hIFNgR2 single domain antibodies may be engineered from heavy chain antibodies isolated from the IgNAR heavy chain antibodies isolated from cartilaginous fishes immunized with the extracellular domain of hIFNgR2 or an immunologically active fragment thereof hIFNgR2 binding sdAbs may also be obtained by splitting the dimeric variable domains from immunoglobulin G (IgG) isotypes from other mammalian species including humans, rats, rabbits immunized with the extracellular domain of hIFNgR2 or an immunologically active fragment thereof. Although most research into sdAbs is currently based on heavy chain variable domains, sdAbs derived from light chains have also been shown to bind specifically to the target proteins comprising the antigenic immunization sequence. Moller et al., *J Biol Chem.* 285(49):38348-38361, 2010.

In some embodiments, the sdAb is a VHH. A VHH is a type of sdAb that has a single monomeric heavy chain variable antibody domain. Similar to a traditional antibody, a VHH is able to bind specifically to a specific antigen. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains.

The present disclosure provides IFNgR2 binding molecules comprising a polypeptide having at least 75%, alternatively 80%, alternatively 90%, alternatively 95%, alternatively 98%, or alternatively 99% or 100% identity to a polypeptide of any one of SEQ ID NOS:2-33.

Modified Forms of Single Domain Antibodies

CDR Grafted sdAbs

In some embodiments, the IFNgR2 binding sdAb of the present disclosure is a CDR grafted IFNgR2 binding sdAb. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. In some embodiments, the present disclosure provides a IFNgR2 binding molecule comprising a CDR grafted IFNgR2 binding sdAb, said CDR-grafted IFNgR2 binding sdAb comprising a set of CDRs1, 2, and 3 as shown in a row of the Table 1 above. In some embodiments, the present disclosure provides a IFNgR2 binding molecule comprising a CDR grafted IFNgR2 binding sdAb, said CDR-grafted IFNgR2 binding sdAb comprising a set of CDRs1, 2, and 3 as shown in a row of the Table 1 above.

Chimeric and Humanized sdAbs

Any framework region can be used with the CDRs as described herein. In some embodiments, the IFNgR2 binding sdAb is a chimeric sdAb, in which the CDRs are derived from one species (e.g., camel) and the framework and/or constant regions are derived from another species (e.g., human or mouse). In specific embodiments, the framework regions are human or humanized sequences. Thus, humanized IFNgR2 binding sdAbs derived from hIFNgR2 binding VHHs are considered within the scope of the present disclosure. The techniques for humanization of camelid single domain antibodies are well known in the art. See, e.g., Vincke, et al. (2009) *General Strategy to Humanize a Camelid Single-domain Antibody and Identification of a Universal Humanized Nanobody Scaffold* J. Biol. Chem. 284(5)3273-3284.

In some embodiments, a VHH described herein can be humanized to contain human framework regions. Examples of human germlines that could be used to create humanized VHHs include, but are not limited to, VH3-23 (e.g., UniProt ID: P01764), VH3-74 (e.g., UniProtID: A0A0B4J1X5), VH3-66 (e.g., UniProtID: A0A0C4DH42), VH3-30 (e.g., UniProt ID: P01768), VH3-11 (e.g., UniProt ID: P01762), and VH3-9 (e.g., UniProt ID: P01782).

Elimination of N-Linked Glycosylation Sites

In some embodiments, it is possible that an amino acid sequence (particularly a CDR sequence) of the hIFNgR2 binding sdAb may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the elimination of the Asn-X-Ser (N-X-S) N-linked glycosylation motif may be achieved by the incorporation of conservative amino acid substitution of the Asn (N) residue and/or Ser (S) residue of the Asn-X-Ser (N-X-S) N-linked glycosylation motif In some embodiments, the elimination of the Asn-X-Thr (N-X-T) N-linked glycosylation motif may be achieved by the incorporation of conservative amino acid substitution of the Asn (N) residue and/or Thr (T) residue of the Asn-X-Thr (N-X-T) N-linked glycosylation motif In some embodiments, elimination of the glycosylation site is not required when the IFNgR2 binding molecule is expressed in procaryotic host cells. Since procaryotic cells do not provide a mechanism for glycosylation of recombinant proteins, when employing a procaryotic expression system to produce a recombinant IFNgR2 binding sdAb the modification of the sequence to eliminate the N-linked glycosylation sites may be obviated.

IFNgR2 Binding Molecules Comprising Additional Agents

In some embodiments, a IFNgR2 binding molecule of the present disclosure a IFNgR2 single domain antibody (IFNgR2 sdAb) conjugated to one or more additional biologically active agents including but not limited to, therapeutic agents, chemically, optically or radioactively active agents, including combinations thereof. The conjugation of at least one such biologically, chemically, optically or radioactively active agent confer additional biological or chemical properties to IFNgR2 binding sdAb, the combination providing a IFNgR2 binding molecule possessing additional or alternative utilities.

For example, the additional agent may be a molecule selected from one or more of: immunomodulatory agents (e.g., immunogens); molecules that improve aqueous solubility (e.g., water soluble polymers and hydrophilic molecules such as sugars); carrier molecules that extend in vivo half-life (e.g., PEGylation, Fc fusions or acylation); generation of antibodies for use in detection assays (e.g., epitope tags), enhance ease of purification (e.g., chelating peptides such as poly-His tags); targeting domains that provide selective targeting IFNgR2 binding molecule to a particular cell or tissue type; therapeutic agents (e.g., therapeutic agents including small molecule or polypeptide agents); agents that visibility to optical or electromagnetic sensors (e.g., radionucleotides or fluorescent agents). In some embodiments, the linker is a cleavable linker or a non-cleavable linker. The use of a cleavable linker in a IFNgR2 binding molecule as contemplated herein facilitates the release of a therapeutic agent into the intracellular cytoplasm upon internalization of the IFNgR2 binding molecule. A non-cleavable linker would allow release upon digestion of the IFNgR2 binding molecule of or it could be used with an agent that does not require release from the antibody (e.g., an imaging agent).

In some embodiments, where the IFNgR2 binding molecule is an IFNgR2 sdAb in stable association with an additional agent joined via a linker. A linker is a covalent linkage between two elements of a IFNgR2 binding molecule (e.g., a hIFNgR2 binding VHH and PEG polymer). A linker can be a covalent bond, chemical linker or a peptide linker. Suitable linkers include "flexible linkers" which are generally of sufficient length to permit some movement between the IFNgR2 binding sdAb and the linked agent(s). Examples of chemical linkers include aryl acetylene, ethylene glycol oligomers containing 2-10 monomer units, diamines, diacids, amino acids, or combinations thereof. In some embodiments, the linker is a peptide linker. Suitable peptide linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Suitable peptide linkers are known in the art, and include, for example, peptide linkers containing flexible amino acid residues such as glycine and serine. Examples of flexible linkers include glycine polymers $(G)_n$, glycine-serine polymers, glycine-alanine polymers, alanine-serine polymers, and other flexible linkers. Glycine and glycine-serine polymers are relatively unstructured, and therefore can serve as a neutral tether between components. Further examples of flexible linkers include glycine polymers $(G)_n$, glycine-alanine polymers, alanine-serine polymers, glycine-serine polymers. Glycine and glycine-serine polymers are relatively unstructured, and therefore may serve as a neutral tether between components. A multimer (e.g., 1, 2, 3, 4, 5, 6, 7, 8, 9, 10, 10-20, 20-30, or 30-50) of such linker sequences may be linked together to provide flexible linkers that may be used to conjugate a heterologous amino acid sequence to IFNgR2 binding sdAbs disclosed herein. In some embodiments the linkers have the formula (GGGS)n (SEQ ID NO: 167), (GGGSG)n (SEQ ID NO: 168), or (GGSG)n (SEQ ID NO: 169), wherein n is an integer selected from 1, 2, 3, 4, 5, 6, 7, 8, 9 and 10.

Immunomodulatory Agents

In some embodiments, a IFNgR2 binding molecule of the present disclosure is operably linked to one or more an immunomodulatory agent (immunoconjugates). Immunomodulatory agents that may conjugated to the hIFNgR2 binding sdAb of the present disclosure include, but are not limited to, inactivated virus particles, inactivated bacterial toxins such as toxoid from diphtheria, tetanus, cholera, or leukotoxin molecules, inactivated bacteria and dendritic cells. Such immunoconjugates are useful in facilitating an immune response against the IFNgR2 or cells expressing the IFNgR2.

Flag Tags

In one embodiment, the present disclosure provides a IFNgR2 binding molecule operably linked to one or more an antigenic tags, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IFNgR2 binding sdAb polypeptide further comprises a C-terminal c-myc epitope tag.

Chelating Peptides

In one embodiment, the present disclosure provides a IFNgR2 binding molecule operably linked to one or more transition metal chelating polypeptide sequences. The conjugation of the IFNgR2 binding molecule to a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present IFNgR2 binding molecule are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present IFNgR2 binding molecule are polypeptides comprising 3-6 contiguous histidine residues (SEQ ID NO: 170) such as a six-histidine (His)6 peptide (SEQ ID NO: 165) and are frequently referred to in the art as "His-tags." In addition to providing a purification "handle" for the recombinant proteins, such chelating peptides may also facilitate the delivery of radioisotopes in substantial accordance with the teaching of Anderson, et al., U.S. Pat. No. 5,439,829 issued Aug. 8, 1995.

Carrier Molecules

In some embodiments the IFNgR2 binding sdAbs of the present disclosure may be conjugated to one or more carrier molecules. Carrier molecules are typically large, slowly metabolized macromolecules which provide for stabilization and/or extended duration of action in vivo to distinguish such molecules from conventional carrier molecules used in the preparation of pharmaceutical formulations as described below. Examples of in vivo carriers that may be incorporated into IFNgR2 binding molecules, but are not limited to: proteins (including but not limited to human serum albumin); fatty acids (acylation); polysaccharides (including but not limited to (N- and O-linked) sugars, sepharose, agarose, cellulose, or cellulose); polypeptdies amino acid copolymers; acylation, or polysialylation, an polyethylene glycol (PEG) polymers.

Water Soluble Polymers

In some embodiments, the IFNgR2 binding sdAb is conjugated to one or more water-soluble polymers. Examples of water soluble polymers useful in the practice of the present IFNgR2 binding molecule include polyethylene glycol (PEG), poly-propylene glycol (PPG), polysaccharides (polyvinylpyrrolidone, copolymers of ethylene glycol and propylene glycol, poly(oxyethylated polyol), poly-olefinic alcohol, polysaccharides, poly-alpha-hydroxy acid, polyvinyl alcohol (PVA), polyphosphazene, polyoxazolines (POZ), poly(N-acryloylmorpholine), or a combination thereof.

Polyethylene Glycol

In one embodiment, the carrier molecule is a polyethylene glycol ("PEG") polymer. Conjugation of PEG polymers to proteins (PEGylation) is a well-established method for the extension of serum half-life of biological agents. The PEGylated polypeptide may be further referred to as monopegylated, dipegylated, tripegylated (and so forth) to denote a polypeptide comprising one, two, three (or more) PEG moieties attached to the polypeptide, respectively. In some embodiments, the PEG may be covalently attached directly to the sdAb (e.g., through a lysine side chain, sulfhydryl group of a cysteine or N-terminal amine) or optionally employ a linker between the PEG and the sdAb. In some embodiments, a IFNgR2 binding molecule comprises more than one PEG molecules each of which is attached to a different amino acid residue. In some embodiments, the sdAb may be modified by the incorporation of non-natural amino acids with non-naturally occurring amino acid side chains to facilitate site specific PEGylation. In other embodiments, cysteine residues may be substituted at one or more positions within the sdAb to facilitate site-specific PEGylation via the cysteine sulfhydryl side chain.

In some instances, the IFNgR2 binding molecules of the present disclosure possess an N-terminal glutamine ("TQ") residue. N-terminal glutamine residues have been observed to spontaneously cyclyize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IFNgR2 binding molecules of the present disclosure, particularly when aldehyde chemistry is to be employed, the IFNgR2 binding molecules possessing an amino acid at position 1 (e.g., 1Q) are substituted at position 1 with an alternative amino acid or are deleted at position 1 (e.g., des-TQ). In some embodiments, the IFNgR2 binding molecules of the present disclosure comprise an amino acid substitution selected from the group Q1E and Q1D.

PEGs suitable for conjugation to a polypeptide sequence are generally soluble in water at room temperature, and have the general formula $$R(O-CH_2-CH_2)_nO-R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

A molecular weight of the PEG used in a IFNgR2 binding molecule is not restricted to any particular range. The PEG component of a IFNgR2 binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the IFNgR2 binding molecule, the PEG is a 40 kD branched PEG comprising two 20 kD arms.

The present disclosure also contemplates a IFNgR2 binding molecule comprising more than one PEG moiety wherein the PEGs have different sizes values, and thus the various different PEGs are present in specific ratios. For example, in the preparation of a PEGylated IFNgR2 binding molecule, some compositions comprise a mixture of mono-, di-, tri-, and quadra-PEGylated sdAb conjugates. In some compositions, the percentage of mono-PEGylated species is 18-25%, the percentage of di-PEGylated species is 50-66%, the percentage of tri-pegylated species is 12-16%, and the percentage of quadra-pegylated species up to 5%. Such complex compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

The PEG can be bound to a IFNgR2 binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the sdAb is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin, et al., PCT International Application No. PCT/US2018/045257 filed Aug. 3, 2018 and published Feb. 7, 2019 as International Publication Number WO 2019/028419A1.

The PEG moiety of the of a PEGylated IFNgR2 binding molecule may be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDa PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

Fc Fusions

In some embodiments, the carrier molecule is a Fc molecule or a monomeric subunit thereof. In some embodiments, the dimeric Fc molecule may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g., an IFNgR2 binding sdAb) on a first Fc monomer with a "knob" modification and a second polypeptide on the second Fc monomer possessing a "hole" modification to facilitate the expression of heterodimeric polypeptide conjugates.

Targeting Domains

In some embodiments, the IFNgR2 binding molecule is provided as a component of a multivalent (e.g., bivalent) fusion protein with a polypeptide sequence ("targeting domain") to facilitate selective binding to particular cell type or tissue expressing a cell surface molecule that specifically binds to such targeting domain, optionally incorporating a linker between the IFNgR2 binding sdAb sequence and the sequence of the targeting domain of the fusion protein.

In some embodiments of the IFNgR2 binding molecule, the IFNgR2 binding molecule may be targeted to a particular cell type cell by incorporation of a targeting domain into the structure of the IFNgR2 binding molecules. As used herein, the term targeting domain refers to a moiety that specifically binds to a molecule expressed on the surface of a target cell. The targeting domain may be any moiety that specifically binds to one or more cell surface molecules (e.g., T cell receptor) expressed on the surface of a target cell. In some embodiments, the target cell is a T cell. In some embodiments, the target cell is a IFNgR2$^+$ T cell.

In some embodiments, the targeting domain is a ligand for a receptor. In some embodiments, the targeting domain is a ligand for a receptor expressed on the surface of a T cell. In some embodiments, the ligand is a cytokine. In some embodiments, the cytokine includes but is not limited to the group consisting interleukins, interferons, and functional derivatives thereof. In some embodiments, the cytokine includes but is not limited to the group consisting IL2, IL3, IL4, IL7, IL9, IL12, IL15, IL18, IL21, IL22, IL23, IL27, IL28, IL34, and modified versions or fragments thereof that bind to their cognate ligand expressed on the surface of a T-cell. In some embodiments, the cytokine includes but is not limited to the group consisting of interferon alpha, interferon a2b, interferon gamma, or interferon lambda and modified versions or fragments thereof that bind to their cognate ligand expressed on the surface of a T-cell.

In another aspect, the present disclosure provides a multivalent binding molecule, the multivalent binding molecule comprising: (a) a IFNgR2 binding molecule and (b) a second binding molecule that specifically binds to the extracellular domain of a second cell surface molecule, wherein the IFNgR2 binding molecule and second binding molecule are operably linked, optionally through a chemical or polypeptide linker. In some embodiments, the IFNgR2 binding molecules of the present disclosure are useful in the preparation of the multivalent binding molecules described in Gonzalez, et al. PCT/US2018/021301 published as WO 2018/182935 A1 on Oct. 4, 2018. In accordance with the teaching of Gonzalez, the second binding molecule specifically binds to the extracellular domain of: (i) a component of cytokine receptor other than a receptor of which IFGgR2 forms a signaling complex in response to a natural ligand (e.g. IFNgR2) that activates the JAK/STAT pathway in the cell; (ii) a receptor tyrosine kinase; or (iii) a TNFR superfamily member. In some embodiments, the second surface molecule is a tyrosine kinase selected from EGFR, ErbB2, ErbB3, ErbB4, InsR, IGF1R, InsRR, PDGFRα, PDGFRβ, CSF1R/Fms, cKit, Flt-3/Flk2, VEGFR1, VEGFR2, VEGFR3, FGFR1, FGFR2, FGFR3, FGFR4, PTK7/CCK4, TrkA, TrkB, TrkC, Ror1, Ror2, MuSK, Met, Ron, Axl, Mer, Tyro3, Tie1, Tie2, EphA1-8, EphA10, EphB1-4, EphB6, Ret, Ryk, DDR1, DDR2, Ros, LMR1, LMR2, LMR3, ALK, LTK, SuRTK106/STYK1. In some embodiments, the second surface molecule is a TNFR superfamily member is selected from TNFR1 (TNFRSF1A), TNFR2 (TNFRSF1B; TNFRSF2), 41-BB (TNFRSF9); AITR (TNFRSF18); BCMA (TNFRSF17), CD27 (TNFRSF7), CD30 (TNFRSF8), CD40 (TNFRSF5), Death Receptor 1 (TNFRSF10C), Death Receptor-3 (TNFRSF25), Death Receptor 4 (TNFRSF10A), Death Receptor 5 (TNFRSF10B), Death Receptor-6 (TNFRSF21), Decoy Receptor-3 (TNFRSF6B), Decoy Receptor 2

(TNFRSF10D), EDAR, Fas (TNFRSF6), HVEM (TN-FRSF14), LTBR (TNFRSF3), OX40 (TNFRSF4), RANK (TNFRSF11A), TACI (TNFRSF13B), Troy (TNFRSF19), XEDAR (TNFRSF27), Osteoprotegerin (TNFRSF11B), TWEAK receptor (TNFRSF12A), BAFF Receptor (TNFRSF13C), NGF receptor (TNFRSF16).

In some embodiments, the targeting domain of the IFNgR2 binding molecule is an antibody (as defined hereinabove to include molecules such as VHHs, scFvs, etc.) Examples of antibodies that may incorporated as a targeting domain of a IFNgR2 binding molecule include but are not limited to the group consisting of: anti-GD2 antibodies, anti-BCMA antibodies, anti-CD19 antibodies, anti-CD33 antibodies, anti-CD38 antibodies, anti-CD70 antibodies, anti-GD2 antibodies and IL3Ra2 antibodies, anti-CD19 antibodies, anti-mesothelin antibodies, anti-Her2 antibodies, anti-EpCam antibodies, anti-Muc antibodies, anti-ROR1 antibodies, anti-CD133 antibodies, anti-CEA antibodies, anti-PSMA antibodies, anti-EGRFRVIII antibodies, anti-PSCA antibodies, anti-GPC3 antibodies, anti-Pan-ErbB antibodies, and anti-FAP antibodies.

The antibody or antigen-binding fragment thereof can also be linked to another antibody to form, e.g., a bispecific or a multispecific antibody.

Labels

In some embodiments, IFNgR2 binding molecules of the present disclosure are operably linked to a label. In some embodiments, the label is conjugated to the IFNgR2 binding molecule to facilitate use as imaging agent, diagnostic agent, or for use in cell sorting procedures. The term labels includes but is not limited to fluorescent labels, a biologically active enzyme labels, a radioisotopes (e.g., a radioactive ions), a nuclear magnetic resonance active labels, a luminescent labels, or a magnetic compound. In one embodiment a IFNgR2 binding sdAb (e.g., a IFNgR2 binding VHH) molecule in stable association (e.g., covalent, coordinate covalent) with an imaging labels. The term imaging labels is used to describe any of a variety of compounds a signature that facilitates identification, tracing and/or localization of the IFNgR2 binding sdAb (or its metabolites) using diagnostic procedures. Examples of imaging labels include, but are not limited to, fluorescent compounds, radioactive compounds, and compounds opaque to imaging methods (e.g., X-ray, ultrasound). Examples of radioactive compounds useful as imaging label include but are not limited to Technetium-99m ($^{99m}$Tc), Indium-111 ($^{111}$In), Iodine-131 ($^{131}$I), Iodine-123 ($^{123}$I), Iodine-125 ($^{125}$I), Gallium-67 ($^{67}$Ga), and Lutetium-177 ($^{177}$Lu), phosphorus ($^{32}$P), carbon ($^{14}$C), tritium ($^{3}$H), yttrium ($^{90}$Y), actinium ($^{225}$Ac), astatine ($^{211}$At), rhenium ($^{186}$Re), bismuth ($^{212}$Bi or $^{213}$Bi), and rhodium ($^{188}$Rh).

Therapeutic Agents

In some embodiments, IFNgR2 binding molecules of the present disclosure are operably linked to a therapeutic agent. Examples of therapeutic agents include therapeutic small molecule (e.g., chemotherapeutic agents) or biologic therapeutic agents including antibodies, cytoxic or cytostatic compounds, a radioisotope, molecules of plant, fungal, or bacterial origin, or biological proteins (e.g., protein toxins) or particles (e.g., nano-particles or recombinant viral particles, e.g., via a viral coat protein), therapeutic antibodies, chemotherapeutic agents, as described more fully herein.

In some embodiments, the therapeutic agent which may be incorporated into the IFNgR2 binding molecules of the present disclosure is short-range radiation emitters, including, for example, short-range, high-energy a-emitters. Examples of such radioisotope include an alpha-emitter, a beta-emitter, a gamma-emitter or a beta/gamma emitter. Radioisotopes useful as therapeutic agents include yttrium 90 ($^{90}$Y), lutetium-177 ($^{177}$Lu), actinium-225 ($^{225}$Ac), astatine-211 ($^{211}$At), rhenium-186 ($^{186}$Re), bismuth-212 ($^{212}$Bi), bismuth-213 ($^{213}$Bi), and rhodium-188 ($^{188}$Rh) Synthesis of IFNgR2 binding molecules:

In some embodiments, the IFNgR2 binding molecules of the present disclosure are polypeptides. However, in some embodiments, only a portion of the IFNgR2 binding molecule is a polypeptide, for example where the IFNgR2 binding molecule comprises a non-peptidyl domain (e.g., a PEG IFNgR2 binding sdAb conjugate, a radionucleotide IFNgR2 binding sdAb conjugate, or a small molecule IFNgR2 binding sdAb conjugate). The following provides guidance to enable the solid phase and recombinant synthesis of the polypeptide portions (domains) of IFNgR2 binding molecules of the present disclosure. In those embodiments where only a portion of the IFNgR2 binding molecule is a polypeptide, it will be understood that the peptidyl domain(s) of the IFNgR2 binding molecule are an intermediate in the process which may undergo further processing to complete the synthesis of the desired IFNgR2 binding molecules. The polypeptide domains of IFNgR2 binding molecules may be produced by conventional methodology for the construction of polypeptides including recombinant or solid phase syntheses as described in more detail below.

Chemical Synthesis

In addition to generating mutant polypeptides via expression of nucleic acid molecules that have been altered by recombinant molecular biological techniques, polypeptide domains of IFNgR2 binding molecules can be chemically synthesized. Chemically synthesized polypeptides are routinely generated by those of skill in the art. Chemical synthesis includes direct synthesis of a peptide by chemical means of the polypeptide domains of IFNgR2 binding molecules exhibiting the properties described. This method can incorporate both natural and unnatural amino acids at desired positions that facilitate linkage of particular molecules (e.g., PEG).

In some embodiments, the polypeptide domains of IFNgR2 binding molecules of the present disclosure may be prepared by chemical synthesis. The chemical synthesis of the polypeptide domains of IFNgR2 binding molecules may proceed via liquid-phase or solid-phase. Solid-phase peptide synthesis (SPPS) allows the incorporation of unnatural amino acids and/or peptide/protein backbone modification. Various forms of SPPS are available for synthesizing the polypeptide domains of IFNgR2 binding molecules of the present disclosure are known in the art (e.g., Ganesan A. (2006) Mini Rev. Med. Chem. 6:3-10; and Camarero J. A. et al., (2005) Protein Pept Lett. 12:723-8). In the course of chemical synthesis, the alpha functions and any reactive side chains may protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reversed-phase HPLC.

Recombinant Production

Alternatively, polypeptide domains of IFNgR2 binding molecules of the present disclosure may be produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation.

Synthesis of Nucleic Acid Sequences Encoding the IFNgR2 Binding Molecule

In some embodiments, the polypeptide domains of IFNgR2 binding molecule is produced by recombinant methods using a nucleic acid sequence encoding the polypeptide domains of IFNgR2 binding molecule (or fusion protein comprising the polypeptide domains of IFNgR2 binding molecule). The nucleic acid sequence encoding the desired polypeptide domains of IFNgR2 binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of the polypeptide domains of IFNgR2 binding molecule) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the polypeptide domains of IFNgR2 binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the polypeptide domains of the IFNgR2 binding molecule may be obtained from various commercial sources that provide custom synthesis of nucleic acid sequences. Amino acid sequence variants of the HUMAN IFNgR2 binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion can be made to arrive at the final construct, provided that the final construct possesses the desired biological activity as defined herein.

Methods for constructing a DNA sequence encoding the polypeptide domains of IFNgR2 binding molecule and expressing those sequences in a suitably transformed host include, but are not limited to, using a PCR-assisted mutagenesis technique. Mutations that consist of deletions or additions of amino acid residues to polypeptide domains of IFNgR2 binding molecule can also be made with standard recombinant techniques. In the event of a deletion or addition, the nucleic acid molecule encoding polypeptide domains of IFNgR2 binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A polypeptide domain of IFNgR2 binding molecules of the present disclosure may be produced recombinantly not only directly, but also as a fusion polypeptide with a heterologous polypeptide, e.g., a signal sequence or other polypeptide having a specific cleavage site at the N-terminus or C-terminus of the mature IFNgR2 binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the IFNgR2 binding molecule (i.e. the human IFNgR2 signal sequence). The inclusion of a signal sequence depends on whether it is desired to secrete the IFNgR2 binding molecule from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type IL-2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as Saccharomyces cerevisiae, the alpha mating factor secretion signal sequence may be employed to achieve extracellular secretion of the IFNgR2 binding molecule into the culture medium as described in Singh, U.S. Pat. No. 7,198,919 B1.

In the event the polypeptide domain of IFNgR2 binding molecules to be expressed is to be expressed as a chimera (e.g., a fusion protein comprising a IFNgR2 binding molecule and a heterologous polypeptide sequence), the chimeric protein can be encoded by a hybrid nucleic acid molecule comprising a first sequence that encodes all or part of the polypeptide domains of IFNgR2 binding molecule and a second sequence that encodes all or part of the heterologous polypeptide. For example, polypeptide domains of IFNgR2 binding molecules described herein may be fused to a hexa-histidine tag (SEQ ID NO: 165) to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the polypeptide domains of IFNgR2 binding molecule. For example, the N-terminus may be linked to a targeting domain and the C-terminus linked to a hexa-histidine tag (SEQ ID NO: 165) purification handle.

The complete amino acid sequence of the polypeptide domain of IFNgR2 binding molecule (or fusion/chimera) to be expressed can be used to construct a back-translated gene. A DNA oligomer containing a nucleotide sequence coding for the polypeptide domain of IFNgR2 binding molecules can be synthesized. For example, several small oligonucleotides coding for portions of the desired polypeptide can be synthesized and then ligated. The individual oligonucleotides typically contain 5' or 3' overhangs for complementary assembly.

In some embodiments, the nucleic acid sequence encoding the polypeptide domain of the IFNgR2 binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g., Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors

Once assembled (by synthesis, site-directed mutagenesis or another method), the nucleic acid sequence encoding polypeptide domains of IFNgR2 binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors. To facilitate efficient expression of the recombinant polypeptide, the nucleic acid sequence encoding the polypeptide sequence to be expressed is operably linked to transcriptional and translational regulatory control sequences that are functional in the chosen expression host.

Expression vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors for polypeptide domain of IFNgR2 binding molecules of the present disclosure contain a regulatory sequence that is recognized by the host organism and is operably linked to nucleic acid sequence encoding the polypeptide domains of IFNgR2 binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject IFNgR2 binding molecule, particularly as regards potential secondary structures.

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context. Proper assembly of the expression vector can be confirmed by nucleotide sequencing, restriction mapping, and expression of a biologically active polypeptide in a suitable host.

Host Cells

The present disclosure further provides prokaryotic or eukaryotic cells that contain and express a nucleic acid molecule that encodes a polypeptide domains of IFNgR2 binding molecule. A cell of the present disclosure is a transfected cell, i.e., a cell into which a nucleic acid molecule, for example a nucleic acid molecule encoding a polypeptide domains of IFNgR2 binding molecule, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this IFNgR2 binding molecule, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant polypeptide domains of IFNgR2 binding molecule or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerevisiae* include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The polypeptide domains of IFNgR2 binding molecule can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, the recombinant polypeptide domains of IFNgR2 binding molecule may be glycosylated or unglycosylated depending on the host organism used to produce the IFNgR2 binding molecule. If bacteria are chosen as the host then the polypeptide domains of IFNgR2 binding molecule produced will be aglycosylated. Eukaryotic cells, on the other hand, will glycosylate the recombinant polypeptide domains of IFNgR2 binding molecule.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection

The expression constructs can be introduced into host cells to thereby produce the recombinant polypeptide domains of IFNgR2 binding molecule disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning:

A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins

Recombinantly-produced IFNgR2 binding polypeptides can be recovered from the culture medium as a secreted polypeptide if a secretion leader sequence is employed. Alternatively, the IFNgR2 binding polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification

Various purification steps are known in the art and find use, e.g., affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g., gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The recombinant polypeptide domains of IFNgR2 binding molecule produced by the transformed host can be purified according to any suitable method. IFNgR2 binding molecules can be isolated from inclusion bodies generated in E. coli, or from conditioned medium from either mammalian or yeast cultures producing a given IFNgR2 binding molecule sing cation exchange, gel filtration, and or reverse phase liquid chromatography.

The substantially purified forms of the recombinant polypeptides can be used, e.g., as therapeutic agents, as described herein.

The biological activity of the recombinant polypeptide domains of IFNgR2 binding molecule produced in accordance with the foregoing can be confirmed by a IFNgR2 binding using procedures well known in the art including but not limited to competition ELISA, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493:323-343 (2009) with instrumentation commercially available from GE Healthcare Bio-Sciences such as the Biacore 8+, Biacore 5200, Biacore T200 (GE Healthcare Bio-Sciences, 100 Results Way, Marlborough MA 01752)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

Methods of Use

Inhibition of IFNgR2 Receptor Activity

In one embodiment, the present disclosure provides a method of modulating the activity of cells expressing the IFNgR2 by the administration of a composition comprising IFNgR2 binding molecule to a subject in an amount sufficient to interfere with the activity of receptors comprising the of IFNgR2. The present disclosure further provides a method of modulating the activity of cells expressing the IFNgR2 in a mixed population of cells comprising contacting said population of cells, in vivo and/or ex vivo, with a IFNgR2 binding molecule or complex of the present disclosure to in an amount sufficient to interfere with the activity of receptors comprising the IFNgR2.

Isolation, Enrichment or Depletion of IFNgR2+ Cells From a Biological Sample

In one embodiment, the present disclosure provides a method of use of the IFNgR2 binding molecules of the present disclosure useful in a process for in the isolation, enrichment or depletion of IFNgR2+ cells from a biological sample comprising IFNgR2+ cells. The biological sample may comprise cells of blood origin such as PBMC, T cells, B cells of cell culture origin or of tissue origin such as brain or bone marrow. Processes suitable for the isolation, enrichment or depletion of IFNgR2+ cells comprise centrifugation, filtration, magnetic cell sorting and fluorescent cell sorting by techniques well known in the art. The present disclosure further provides a method for the treatment of a subject suffering from a disease, disorder or condition by the administration of a therapeutically effective amount of a cell product enriched or depleted of IFNgR2+ cells through the use of a IFNgR2 binding molecule as described herein.

In one embodiment, the sorting procedure employs a IFNgR2 binding molecule comprising a fluorescent label for use in FACS isolation or depletion of IFNgR2+ cells from a sample. The fluorescent label may be attached to the sdAb of the IFNgR2 binding molecule directly (e.g., by chemical conjugation optionally employing a linker) or indirectly (e.g., by biotinylation of the sdAb and binding of the biotinylated antibody to a streptavidin fluorochrome conjugate). Such fluorescently labelled IFNgR2+ cells may be separated from a mixed cell population using conventional FACS technology.

In an alternative embodiment, the selection procedure employs IFNgR2 binding molecules of the present disclosure (e.g., a IFNgR2 binding VHH) conjugated to magnetic particles which provide magnetic labeling of the IFNgR2+ cells for use in magnetic cell separation procedures. In one embodiment the method comprises: (a) conjugation of one or more IFNgR2 binding molecule of the present disclosure (e.g., a IFNgR2 binding VHH) to a magnetic particle; (b) creating a mixture by contacting the biological sample with a quantity of the magnetic particles conjugated to IFNgR2 binding molecule; (c) subjecting to a magnetic field such that the magnetically labelled IFNgR2+ cells are retained; (d) removing the non-magnetically labelled cells from the mixture; and (e) removal of the magnetic field enabling isolation of the IFNgR2+ cells.

The cell selection procedure (e.g., FACS or magnetic separation) results in two products: (a) a population of cells depleted of IFNgR2+ cells and (b) a population of cells enriched for IFNgR2+ cells. Each of these populations may be further processed by convention procedures to identify particular IFNgR2+ or IFNgR2– cell subsets which may be useful in research, diagnostic or clinical applications. For example, isolation of specific IFNgR2$^+$ T cell subsets that also express one or more of CD4, CD8, CD19, CD25, and CD62L, further iterations of the using one or more antibodies that specifically bind to CD4, CD8, CD19, CD25, and CD62L antigens respectively by FACS or magnetic field separation by techniques well known in the art.

In one embodiment of the IFNgR2 binding molecule a humanized antibody or fragment thereof as disclosed herein may be used for depletion of IFNgR2-expressing cells from a biological sample comprising IFNgR2-expressing cells such peripheral blood or lymphoid tissue which may optionally be further processed for further isolation of IFNgR2+ naïve T cell subsets, isolation human IFNgR2+ memory T cells from a population of CD4+ or CD8+ cells, or isolation of human IFNgR2RA+naïve T cells from presorted CD4+ or CD8+ cells by depletion of IFNgR2+ cells. In one embodiment, the IFNgR2 binding molecule provides a method of generating a population of cells enriched for naïve Tregs from a biological sample, the method comprising depleting IFNgR2+ cells using a IFNgR2 binding molecule of the present disclosure as described above, optionally further comprising the steps of depleting CD8+ and/or CD19+ cells. The IFNgR2+ depleted cell population may optionally be further expanded in vitro for particular cell types to in the preparation of a cell product comprising a therapeutically effective amount of the IFNgR2+ depleted cell product which may be administered to a subject suffering from a disease, disorder or condition.

The IFNgR2+ enriched cell population may optionally be further expanded in vitro to in the preparation of a cell product comprising a therapeutically effective amount of the IFNgR2+ cells.

Inflammatory and Autoimmune Disorders

Disorders amenable to treatment with an IFNgR2 binding molecule (including pharmaceutically acceptable formulations comprising an IFNgR2 binding molecules and/or the nucleic acid molecules that encode them including recombinant viruses encoding such an IFNgR2 binding molecules) of the present disclosure include inflammatory or autoimmune diseases including but not limited to, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes including Type 1 or type 2 diabetes, inflammation, autoimmune disease, atopic diseases, paraneoplastic autoimmune diseases, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity Enthesopathy Arthropathy Syndrome), juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome (Seronegativity, Enthesopathy, Arthropathy Syndrome).

Other examples of proliferative and/or differentiative disorders amenable to treatment with IFNgR2 binding molecules (including pharmaceutically acceptable formulations comprising IFNgR2 binding molecules and/or the nucleic acid molecules that encode them including recombinant viruses encoding such IFNgR2 binding molecules) of the present disclosure include, but are not limited to, skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum *spinosum*, stratum *granulosum*, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of inflammatory or autoimmune skin disorders include psoriasis, psoriatic arthritis, dermatitis (eczema), for example, exfoliative dermatitis or atopic dermatitis, *pityriasis rubra* pilaris, *pityriasis* rosacea, parapsoriasis, *pityriasis* lichenoiders, lichen planus, lichen *nitidus*, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma *acuminatum*, and human papilloma viral (HPV) infections such as venereal warts; leukoplakia; lichen planus; and keratitis. The skin disorder can be dermatitis, e.g., atopic dermatitis or allergic dermatitis, or psoriasis.

The compositions of the present disclosure (including pharmaceutically acceptable formulations comprising IFNgR2 binding molecules and/or the nucleic acid molecules that encode them including recombinant viruses encoding such IFNgR2 binding molecules) can also be administered to a patient who is suffering from (or may suffer from) psoriasis or psoriatic disorders. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, plaque psoriasis, moderate to severe plaque psoriasis, psoriasis vulgaris, eruptive psoriasis, psoriatic erythroderma, generalized pustular psoriasis, annular pustular psoriasis, or localized pustular psoriasis.

Combination with Supplementary Therapeutic Agents

The present disclosure provides for the use of the IFNgR2 binding molecules of the present disclosure in combination with one or more additional active agents ("supplementary agents"). Such further combinations are referred to interchangeably as "supplementary combinations" or "supplementary combination therapy" and those therapeutic agents that are used in combination with IFNgR2 binding molecules of the present disclosure are referred to as "supplementary agents." As used herein, the term "supplementary agents" includes agents that can be administered or introduced separately, for example, formulated separately for separate administration (e.g., as may be provided in a kit) and/or therapies that can be administered or introduced in combination with the IFNgR2 binding molecules.

As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g., IFNgR2 binding molecule) is considered to be administered in combination with a second agent (e.g., a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g., nivolumab or pembrolizumab) are typically administered by IV infusion every two weeks or every three weeks while the IFNgR2 binding molecules of the present disclosure are typically administered more frequently, e.g., daily, BID, or weekly. However, the administration of the first agent (e.g., pembrolizumab) provides a therapeutic effect over an extended time and the administration of the second agent (e.g., an IFNgR2 binding molecule) provides its therapeutic effect while the therapeutic effect of the first agent remains ongoing such that the second agent is considered to be administered in combination with the first agent, even though the first agent may have been administered at a point in time significantly distant (e.g., days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IFNgR2 binding molecule and the supplementary agent (s) are administered or applied sequentially, e.g., where one agent is administered prior to one or more other agents. In other embodiments, the IFNgR2 binding molecule and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Supplemental Agents Useful in the Treatment of Inflammatory or Autoimmune Disorders In some embodiments, the method further comprises administering of the IFNgR2 binding molecule of the present disclosure in combination with one or more supplementary agents selected from the group consisting of a corticosteroid, a Janus kinase inhibitor, a calcineurin inhibitor, a mTor inhibitor, an IMDH inhibitor, a biologic, a vaccine, and a therapeutic antibody. In certain embodiments, the therapeutic antibody is an antibody that binds a protein selected from the group consisting of BLyS, CD11a, CD20, CD25, CD3, CD52, IgEIL12/IL23, IL17a, ILTB, IL4Rα, IL5, IL6R, integrin-α4β7, RANKL, TNFα, VEGF-A, and VLA-4.

In some embodiments, the supplementary agent is one or more agents selected from the group consisting of corticosteroids (including but not limited to prednisone, budesonide, prednilisone), Janus kinase inhibitors (including but not limited to tofacitinib (Xeljanz®), calcineurin inhibitors (including but not limited to cyclosporine and tacrolimus), mTor inhibitors (including but not limited to sirolimus and everolimus), IMDH inhibitors (including but not limited to azathioprine, leflunomide and mycophenolate), biologics such as abatcept (Orencia®) or etanercept (Enbrel®), and therapeutic antibodies.

Examples of therapeutic antibodies that may be administered as supplementary agents in combination with the IFNgR2 binding molecules of the present disclosure in the treatment of autoimmune disease include but are not limited to anti-CD25 antibodies (e.g. daclizumab and basiliximab), anti-VLA-4 antibodies (e.g. natalizumab), anti-CD52 antibodies (e.g. alemtuzumab), anti-CD20 antibodies (e.g. rituximab, ocrelizumab), anti-TNF antibodies (e.g. infliximab, and adalimumab), anti-IL6R antibodies (e.g. tocilizumab), anti-TNFα antibodies (e.g. adalimumab (Humira®), golimumab, and infliximab), anti-integrin-α4β7 antibodies (e.g. vedolizumab), anti-IL17a antibodies (e.g. brodalumab or secukinumab), anti-IL4Rα antibodies (e.g. dupilumab), anti-RANKL antibodies, IL6R antibodies, anti-IL1B antibodies (e.g. canakinumab), anti-CD1 Ta antibodies (e.g. efalizumab), anti-CD3 antibodies (e.g. muramonab), anti-IL5 antibodies (e.g. mepolizumab, reslizumab), anti-BLyS antibodies (e.g. belimumab); and anti-IL12/IL23 antibodies (e.g ustekinumab).

Many therapeutic antibodies have been approved for clinical use against autoimmune disease. Examples of antibodies approved by the United States Food and Drug Administration (FDA) for use in the treatment of autoimmune diseases in a subject suffering therefrom that may be administered as supplementary agents in combination with the IFNgR2 binding molecules of the present disclosure (and optionally additional supplementary agents) for the treatment of the indicated autoimmune disease are provided in Table 4 below:

TABLE 4

Antibodies Useful as Supplmentary Agents In the Treatment of Autoimmune and Inflammatory Disease

| Name | Target | Therapeutic Indication |
|---|---|---|
| efalizumab | CD11a | Psoriasis |
| belimumab | BLyS | Systemic lupus erythematosus |
| ocrelizumab | CD20 | Multiple sclerosis |
| rituximab | CD20 | Multiple sclerosis |
| basiliximab | CD25 | Transplantation rejection |
| daclizumab | CD25 | Transplantation rejection |
| muromonab | CD3 | Transplantation rejection |
| alemtuzumab | CD52 | Multiple sclerosis |
| omalizumab | IgE | Asthma |
| ustekinumab | IL12/IL23 | Plaque psoriasis |
| brodalumab | IL17a | Psoriasis, psoriatic arthritis, ankylosing spondylitis |
| secukinumab | IL17a | Psoriasis, psoriatic arthritis, ankylosing spondylitis |
| ixekizumab | IL17a | Psoriasis, psoriatic arthritis, ankylosing spondylitis |
| canakinumab | IL1β | Cryopyrin-associated periodic syndrome, tumor necrosis factor receptor associated periodic syndrome, hyperimmunoglobulin D syndrome, mevalonate kinase deficiency, familial Mediterranean fever, rheumatoid arthritis |
| dupilumab | IL4Rα | Asthma, dermatitis |
| mepolizumab | IL5 | Asthma |
| reslizumab | IL5 | Asthma |
| tocilizumab | IL6R | Rheumatoid arthritis |
| vedolizumab | Integrin-α4β7 | Ulcerative colitis, Crohn's disease |
| denosumab | RANKL | Osteoporosis |
| certolizumab | TNFa | Chron's disease, rheumatoid arthritis |
| golimumab | TNFa | Rheumatoid arthritis, psoriatic arthritis, ankylosing spondylitis |
| adalimumab | TNFα | Rheumatoid arthritis, juvenile idiopathic arthritis, psoriatic arthritis ankylosing spondylitis, Crohn's disease, plaque psoriasis |
| infliximab | TNFα | Crohn's disease, ulcerative colitis, rheumatoid arthritis, ankylosing spondylitis, psoriatic arthritis, plaque psoriasis |
| ranibizumab | VEGF-A | Neovascular age-related macular degeneration, macular edema |
| natalizumab | VLA-4 | Multiple sclerosis, relapsing rultiple sclerosis, Crohn's disease |

The foregoing antibodies of Table 4 useful as supplementary agents in the practice of the methods of the present disclosure may be administered alone or in the form of any antibody drug conjugate (ADC) comprising the antibody, linker, and one or more drugs (e.g. 1, 2, 3, 4, 5, 6, 7, or 8 drugs) or in modified form (e.g. PEGylated).

Formulations

The present disclosure further provides pharmaceutically acceptable formulations of the IFNgR2 binding molecules of the present disclosure. The preferred formulation depends on the intended mode of administration and therapeutic application. Pharmaceutical dosage forms of the IFNgR2 binding molecules described herein comprise physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, polymeric amino acids, amino acid copolymers, and lipid aggregates (such as oil droplets or liposomes).

The pharmaceutical compositions may also comprise pharmaceutically-acceptable, non-toxic carriers, excipients, stabilizers, or diluents, which are defined as vehicles commonly used to formulate pharmaceutical compositions for animal or human administration. The diluent is selected so as not to affect the biological activity of the combination. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Formulations to be used for in vivo administration are typically sterile. Sterilization of the compositions of the present disclosure may readily accomplished by filtration through sterile filtration membranes.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (Langer, *Science* 249: 1527, 1990 and Hanes, *Advanced Drug Delivery Reviews* 28: 97-119, 1997). The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Vector Delivery of Polypeptide IFNgR2 Binding Molecules

In those embodiments where the IFNgR2 binding molecule is a polypeptide, such IFNgR2 binding molecules may also be delivered to a subject through the Dosage The present disclosure further provides the administration of therapeutically or prophylactically effective dose of IFNgR2 binding molecule or a recombinant vector or cell comprising a nucleic acid sequence encoding a polypeptide IFNgR2 binding molecule to a subject suffering from or at risk of developing, respectively, a disease, disorder or condition. The dosage of the pharmaceutical composition comprising the IFNgR2 binding molecules, vector or cell depends on factors including the route of administration, the disease to be treated, and physical characteristics, e.g., age, weight, general health, of the subject. Typically, the amount of a IFNgR2 binding molecule contained within a single dose may be an amount that effectively prevents, delays, or treats the disease without inducing significant toxicity. A pharmaceutical composition of the disclosure may include a dosage of a IFNgR2 binding molecule described herein ranging from 0.01 to 500 mg/kg (e.g., from 0.01 to 450 mg, from 0.01 to 400 mg, from 0.01 to 350 mg, from 0.01 to 300 mg, from 0.01 to 250 mg, from 0.01 to 200 mg, from 0.01 to 150 mg, from 0.01 to 100 mg, from 0.01 to 50 mg, from 0.01 to 10 mg, from 0.01 to 1 mg, from 0.1 to 500 mg/kg, from 1 to 500 mg/kg, from 5 to 500 mg/kg, from 10 to 500 mg/kg, from 50 to 500 mg/kg, from 100 to 500 mg/kg, from 150 to 500 mg/kg, from 200 to 500 mg/kg, from 250 to 500 mg/kg, from 300 to 500 mg/kg, from 350 to 500 mg/kg, from 400 to 500 mg/kg, or from 450 to 500 mg/kg) and, in a more specific embodiment, about 1 to about 100 mg/kg (e.g., about 1 to about 90 mg/kg, about 1 to about 80 mg/kg, about 1 to about 70 mg/kg, about 1 to about 60 mg/kg, about 1 to about 50 mg/kg, about 1 to about 40 mg/kg, about 1 to about 30 mg/kg, about 1 to about 20 mg/kg, about 1 to about 10 mg/kg, about 10 to about 100 mg/kg, about 20 to about 100 mg/kg, about 30 to about 100 mg/kg, about 40 to about 100 mg/kg, about 50 to about 100 mg/kg, about 60 to about 100 mg/kg, about 70 to about 100 mg/kg, about 80 to about 100 mg/kg, or about 90 to about 100 mg/kg). In some embodiments, a pharmaceutical composition of the disclosure may include a dosage of a binding protein described herein ranging from 0.01 to 20 mg/kg (e.g., from 0.01 to 15 mg/kg, from 0.01 to 10 mg/kg, from 0.01 to 8 mg/kg, from 0.01 to 6 mg/kg, from 0.01 to 4 mg/kg, from 0.01 to 2 mg/kg, from 0.01 to 1 mg/kg, from 0.01 to 0.1 mg/kg, from 0.01 to 0.05 mg/kg, from 0.05 to 20 mg/kg, from 0.1 to 20 mg/kg, from 1 to 20 mg/kg, from 2 to 20 mg/kg, from 4 to 20 mg/kg, from 6 to 20 mg/kg, from 8 to 20 mg/kg, from 10 to 20 mg/kg, from 15 to 20 mg/kg). The dosage may be adapted by the physician in accordance with conventional factors such as the extent of the disease and different parameters of the subject.

A pharmaceutical composition containing a IFNgR2 binding molecule described herein can be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines. A course of therapy may be a single dose or in multiple doses over a period of time. In some embodiments, a single dose is used. In some embodiments, two or more split doses administered over a period of 1, 2, 3, 4, 5, 6, 7, 8, 9, 10, 11, 12, 13, 14, 21, 28, 30, 60, 90, 120 or 180 days are used. Each dose administered in such split dosing protocols may be the same in each administration or may be different. Multi-day dosing protocols over time periods may be provided by the skilled artisan (e.g., physician) monitoring the administration, taking into account the response of the subject to the treatment including adverse effects of the treatment and their modulation as discussed above.

For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In some embodiments the condition to be treated is a chronic condition (e.g., a chronic infection, i.e., an infection that is not cleared by the host immune system within a period of up to 1 week, 2 weeks, etc.). In some cases, chronic condition involve integration of pathogen genetic elements into the host genome, e.g., retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses. In such instances, the course of therapy may involve the administration of the IFNgR2 binding molecule over an extended period of time including continued administration in the substantial absence of the symptoms of the chronic condition to prevent recurrence of the chronic conditions or symptoms thereof.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Formulations

The present disclosure further provides pharmaceutically acceptable formulations of the IFNgR2 binding molecules of the present disclosure. The preferred formulation depends on the intended mode of administration and therapeutic application. Pharmaceutical dosage forms of the IFNgR2 binding molecules described herein comprise physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, polymeric amino acids, amino acid copolymers, and lipid aggregates (such as oil droplets or liposomes).

The pharmaceutical compositions may also comprise pharmaceutically-acceptable, non-toxic carriers, excipients, stabilizers, or diluents, which are defined as vehicles commonly used to formulate pharmaceutical compositions for animal or human administration. The diluent is selected so as not to affect the biological activity of the combination. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Formulations to be used for in vivo administration are typically sterile. Sterilization of the compositions of the present disclosure may readily accomplished by filtration through sterile filtration membranes.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (Langer, *Science* 249: 1527, 1990 and Hanes, *Advanced Drug Delivery Reviews* 28: 97-119, 1997). The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Vector Delivery of Polypeptide IFNgR2 Binding Molecules

In those embodiments where the IFNgR2 binding molecule is a polypeptide, such IFNgR2 binding molecules may also be delivered to a subject through the administration of a recombinant vectors comprising a nucleic acid sequence encoding the peptidyl IFNgR2 binding molecule operably linked to an expression control sequence in the cells of the tissues of the subject.

Expression vectors may be viral vectors or non-viral vectors. The term "nonviral vector" refers to an autonomously replicating, extrachromosomal circular DNA molecule, distinct from the normal genome and nonessential for cell survival under nonselective conditions capable of effecting the expression of an coding sequence in the target cell. Plasmids are examples of non-viral vectors. In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, magnetic fields (electroporation)

In one embodiment, a non-viral vector may be provided in a non-viral delivery system. Non-viral delivery systems are typically complexes to facilitate transduction of the target cell with a nucleic acid cargo wherein the nucleic acid is complexed with agents such as cationic lipids (DOTAP, DOTMA), surfactants, biologicals (gelatin, chitosan), metals (gold, magnetic iron) and synthetic polymers (PLG, PEI, PAMAM). Numerous embodiments of non-viral delivery systems are well known in the art including lipidic vector systems (Lee et al. (1997) Crit Rev Ther Drug Carrier Syst. 14:173-206); polymer coated liposomes (Marin et al., U.S. Pat. No. 5,213,804, issued May 25, 1993; Woodle, et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issuedNov. 26, 1996; Rose et al, U.S. Pat. No. 5,279,833, issued Jan. 18, 1994; Gebeyehu et al., U.S. Pat. No. 5,334,761, issued Aug. 2, 1994).

In another embodiment, the expression vector may be a viral vector. As used herein, the term viral vector is used in its conventional sense to refer to any of the obligate intracellular parasites having no protein-synthesizing or energy-generating mechanism and generally refers to any of the enveloped or non-enveloped animal viruses commonly employed to deliver exogenous transgenes to mammalian cells. A viral vector may be replication competent (e.g., substantially wild-type), conditionally replicating (recombinantly engineered to replicate under certain conditions) or replication deficient (substantially incapable of replication in the absence of a cell line capable of complementing the deleted functions of the virus). The viral vector can possess certain modifications to make it "specifically replicating," i.e. that it replicates preferentially in certain cell types or phenotypic cell states, e.g., cancerous. Viral vector systems useful in the practice of the instant IFNgR2 binding molecule include, for example, naturally occurring or recombinant viral vector systems. Examples of viruses useful in the practice of the present IFNgR2 binding molecule include recombinantly modified enveloped or non-enveloped DNA and RNA viruses. For example, viral vectors can be derived from the genome of human or bovine adenoviruses, vaccinia virus, lentivirus, herpes virus, adeno-associated virus, human immunodeficiency virus, sindbis virus, and retroviruses (including but not limited to Rous sarcoma virus), and hepatitis B virus. Typically, genes of interest are inserted into such vectors to allow packaging of the gene construct, typically with accompanying viral genomic sequences, followed by infection of a sensitive host cell resulting in expression of the gene of interest (e.g., a targeting antigen).

The expression vector may encode one or more polypeptides in addition to the targeting antigen. When expressing multiple polypeptides as in the practice of the present IFNgR2 binding molecule, each polypeptide may be operably linked to an expression control sequence (monocistronic) or multiple polypeptides may be encoded by a polycistronic construct where multiple polypeptides are expressed under the control of a single expression control sequence. In one embodiment, the expression vector encoding the targeting antigen may optionally further encode one or more immunological modulators. Examples of immunological modulators useful in the practice of the present IFNgR2 binding molecule include but are not limited to cytokines. Examples of such cytokines are interleukins including but not limited to one more or of IL-1, IL-2, IL-3, IL-4, IL-12, TNF-alpha, interferon alpha, interferon alpha-2b, interferon-beta, interferon-gamma, GM-CSF, MIP1-alpha, MIP1-beta, MIP3-alpha, TGF-beta and other suitable cytokines capable of modulating immune response. The expressed cytokines can be directed for intracellular expression or expressed with a signal sequence for extracellular presentation or secretion.

The expression vector may optionally provide an additional expression cassette comprising a nucleic acid sequence encoding a "rescue" gene. A "rescue gene" is a nucleic acid sequence, the expression of which renders the cell susceptible to killing by external factors or causes a toxic condition in the cell such that the cell is killed. Providing a rescue gene enables selective cell killing of transduced cells. Thus, the rescue gene provides an additional safety precaution when said constructs are incorporated into the cells of a mammalian subject to prevent undesirable spreading of transduced cells or the effects of replication competent vector systems. In one embodiment, the rescue gene is the thymidine kinase (TK) gene (see e.g., Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir.

Dosage

The present disclosure further provides the administration of therapeutically or prophylactically effective dose of IFNgR2 binding molecule or a recombinant vector or cell comprising a nucleic acid sequence encoding a polypeptide IFNgR2 binding molecule to a subject suffering from or at risk of developing, respectively, a disease, disorder or condition. The dosage of the pharmaceutical composition comprising the IFNgR2 binding molecules, vector or cell depends on factors including the route of administration, the disease to be treated, and physical characteristics, e.g., age, weight, general health, of the subject. Typically, the amount of a IFNgR2 binding molecule contained within a single dose may be an amount that effectively prevents, delays, or treats the disease without inducing significant toxicity. A pharmaceutical composition of the disclosure may include a dosage of a IFNgR2 binding molecule described herein ranging from 0.01 to 500 mg/kg (e.g., from 0.01 to 450 mg, from 0.01 to 400 mg, from 0.01 to 350 mg, from 0.01 to 300 mg, from 0.01 to 250 mg, from 0.01 to 200 mg, from 0.01 to 150 mg, from 0.01 to 100 mg, from 0.01 to 50 mg, from 0.01 to 10 mg, from 0.01 to 1 mg, from 0.1 to 500 mg/kg, from 1 to 500 mg/kg, from 5 to 500 mg/kg, from 10 to 500 mg/kg, from 50 to 500 mg/kg, from 100 to 500 mg/kg, from 150 to 500 mg/kg, from 200 to 500 mg/kg, from 250 to 500 mg/kg, from 300 to 500 mg/kg, from 350 to 500 mg/kg, from 400 to 500 mg/kg, or from 450 to 500 mg/kg) and, in a more specific embodiment, about 1 to about 100 mg/kg (e.g., about 1 to about 90 mg/kg, about 1 to about 80 mg/kg, about 1 to about 70 mg/kg, about 1 to about 60 mg/kg, about 1 to about 50 mg/kg, about 1 to about 40 mg/kg, about 1 to about 30 mg/kg, about 1 to about 20 mg/kg, about 1 to about 10 mg/kg, about 10 to about 100 mg/kg, about 20 to about 100 mg/kg, about 30 to about 100 mg/kg, about 40 to about 100 mg/kg, about 50 to about 100 mg/kg, about 60 to about 100 mg/kg, about 70 to about 100 mg/kg, about 80 to about 100 mg/kg, or about 90 to about 100 mg/kg). In some embodiments, a pharmaceutical composition of the disclosure may include a dosage of a binding protein described herein ranging from 0.01 to 20 mg/kg (e.g., from 0.01 to 15 mg/kg, from 0.01 to 10 mg/kg, from 0.01 to 8 mg/kg, from 0.01 to 6 mg/kg, from 0.01 to 4 mg/kg, from 0.01 to 2 mg/kg, from 0.01 to 1 mg/kg, from 0.01 to 0.1 mg/kg, from 0.01 to 0.05 mg/kg, from 0.05 to 20 mg/kg, from 0.1 to 20 mg/kg, from 1 to 20 mg/kg, from 2 to 20 mg/kg, from 4 to 20 mg/kg, from 6 to 20 mg/kg, from 8 to 20 mg/kg, from 10 to 20 mg/kg, from 15 to 20 mg/kg). The dosage may be adapted by the physician in accordance with conventional factors such as the extent of the disease and different parameters of the subject.

A pharmaceutical composition containing a IFNgR2 binding molecule described herein can be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines. A course of therapy may be a single dose or in multiple doses over a period of time. In some embodiments, a single dose is used. In some embodiments, two or more split doses administered over a period of 1, 2, 3, 4, 5, 6, 7, 8, 9, 10, 11, 12, 13, 14, 21, 28, 30, 60, 90, 120 or 180 days are used. Each dose administered in such split dosing protocols may be the same in each administration or may be different. Multi-day dosing protocols over time periods may be provided by the skilled artisan (e.g., physician) monitoring the administration, taking into account the response of the subject to the treatment including adverse effects of the treatment and their modulation as discussed above.

For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In some embodiments the condition to be treated is a chronic condition (e.g., a chronic infection, i.e., an infection that is not cleared by the host immune system within a period of up to 1 week, 2 weeks, etc.). In some cases, chronic condition involve integration of pathogen genetic elements into the host genome, e.g., retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses. In such instances, the course of therapy may involve the administration of the IFNgR2 binding molecule over an extended period of time including continued administration in the substantial absence of the symptoms of the chronic condition to prevent recurrence of the chronic conditions or symptoms thereof.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Routes of Administration

Administration of a IFNgR2 binding molecules described herein may be achieved through any of a variety of art recognized methods including but not limited to the topical, intravascular injection (including intravenous or intraarterial infusion), intradermal injection, subcutaneous injection, intramuscular injection, intraperitoneal injection, intracranial injection, intratumoral injection, intranodal injection, transdermal, transmucosal, iontophoretic delivery, intralymphatic injection (Senti and Kundig (2009) *Current Opinions in Allergy and Clinical Immunology* 9(6):537-543), intragastric infusion, intraprostatic injection, intravesical infusion (e.g., bladder), respiratory inhalers including nebulizers, intraocular injection, intraabdominal injection, intralesional injection, intraovarian injection, intracerebral infusion or injection, intracerebroventricular injection (ICVI), and the like. Administration to the subject may be achieved by intravenous, as a bolus or by continuous infusion over a period of time. Examples of parenteral routes of administration include, for example, intravenous, intradermal, subcutaneous, transdermal (topical), transmucosal, and rectal administration. The IFNgR2 binding molecule can be administered once, continuously, such as by continuous pump, or at periodic (e.g., daily, bi-weekly, monthly) intervals over a period of time can occur over the period of one week, two weeks, one month, two months, three months or more. Desired time intervals of multiple doses of the IFNgR2 binding molecule may be determined by one of skill in the art.

As described hereinabove, the compositions of the present disclosure may be used in combination with one or more additional therapeutically effective agents. As used herein, the term "in combination with" when used in reference to the administration of multiple agents to a subject refers to the administration of a first agent at least one additional (i.e. second, third, fourth, fifth, etc.) supplementary agent to a subject. For purposes of the present disclosure, one agent (e.g., a IFNgR2 binding molecule) is considered to be administered in combination with a supplementary agent if the biological effect resulting from the administration of the first agent persists in the subject at the time of administration of the supplementary agent such that the therapeutic effects of the first agent and second agent overlap. The administration of the first agent may provide a therapeutic effect over an extended time and the administration of the supplementary agent provides its therapeutic effect while the therapeutic effect of the first agent remains ongoing such that the supplementary agent is considered to be administered in combination with the first agent, even though the first agent may have been administered at a point in time significantly distant (e.g., days or weeks) from the time of administration of the supplementary agent. In one embodiment, one agent is considered to be administered in combination with a supplementary agent if the first and second agents are administered simultaneously (within 30 minutes of each other), contemporaneously or sequentially. In some embodiments, a first agent is deemed to be administered "contemporaneously" with a supplementary agent if first and supplementary agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a supplementary agent are co-formulated in single pharmaceutically acceptable formulation and the co-formulation is administered to a subject. In certain embodiments, first agent and the supplementary agent(s) are administered or applied sequentially, e.g., where one agent is administered prior to one or more other agents. In other embodiments, the first agent and the supplementary agent(s) are administered simultaneously, for example where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Kits

The present disclosure also contemplates kits comprising pharmaceutical compositions of IFNgR2 binding molecules. In some embodiments, the kit further comprises supplementary pharmaceutical compositions comprising supplementary agents as discussed above for use in combination therapy with IFNgR2 binding molecules. The kits are generally in the form of a physical structure housing various components, as described below, and can be utilized, for example, in practicing the methods described above. A kit may comprise a IFNgR2 binding molecule in the form of a pharmaceutical composition suitable for administration to a subject that is ready for use or in a form or requiring preparation for example, thawing, reconstitution or dilution prior to administration. When the IFNgR2 binding molecule is in a form that requires reconstitution by a user, the kit may also comprise a sterile container providing a reconstitution medium comprising buffers, pharmaceutically acceptable excipients, and the like. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IFNgR2 binding molecule or kit comprising) in compliance with governmental regulations (e.g., HIPAA) are provided.

EXAMPLES

The following examples are put forth so as to provide those of ordinary skill in the art with a complete disclosure and description of how to make and use the present IFNgR2 binding molecule, and are not intended to limit the scope of what the inventors regard as their IFNgR2 binding molecule nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for. Variations of the particularly described procedures employed may become apparent to individuals or skill in the art and it is expected that those skilled artisans may employ such variations as appropriate. Accordingly, it is intended that the IFNgR2 binding molecule be practiced otherwise than as specifically described herein, and that the invention includes all modifications and equivalents of the subject matter recited in the claims appended hereto as permitted by applicable law.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; pg=microgram; mg=milligram; g=gram; kg=kilogram; dl or dL=deciliter; pl or pL=microliter; ml or mL=milliliter; l or L=liter; pM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-hydroxysuccinimide; HSA=human serum albumin; MSA=mouse serum albumin; DMEM=Dulbeco's Modification of Eagle's Medium; GC=genome copy; EDTA=ethylenediaminetetraacetic acid; PBMCs=primary peripheral blood mononuclear cells; FBS=fetal bovine serum; FCS=fetal calf serum; HEPES=4-(2-hydroxyethyl)-1piperazineethanesulfonic acid; LPS=lipopolysaccharide; ATCC=American Type Culture Collection

Example 1. Immunization Protocol

The VHH was obtained by immunization of a llama with the extracellular domains of the hIFNgR2 as the antigen. A synthetic DNA sequence encoding the antigen was inserted into the pExSyn2.0 vector and transfected into the HEK293F mammalian cell host cell for expression. The antigen is expressed as a his tagged fusion protein which is purified using immobilized metal affinity chromatography. The antigen was diluted with 1×PBS (antigen total about 1 mg). The quality was estimated by SDS-PAGE to ensure the purity was sufficient (>90%) for immunization. The llama was acclimated at the facility for at least 7 days. At the start of the immunization protocol, 100 mL of blood was drawn to be used as a pre-bleed followed by boost with 150 to 500 ug of protein. Additional boosts were performed on days 14, 28, 42, and 56. 350 ml of blood was collected on day 63 for construction of the yeast sdAb library.

Example 2. Yeast Library Construction 350 ml of blood sample was collected from the llama seven days following the last injection in the immunization protocol. RNA was extracted from blood and transcribed to cDNA. The approximately 900 bp reverse transcribed sequences encoding the VH-CH1-hinge-CH2-CH3 constructs were isolated from the approximately desired 700 bp fragments encoding the VHH-hinge-CH2-CH3 species. The purified approximately 700 bp fragments were amplified by nested PCR. The amplified fragments were inserted into a NheI/BamHI digested pGAL 414 yeast display vector such that the sequence encoding the VHH was fused to the C-term of Aga2 with an N-term HA and C-term Myc tag. Yeast cells were transformed with digested vector and amplified insert. Transformants were enriched in SD-SCAA media lacking trptophan and uracil and stored at 4C till further use.

Example 3: Isolation of Antigen Specific VHHs sdAb were expressed on the surface of yeast (*S. cervisiae* ATCC strain EBY100) using standard protocols. Yeast were grown overnight at 30° C. in synthetic selective media SD-SCAA, then induced again overnight at 20° C. in SG-SCAA. SdAb expressing yeast were incubated with Alexa647 conjugated IFNGR1 from 30 minutes to 2 hours. Antigen binding yeast were sorted using a Sony sorter (SH800). After 3 rounds of selection, yeast cells were plated onto SD-SCAA plates lacking tryptophan and uracil. 192 colonies were picked from each campaign and grown overnight in 96 well plates at 30° C. in synthetic selective media SD-SCAA, then induced again overnight at 20° C. in SG-SCAA.

Example 4: Identification of Antibodies Exhibiting Specific Binding to IFNgR2

Upon completion of the biopanning of Example 3, three 96-well plates of individual phage clones were isolated in order to perform periplasmic extract ELISA (PE-ELISA) on IFNgR2 coated plates to identify positive VHH binders that selectively bound IFNgR2. A 96-well plate was coated with IFNgR2 and PBS under the same conditions. Next, wells were blocked at 37° C. for 1 h. Then, 100 µl of extracted antibodies was added to each well and incubated for 1 h. Subsequently, 100 µl of anti-tag polyclonal antibody conjugated to HRP was added to each well and incubated at 37° C. for 1 h. Plates were developed with TMB substrate. The reaction was stopped by the addition of H2SO4. Absorbance at 450 nm was read on a microtiter plate reader. Antibodies with absorbance of the antigen-coated well at least threefold greater than PBS-coated control were considered to provide specific binding to IFNgR2. Positive clones were sequenced, and sequences analyzed to identify unique clonotypes It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

The invention claimed is:

1. A IFNgR2 binding molecule that specifically binds to the extracellular domain of IFNgR2, wherein the IFNgR2 binding molecule comprises a single domain antibody (sdAb).

2. The IFNgR2 binding molecule of claim 1, wherein the sdAb comprises a complementary determining region 1 (CDR1), a CDR2, and a CDR3 as shown in a row of the table below:

| CDR1 | CDR2 | CDR3 |
| --- | --- | --- |
| RTFTSYAMN (SEQ ID NO: 34) | AISWSSGNTYVADSVKG (SEQ ID NO: 35) | TTIATMSDEYTY (SEQ ID NO: 36) |
| RTFSNYRMG (SEQ ID NO: 37) | AISRGGGTTLYADSVKG (SEQ ID NO: 38) | GDFSTTWDEYNY (SEQ ID NO: 39) |

-continued

| CDR1 | CDR2 | CDR3 |
|---|---|---|
| RTFSSYAMG (SEQ ID NO: 40) | AISRGGGSTDYADSVKG (SEQ ID NO: 41) | RAYSGRYYQFLEYDY (SEQ ID NO: 42) |
| RTFSSYAVA (SEQ ID NO: 43) | ALSRGGGSAYYTDSVKG (SEQ ID NO : 44) | RNYDGTYYQENQYNY (SEQ ID NO: 45) |
| RTFSTYAMG (SEQ ID NO: 46) | AISVNGGSTYYADSVTG (SEQ ID NO: 47) | RRPYPGSDFLTWASYDY (SEQ ID NO: 48) |
| RTFSYTTIG (SEQ ID NO: 49) | VISAGGGSRDYADALKG (SEQ ID NO: 50) | RRNTDTYTTTGDYDY (SEQ ID NO: 51) |
| GTISSLAMG (SEQ ID NO: 52) | AISWSGRSTYYVDSVKG (SEQ ID NO: 53) | GEDGHSEYDY (SEQ ID NO: 54) |
| RSFANYAMG (SEQ ID NO: 55) | AISRGGGSTWYADSVKG (SEQ ID NO: 56) | RSYSGSYTYSFGEYDY (SEQ ID NO: 57) |
| RAFSTYALG (SEQ ID NO: 58) | AISRGGGSTDYADSVKG (SEQ ID NO: 59) | RSYSSSYYYSQYEYDY (SEQ ID NO: 60) |
| RTFSSVAMA (SEQ ID NO: 61) | AISSGGGSTDYADSVKG (SEQ ID NO : 62) | RDYSSRRYYQSRYEYDL (SEQ ID NO: 63) |
| RTFRSYSMG (SEQ ID NO: 64) | AISWYSGTTYYADPVKG (SEQ ID NO: 65) | NEIATMESSNDY (SEQ ID NO: 66) |
| RPRTTYAMG (SEQ ID NO: 67) | AISKAGGSTYVADSAKG (SEQ ID NO: 68) | RAGFAAQIFEYDY (SEQ ID NO: 69) |
| RTFGTYAMG (SEQ ID NO: 70) | SIDRDGSMSYYADSVKG (SEQ ID NO: 71) | SRRAVISLQTVDY (SEQ ID NO: 72) |
| RTFSNYAMG (SEQ ID NO: 73) | AISWYSGNTYYADSVKG (SEQ ID NO: 74) | NQIATMISVGDY (SEQ ID NO: 75) |
| SIFRLNLMG (SEQ ID NO: 76) | HVGTTGNTAYADSVKG (SEQ ID NO: 77) | DRWGQFS (SEQ ID NO: 78) |
| RTFTGYAMG (SEQ ID NO: 79) | VITWSGATTYYSASVKG (SEQ ID NO: 80) | RIRDGVSPENPNEYGY (SEQ ID NO: 81) |
| RTVGYGMA (SEQ ID NO: 82) | AITWSGTSTYYPDSVKG (SEQ ID NO: 83) | GSRRVGVDVGGYDY (SEQ ID NO: 84) |
| RTFTFSTHNMG (SEQ ID NO: 85) | GIMWTSRASYADSVKG (SEQ ID NO : 86) | AWYGNSGASYDY (SEQ ID NO: 87) |
| RTFSGYNMG (SEQ ID NO: 88) | AIAWAGSRTYYTDSVKG (SEQ ID NO: 89) | HDETYYRLDRVDLYTH (SEQ ID NO: 90) |
| PFTRYAMG (SEQ ID NO: 91) | AISWSSGNTYYVDSVKG (SEQ ID NO: 92) | NEVATMSGPDDY (SEQ ID NO: 93) |
| GSFGRYTMG (SEQ ID NO: 94) | VISWSGTNTYYADSVKG (SEQ ID NO : 95) | RETYYSHWDERMEYDY (SEQ ID NO: 96) |
| SIDSSYYVS (SEQ ID NO: 97) | AINWGDSRTAYADSVKG (SEQ ID NO: 98) | RIGLGGPVVAAPTRYPY (SEQ ID NO : 99) |
| SILRFNVMS (SEQ ID NO: 100) | VITSGGSTNYADSVKG (SEQ ID NO : 101) | DESGQYY (SEQ ID NO: 102) |
| LTTSSAALA (SEQ ID NO: 103) | TITSGGGSTYYADSVKG (SEQ ID NO: 104) | RFYSTTYYYREHEYSD (SEQ ID NO: 105) |
| RTFGTSFGSLSMG (SEQ ID NO: 106) | AISRNIGRTYYADSVKD (SEQ ID NO: 107) | TNSYDDLRRSYAYDY (SEQ ID NO: 108) |
| RTFSSLAMA (SEQ ID NO: 109) | AISRSGGSTDYADSVKG (SEQ ID NO: 110) | RDYSTLQYYNEYEYSD (SEQ ID NO : 111) |
| PTFSTYAMA (SEQ ID NO: 112) | AITQSGRTTYYEDSVKG (SEQ ID NO: 113) | RDLWSDSPDDWRIYSF (SEQ ID NO : 114) |

-continued

| CDR1 | CDR2 | CDR3 |
|---|---|---|
| RTLHNFAMA (SEQ ID NO: 115) | AISKGGGSADYADSVKG (SEQ ID NO : 116) | NDLASYSDSSYTSTSRYDY (SEQ ID NO : 117) |
| RTFSSYAMA (SEQ ID NO: 118) | AISILGGSADYEDSVQG (SEQ ID NO : 119) | RRPAPSDSYWSSTSYAY (SEQ ID NO : 120) |
| RTFSSLAMA (SEQ ID NO: 121) | ATTILGGSADYGDPVKG (SEQ ID NO: 122) | RRPAPSDNYWSPASYAY (SEQ ID NO : 123) |
| RTFSSYAMA (SEQ ID NO: 124) | AITVSGASTYYADSVKG (SEQ ID NO: 125) | GGPGTIFPDYDY (SEQ ID NO : 126) |
| RTFSGYNMG (SEQ ID NO: 127) | AINWIGGATYYADSVKG (SEQ ID NO : 128) | YSEKFYSGKDYYTRDYDY (SEQ ID NO: 129). |

3. The IFNgR2 binding molecule of claim 1, wherein the sdAb has at least 95% identity to a polypeptide sequence of any one of SEQ ID NOS: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and 33.

4. The IFNgR2 binding molecule of claim 2, wherein the sdAb is humanized or otherwise comprises CDRs grafted onto a heterologous framework.

5. The IFNgR2 binding molecule of claim 1, further comprising a labeling agent, an imaging agent, and/or a therapeutic agent.

6. The IFNGR2 binding molecule of claim 1, wherein the sdAb comprises the CDR1, the CDR2, and the CDR3 of SEQ ID NOS:34, 35, and 36, respectively.

7. The IFNGR2 binding molecule of claim 6, wherein the sdAb has at least 95% identity to a polypeptide sequence of SEQ ID NO:2.

8. The IFNGR2 binding molecule of claim 1, wherein the sdAb comprises the CDR1, the CDR2, and the CDR3 of SEQ ID NOS:37, 38, and 39, respectively.

9. The IFNGR2 binding molecule of claim 8, wherein the sdAb has at least 95% identity to a polypeptide sequence of SEQ ID NO:3.

10. The IFNGR2 binding molecule of claim 1, wherein the sdAb comprises the CDR1, the CDR2, and the CDR3 of SEQ ID NOS:40, 41, and 42, respectively.

11. The IFNGR2 binding molecule of claim 10, wherein the sdAb has at least 95% identity to a polypeptide sequence of SEQ ID NO:4.

12. The IFNGR2 binding molecule of claim 1, wherein the sdAb comprises the CDR1, the CDR2, and the CDR3 of SEQ ID NOS:43, 44, and 45, respectively.

13. The IFNGR2 binding molecule of claim 12, wherein the sdAb has at least 95% identity to a polypeptide sequence of SEQ ID NO:5.

14. The IFNGR2 binding molecule of claim 1, wherein the sdAb comprises the CDR1, the CDR2, and the CDR3 of SEQ ID NOS:46, 47, and 48, respectively.

15. The IFNGR2 binding molecule of claim 14, wherein the sdAb has at least 95% identity to a polypeptide sequence of SEQ ID NO:6.

16. The IFNGR2 binding molecule of claim 1, wherein the sdAb comprises the CDR1, the CDR2, and the CDR3 of SEQ ID NOS:49, 50, and 51, respectively.

17. The IFNGR2 binding molecule of claim 16, wherein the sdAb has at least 95% identity to a polypeptide sequence of SEQ ID NO:7.

18. The IFNGR2 binding molecule of claim 1, wherein the sdAb comprises the CDR1, the CDR2, and the CDR3 of SEQ ID NOS:52, 53, and 54, respectively.

19. The IFNGR2 binding molecule of claim 18, wherein the sdAb has at least 95% identity to a polypeptide sequence of SEQ ID NO:8.

20. The IFNGR2 binding molecule of claim 1, wherein the sdAb comprises the CDR1, the CDR2, and the CDR3 of SEQ ID NOS:55, 56, and 57, respectively.

21. The IFNGR2 binding molecule of claim 20, wherein the sdAb has at least 95% identity to a polypeptide sequence of SEQ ID NO:9.

22. The IFNGR2 binding molecule of claim 1, wherein the sdAb comprises the CDR1, the CDR2, and the CDR3 of SEQ ID NOS:58, 59, and 60, respectively.

23. The IFNGR2 binding molecule of claim 22, wherein the sdAb has at least 95% identity to a polypeptide sequence of SEQ ID NO:10.

24. The IFNGR2 binding molecule of claim 1, wherein the sdAb comprises the CDR1, the CDR2, and the CDR3 of SEQ ID NOS:61, 62, and 63, respectively.

25. The IFNGR2 binding molecule of claim 24, wherein the sdAb has at least 95% identity to a polypeptide sequence of SEQ ID NO:11.

26. The IFNGR2 binding molecule of claim 1, wherein the sdAb comprises the CDR1, the CDR2, and the CDR3 of SEQ ID NOS:64, 65, and 66, respectively.

27. The IFNGR2 binding molecule of claim 26, wherein the sdAb has at least 95% identity to a polypeptide sequence of SEQ ID NO:12.

28. The IFNGR2 binding molecule of claim 1, wherein the sdAb comprises the CDR1, the CDR2, and the CDR3 of SEQ ID NOS:67, 68, and 69, respectively.

29. The IFNGR2 binding molecule of claim 28, wherein the sdAb has at least 95% identity to a polypeptide sequence of SEQ ID NO:13.

30. The IFNGR2 binding molecule of claim 1, wherein the sdAb comprises the CDR1, the CDR2, and the CDR3 of SEQ ID NOS:70, 71, and 72, respectively.

31. The IFNGR2 binding molecule of claim 30, wherein the sdAb has at least 95% identity to a polypeptide sequence of SEQ ID NO:14.

32. The IFNGR2 binding molecule of claim 1, wherein the sdAb comprises the CDR1, the CDR2, and the CDR3 of SEQ ID NOS:73, 74, and 75, respectively.

33. The IFNGR2 binding molecule of claim 32, wherein the sdAb has at least 95% identity to a polypeptide sequence of SEQ ID NO:15.

34. The IFNGR2 binding molecule of claim 1, wherein the sdAb comprises the CDR1, the CDR2, and the CDR3 of SEQ ID NOS:76, 77, and 78, respectively.

35. The IFNGR2 binding molecule of claim 34, wherein the sdAb has at least 95% identity to a polypeptide sequence of SEQ ID NO:16.

36. The IFNGR2 binding molecule of claim 1, wherein the sdAb comprises the CDR1, the CDR2, and the CDR3 of SEQ ID NOS:79, 80, and 81, respectively.

37. The IFNGR2 binding molecule of claim 36, wherein the sdAb has at least 95% identity to a polypeptide sequence of SEQ ID NO:17.

38. The IFNGR2 binding molecule of claim 1, wherein the sdAb comprises the CDR1, the CDR2, and the CDR3 of SEQ ID NOS:82, 83, and 84, respectively.

39. The IFNGR2 binding molecule of claim 38, wherein the sdAb has at least 95% identity to a polypeptide sequence of SEQ ID NO:18.

40. The IFNGR2 binding molecule of claim 1, wherein the sdAb comprises the CDR1, the CDR2, and the CDR3 of SEQ ID NOS:85, 86, and 87, respectively.

41. The IFNGR2 binding molecule of claim 40, wherein the sdAb has at least 95% identity to a polypeptide sequence of SEQ ID NO:19.

42. The IFNGR2 binding molecule of claim 1, wherein the sdAb comprises the CDR1, the CDR2, and the CDR3 of SEQ ID NOS:88, 89, and 90, respectively.

43. The IFNGR2 binding molecule of claim 42, wherein the sdAb has at least 95% identity to a polypeptide sequence of SEQ ID NO:20.

44. The IFNGR2 binding molecule of claim 1, wherein the sdAb comprises the CDR1, the CDR2, and the CDR3 of SEQ ID NOS:91, 92, and 93, respectively.

45. The IFNGR2 binding molecule of claim 44, wherein the sdAb has at least 95% identity to a polypeptide sequence of SEQ ID NO:21.

46. The IFNGR2 binding molecule of claim 1, wherein the sdAb comprises the CDR1, the CDR2, and the CDR3 of SEQ ID NOS:94, 95, and 96, respectively.

47. The IFNGR2 binding molecule of claim 46, wherein the sdAb has at least 95% identity to a polypeptide sequence of SEQ ID NO:22.

48. The IFNGR2 binding molecule of claim 1, wherein the sdAb comprises the CDR1, the CDR2, and the CDR3 of SEQ ID NOS:97, 98, and 99, respectively.

49. The IFNGR2 binding molecule of claim 48, wherein the sdAb has at least 95% identity to a polypeptide sequence of SEQ ID NO:23.

50. The IFNGR2 binding molecule of claim 1, wherein the sdAb comprises the CDR1, the CDR2, and the CDR3 of SEQ ID NOS:100, 101, and 102, respectively.

51. The IFNGR2 binding molecule of claim 50, wherein the sdAb has at least 95% identity to a polypeptide sequence of SEQ ID NO:24.

52. The IFNGR2 binding molecule of claim 1, wherein the sdAb comprises the CDR1, the CDR2, and the CDR3 of SEQ ID NOS:103, 104, and 105, respectively.

53. The IFNGR2 binding molecule of claim 52, wherein the sdAb has at least 95% identity to a polypeptide sequence of SEQ ID NO:25.

54. The IFNGR2 binding molecule of claim 1, wherein the sdAb comprises the CDR1, the CDR2, and the CDR3 of SEQ ID NOS:106, 107, and 108, respectively.

55. The IFNGR2 binding molecule of claim 54, wherein the sdAb has at least 95% identity to a polypeptide sequence of SEQ ID NO:26.

56. The IFNGR2 binding molecule of claim 1, wherein the sdAb comprises the CDR1, the CDR2, and the CDR3 of SEQ ID NOS:109, 110, and 111, respectively.

57. The IFNGR2 binding molecule of claim 56, wherein the sdAb has at least 95% identity to a polypeptide sequence of SEQ ID NO:27.

58. The IFNGR2 binding molecule of claim 1, wherein the sdAb comprises the CDR1, the CDR2, and the CDR3 of SEQ ID NOS:112, 113, and 114, respectively.

59. The IFNGR2 binding molecule of claim 58, wherein the sdAb has at least 95% identity to a polypeptide sequence of SEQ ID NO:28.

60. The IFNGR2 binding molecule of claim 1, wherein the sdAb comprises the CDR1, the CDR2, and the CDR3 of SEQ ID NOS:115, 116, and 117, respectively.

61. The IFNGR2 binding molecule of claim 60, wherein the sdAb has at least 95% identity to a polypeptide sequence of SEQ ID NO:29.

62. The IFNGR2 binding molecule of claim 1, wherein the sdAb comprises the CDR1, the CDR2, and the CDR3 of SEQ ID NOS:118, 119, and 120, respectively.

63. The IFNGR2 binding molecule of claim 62, wherein the sdAb has at least 95% identity to a polypeptide sequence of SEQ ID NO:30.

64. The IFNGR2 binding molecule of claim 1, wherein the sdAb comprises the CDR1, the CDR2, and the CDR3 of SEQ ID NOS:121, 122, and 123, respectively.

65. The IFNGR2 binding molecule of claim 64, wherein the sdAb has at least 95% identity to a polypeptide sequence of SEQ ID NO:31.

66. The IFNGR2 binding molecule of claim 1, wherein the sdAb comprises the CDR1, the CDR2, and the CDR3 of SEQ ID NOS:124, 125, and 126, respectively.

67. The IFNGR2 binding molecule of claim 66, wherein the sdAb has at least 95% identity to a polypeptide sequence of SEQ ID NO:32.

68. The IFNGR2 binding molecule of claim 1, wherein the sdAb comprises the CDR1, the CDR2, and the CDR3 of SEQ ID NOS:127, 128, and 129, respectively.

69. The IFNGR2 binding molecule of claim 68, wherein the sdAb has at least 95% identity to a polypeptide sequence of SEQ ID NO:33.

70. The IL2Rg2 binding molecule of claim 1, wherein the sdAb is linked to a second binding molecule that specifically binds to the extracellular domain of a second cell surface molecule.

71. A pharmaceutically acceptable formulation of an IFNgR2 binding molecule of claim 2.

72. A kit comprising the IFNgR2 binding molecule of claim 1.

73. A nucleic acid encoding the sequence of the IL2Rg2 binding molecule of claim 1.

74. The nucleic acid sequence of claim 73, encoding the sequence of the IL2Rg2 binding molecule comprising the sdAb having the CDR1, the CDR2, and the CDR3 of SEQ ID NOS:34, 35, and 36, respectively.

75. The nucleic acid of claim 73, encoding the sequence of the IL2Rg2 binding molecule comprising the sdAb having the CDR1, the CDR2, and the CDR3 of SEQ ID NOS:37, 38, and 39, respectively.

76. The nucleic acid of claim 73, encoding the sequence of the IL2Rg2 binding molecule comprising the sdAb having the CDR1, the CDR2, and the CDR3 of SEQ ID NOS:40, 41, and 42, respectively.

77. The nucleic acid of claim 73, encoding the sequence of the IL2Rg2 binding molecule comprising the sdAb having the CDR1, the CDR2, and the CDR3 of SEQ ID NOS:43, 44, and 45, respectively.

78. The nucleic acid of claim 73, encoding the sequence of the IL2Rg2 binding molecule comprising the sdAb having the CDR1, the CDR2, and the CDR3 of SEQ ID NOS:46, 47, and 48, respectively.

79. The nucleic acid of claim 73, encoding the sequence of the IL2Rg2 binding molecule comprising the sdAb having the CDR1, the CDR2, and the CDR3 of SEQ ID NOS:49, 50, and 51, respectively.

80. The nucleic acid of claim 73, encoding the sequence of the IL2Rg2 binding molecule comprising the sdAb having the CDR1, the CDR2, and the CDR3 of SEQ ID NOS:52, 53, and 54, respectively.

81. The nucleic acid of claim 73, encoding the sequence of the IL2Rg2 binding molecule comprising the sdAb having the CDR1, the CDR2, and the CDR3 of SEQ ID NOS:55, 56, and 57, respectively.

82. The nucleic acid of claim 73, encoding the sequence of the IL2Rg2 binding molecule comprising the sdAb having the CDR1, the CDR2, and the CDR3 of SEQ ID NOS:58, 59, and 60, respectively.

83. The nucleic acid of claim 73, encoding the sequence of the IL2Rg2 binding molecule comprising the sdAb having the CDR1, the CDR2, and the CDR3 of SEQ ID NOS:61, 62, and 63, respectively.

84. The nucleic acid of claim 73, encoding the sequence of the IL2Rg2 binding molecule comprising the sdAb having the CDR1, the CDR2, and the CDR3 of SEQ ID NOS:64, 65, and 66, respectively.

85. The nucleic acid of claim 73, encoding the sequence of the IL2Rg2 binding molecule comprising the sdAb having the CDR1, the CDR2, and the CDR3 of SEQ ID NOS:67, 68, and 69, respectively.

86. The nucleic acid of claim 73, encoding the sequence of the IL2Rg2 binding molecule comprising the sdAb having the CDR1, the CDR2, and the CDR3 of SEQ ID NOS:70, 71, and 72, respectively.

87. The nucleic acid of claim 73, encoding the sequence of the IL2Rg2 binding molecule comprising the sdAb having the CDR1, the CDR2, and the CDR3 of SEQ ID NOS:73, 74, and 75, respectively.

88. The nucleic acid of claim 73, encoding the sequence of the IL2Rg2 binding molecule comprising the sdAb having the CDR1, the CDR2, and the CDR3 of SEQ ID NOS:76, 77, and 78, respectively.

89. The nucleic acid of claim 73, encoding the sequence of the IL2Rg2 binding molecule comprising the sdAb having the CDR1, the CDR2, and the CDR3 of SEQ ID NOS:79, 80, and 81, respectively.

90. The nucleic acid of claim 73, encoding the sequence of the IL2Rg2 binding molecule comprising the sdAb having the CDR1, the CDR2, and the CDR3 of SEQ ID NOS:82, 83, and 84, respectively.

91. The nucleic acid of claim 73, encoding the sequence of the IL2Rg2 binding molecule comprising the sdAb having the CDR1, the CDR2, and the CDR3 of SEQ ID NOS:85, 86, and 87, respectively.

92. The nucleic acid of claim 73, encoding the sequence of the IL2Rg2 binding molecule comprising the sdAb having the CDR1, the CDR2, and the CDR3 of SEQ ID NOS:88, 89, and 90, respectively.

93. The nucleic acid of claim 73, encoding the sequence of the IL2Rg2 binding molecule comprising the sdAb having the CDR1, the CDR2, and the CDR3 of SEQ ID NOS:91, 92, and 93, respectively.

94. The nucleic acid of claim 73, encoding the sequence of the IL2Rg2 binding molecule comprising the sdAb having the CDR1, the CDR2, and the CDR3 of SEQ ID NOS:94, 95, and 96, respectively.

95. The nucleic acid of claim 73, encoding the sequence of the IL2Rg2 binding molecule comprising the sdAb having the CDR1, the CDR2, and the CDR3 of SEQ ID NOS:97, 98, and 99, respectively.

96. The nucleic acid of claim 73, encoding the sequence of the IL2Rg2 binding molecule comprising the sdAb having the CDR1, the CDR2, and the CDR3 of SEQ ID NOS:100, 101, and 102, respectively.

97. The nucleic acid of claim 73, encoding the sequence of the IL2Rg2 binding molecule comprising the sdAb having the CDR1, the CDR2, and the CDR3 of SEQ ID NOS:103, 104, and 105, respectively.

98. The nucleic acid of claim 73, encoding the sequence of the IL2Rg2 binding molecule comprising the sdAb having the CDR1, the CDR2, and the CDR3 of SEQ ID NOS:106, 107, and 108, respectively.

99. The nucleic acid of claim 73, encoding the sequence of the IL2Rg2 binding molecule comprising the sdAb having the CDR1, the CDR2, and the CDR3 of SEQ ID NOS:109, 110, and 111, respectively.

100. The nucleic acid of claim 73, encoding the sequence of the IL2Rg2 binding molecule comprising the sdAb having the CDR1, the CDR2, and the CDR3 of SEQ ID NOS:112, 113, and 114, respectively.

101. The nucleic acid of claim 73, encoding the sequence of the IL2Rg2 binding molecule comprising the sdAb having the CDR1, the CDR2, and the CDR3 of SEQ ID NOS:115, 116, and 117, respectively.

102. The nucleic acid of claim 73, encoding the sequence of the IL2Rg2 binding molecule comprising the sdAb having the CDR1, the CDR2, and the CDR3 of SEQ ID NOS:118, 119, and 120, respectively.

103. The nucleic acid of claim 73, encoding the sequence of the IL2Rg2 binding molecule comprising the sdAb having the CDR1, the CDR2, and the CDR3 of SEQ ID NOS:121, 122, and 123, respectively.

104. The nucleic acid of claim 73, encoding the sequence of the IL2Rg2 binding molecule comprising the sdAb having the CDR1, the CDR2, and the CDR3 of SEQ ID NOS:124, 125, and 126, respectively.

105. The nucleic acid of claim 73, encoding the sequence of the IL2Rg2 binding molecule comprising the sdAb having the CDR1, the CDR2, and the CDR3 of SEQ ID NOS:127, 128, and 129, respectively.

106. A recombinant viral or non-viral vector comprising the nucleic acid of claim 73.

107. A host cell comprising the nucleic acid of claim 73.

108. A method for treating an autoimmune or inflammatory disease, disorder, or condition in a mammalian subject by administering to said subject a therapeutically effective amount of a IFNgR2 binding molecule of claim 1.

109. A pharmaceutical formulation comprising the viral or non-viral vector of claim 106.

* * * * *

SEQUENCE LISTING

```
<160> NUMBER OF SEQ ID NOS: 170

<210> SEQ ID NO 1
<211> LENGTH: 337
<212> TYPE: PRT
<213> ORGANISM: Homo sapiens
```

<400> SEQUENCE: 1

```
Met Arg Pro Thr Leu Leu Trp Ser Leu Leu Leu Leu Gly Val Phe
1               5                   10                  15
Ala Ala Ala Ala Ala Pro Pro Asp Pro Leu Ser Gln Leu Pro Ala
                20              25                  30
Pro Gln His Pro Lys Ile Arg Leu Tyr Asn Ala Glu Gln Val Leu Ser
        35                  40                  45
Trp Glu Pro Val Ala Leu Ser Asn Ser Thr Arg Pro Val Val Tyr Gln
    50                  55                  60
Val Gln Phe Lys Tyr Thr Asp Ser Lys Trp Phe Thr Ala Asp Ile Met
65                  70                  75                  80
Ser Ile Gly Val Asn Cys Thr Gln Ile Thr Ala Thr Glu Cys Asp Phe
                85                  90                  95
Thr Ala Ala Ser Pro Ser Ala Gly Phe Pro Met Asp Phe Asn Val Thr
                100                 105                 110
Leu Arg Leu Arg Ala Glu Leu Gly Ala Leu His Ser Ala Trp Val Thr
                115                 120                 125
Met Pro Trp Phe Gln His Tyr Arg Asn Val Thr Val Gly Pro Pro Glu
    130                 135                 140
Asn Ile Glu Val Thr Pro Gly Glu Gly Ser Leu Ile Ile Arg Phe Ser
145                 150                 155                 160
Ser Pro Phe Asp Ile Ala Asp Thr Ser Thr Ala Phe Phe Cys Tyr Tyr
                165                 170                 175
Val His Tyr Trp Glu Lys Gly Gly Ile Gln Gln Val Lys Gly Pro Phe
                180                 185                 190
Arg Ser Asn Ser Ile Ser Leu Asp Asn Leu Lys Pro Ser Arg Val Tyr
                195                 200                 205
Cys Leu Gln Val Gln Ala Gln Leu Leu Trp Asn Lys Ser Asn Ile Phe
    210                 215                 220
Arg Val Gly His Leu Ser Asn Ile Ser Cys Tyr Glu Thr Met Ala Asp
225                 230                 235                 240
Ala Ser Thr Glu Leu Gln Gln Val Ile Leu Ile Ser Val Gly Thr Phe
                245                 250                 255
Ser Leu Leu Ser Val Leu Ala Gly Ala Cys Phe Phe Leu Val Leu Lys
                260                 265                 270
Tyr Arg Gly Leu Ile Lys Tyr Trp Phe His Thr Pro Pro Ser Ile Pro
                275                 280                 285
Leu Gln Ile Glu Glu Tyr Leu Lys Asp Pro Thr Gln Pro Ile Leu Glu
    290                 295                 300
Ala Leu Asp Lys Asp Ser Ser Pro Lys Asp Asp Val Trp Asp Ser Val
305                 310                 315                 320
Ser Ile Ile Ser Phe Pro Glu Lys Glu Gln Glu Asp Val Leu Gln Thr
                325                 330                 335
Leu
```

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Gln Val Gln Leu Val Glu Ser Gly Gly Gly Leu Val Gln Ala Gly Gly

```
                1               5                   10                  15
Ser Leu Arg Leu Ser Cys Ala Ala Ser Gly Arg Thr Phe Thr Ser Tyr
            20                  25                  30

Ala Met Asn Trp Phe Arg Gln Ala Pro Gly Lys Glu Arg Glu Phe Val
            35                  40                  45

Ala Ala Ile Ser Trp Ser Ser Gly Asn Thr Tyr Val Ala Asp Ser Val
            50                  55                  60

Lys Gly Arg Phe Ala Ile Ser Arg Asp Lys Ala Lys Asn Thr Met Tyr
 65                     70                  75                  80

Leu Gln Met Asn Ser Leu Ala Pro Glu Asp Thr Ala Val Tyr Tyr Cys
                    85                  90                  95

Ala Ala Thr Thr Ile Ala Thr Met Ser Asp Glu Tyr Thr Tyr Trp Gly
                    100                 105                 110

Gln Gly Thr Gln Val Thr Val Ser Ser
            115                 120
```

<210> SEQ ID NO 3
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Gln Val Gln Leu Val Glu Ser Gly Gly Gly Leu Val Gln Ala Gly Gly
 1               5                   10                  15

Ser Leu Arg Leu Ser Cys Ala Ala Ser Gly Arg Thr Phe Ser Asn Tyr
            20                  25                  30

Arg Met Gly Trp Phe Arg Gln Ala Pro Gly Lys Glu Arg Glu Phe Val
            35                  40                  45

Ala Ala Ile Ser Arg Gly Gly Gly Thr Thr Leu Tyr Ala Asp Ser Val
            50                  55                  60

Lys Gly Arg Phe Thr Ile Ser Arg Asp Asn Ala Lys Asn Thr Val Asp
 65                     70                  75                  80

Leu Gln Met Asn Arg Leu Lys Pro Glu Asp Thr Ala Val Tyr Phe Cys
                    85                  90                  95

Ala Ala Gly Asp Phe Ser Thr Thr Trp Asp Glu Tyr Asn Tyr Trp Gly
                    100                 105                 110

Gln Gly Thr Gln Val Thr Val Ser Ser
            115                 120
```

<210> SEQ ID NO 4
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Gln Val Gln Leu Val Glu Ser Gly Gly Gly Leu Val Gln Ala Gly Gly
 1               5                   10                  15

Ser Leu Arg Leu Ser Cys Val Ala Ser Gly Arg Thr Phe Ser Ser Tyr
            20                  25                  30

Ala Met Gly Trp Phe Arg Gln Thr Pro Gly Lys Glu Arg Glu Phe Val
            35                  40                  45

Ser Ala Ile Ser Arg Gly Gly Gly Ser Thr Asp Tyr Ala Asp Ser Val
```

```
            50                  55                  60
Lys Gly Arg Phe Thr Ile Ser Arg Asp Asn Ala Lys Asn Thr Val Tyr
 65                  70                  75                  80

Leu Gln Met Asn Asn Leu Lys Ser Glu Asp Thr Ala Val Tyr Tyr Cys
                 85                  90                  95

Ala Leu Arg Ala Tyr Ser Gly Arg Tyr Tyr Gln Phe Leu Glu Tyr Asp
            100                 105                 110

Tyr Trp Gly Gln Gly Thr Gln Val Thr Val Ser Ser
            115                 120

<210> SEQ ID NO 5
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Ala Gly Gly
 1               5                  10                  15

Ser Leu Arg Leu Ser Cys Thr Val Ser Gly Arg Thr Phe Ser Ser Tyr
                 20                  25                  30

Ala Val Ala Trp Phe Arg Gln Ala Pro Gly Asn Val Arg Glu Leu Ala
             35                  40                  45

Ala Ala Leu Ser Arg Gly Gly Gly Ser Ala Tyr Tyr Thr Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Arg Asn Tyr Asp Gly Thr Tyr Tyr Gln Glu Asn Gln Tyr Asn
            100                 105                 110

Tyr Trp Gly Gln Gly Thr Gln Val Thr Val Ser Ser
            115                 120

<210> SEQ ID NO 6
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Val Glu Ser Gly Gly Gly Leu Val Gln Ala Gly Gly
 1               5                  10                  15

Ser Leu Leu Leu Ser Cys Ala Ala Ser Gly Arg Thr Phe Ser Thr Tyr
                 20                  25                  30

Ala Met Gly Trp Phe Arg Gln Ala Pro Gly Lys Glu Arg Met Phe Val
             35                  40                  45

Ala Ala Ile Ser Val Asn Gly Gly Ser Thr Tyr Tyr Ala Asp Ser Val
         50                  55                  60

Thr Gly Arg Phe Thr Ile Ser Arg Asp Asn Ala Lys Asn Thr Met Tyr
 65                  70                  75                  80

Leu Gln Met Asn Asn Leu Lys Pro Gly Asp Thr Ala Val Tyr Tyr Cys
                 85                  90                  95

Ala Ala Arg Arg Pro Tyr Pro Gly Ser Asp Phe Leu Thr Trp Ala Ser
```

```
                100                 105                 110
Tyr Asp Tyr Arg Gly Gln Gly Thr Leu Val Thr Val Ser Ser
        115                 120                 125

<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Glu Ser Gly Gly Gly Leu Val Gln Ala Gly Gly
1               5                   10                  15

Phe Leu Arg Leu Ser Cys Ala Ala Ser Gly Arg Thr Phe Ser Tyr Thr
            20                  25                  30

Thr Ile Gly Trp Phe Arg Gln Ala Pro Gly Lys Glu Arg Glu Phe Val
        35                  40                  45

Ala Val Ile Ser Ala Gly Gly Ser Arg Asp Tyr Ala Asp Ala Leu
    50                  55                  60

Lys Gly Arg Phe Thr Ile Ser Arg Asp Asn Ala Lys Lys Met Val Tyr
65                  70                  75                  80

Leu Gln Met Asn Asn Leu Lys Pro Glu Asp Thr Ala Val Tyr Tyr Cys
                85                  90                  95

Ala Val Arg Arg Asn Thr Asp Thr Tyr Thr Thr Thr Gly Asp Tyr Asp
            100                 105                 110

Tyr Trp Gly Gln Gly Thr Gln Val Thr Val Ser Ser
        115                 120

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Glu Ser Gly Gly Gly Leu Val Gln Pro Gly Asp
1               5                   10                  15

Ser Leu Arg Leu Ser Cys Val Ala Ser Gly Gly Thr Ile Ser Ser Leu
            20                  25                  30

Ala Met Gly Trp Phe Arg Gln Ala Pro Gly Lys Glu Arg Glu Phe Val
        35                  40                  45

Ala Ala Ile Ser Trp Ser Gly Arg Ser Thr Tyr Tyr Val Asp Ser Val
    50                  55                  60

Lys Gly Arg Phe Thr Ile Ser Thr Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Val Ala Gly Glu Asp Gly His Ser Glu Tyr Asp Tyr Trp Gly Gln Gly
            100                 105                 110

Thr Gln Val Thr Val Ser Ser
        115

<210> SEQ ID NO 9
<211> LENGTH: 125
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ala Asn Tyr
            20                  25                  30

Ala Met Gly Trp Phe Arg Gln Ala Pro Gly Lys Glu Arg Glu Thr Val
        35                  40                  45

Ala Ala Ile Ser Arg Gly Gly Ser Thr Trp Tyr Ala Asp Ser Val
    50                  55                  60

Lys Gly Arg Phe Thr Ile Ser Lys Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Arg Ser Tyr Ser Gly Ser Tyr Thr Tyr Ser Phe Gly Glu Tyr
            100                 105                 110

Asp Tyr Trp Gly Gln Gly Thr Gln Val Thr Val Ser Ser
        115                 120                 125

<210> SEQ ID NO 10
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Ser Thr Tyr
            20                  25                  30

Ala Leu Gly Trp Phe Arg Gln Ala Pro Gly Lys Glu Arg Glu Phe Ile
        35                  40                  45

Ala Ala Ile Ser Arg Gly Gly Ser Thr Asp Tyr Ala Asp Ser Val
    50                  55                  60

Lys Gly Arg Phe Thr Ile Ser Arg Asp Asn Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ser Tyr Ser Ser Ser Tyr Tyr Tyr Ser Gln Tyr Glu Tyr
            100                 105                 110

Asp Tyr Trp Gly Gln Gly Thr Gln Val Thr Val Ser Ser
        115                 120                 125

<210> SEQ ID NO 11
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Ala Gly Gly
1               5                   10                  15

```
Ser Leu Arg Leu Ser Cys Ala Ala Ser Gly Arg Thr Phe Ser Ser Val
            20                  25                  30

Ala Met Ala Trp Phe Arg Gln Ala Pro Gly Lys Glu Arg Glu Phe Val
        35                  40                  45

Ser Ala Ile Ser Ser Gly Gly Gly Ser Thr Asp Tyr Ala Asp Ser Val
 50                  55                  60

Lys Gly Arg Phe Thr Ile Ser Lys Asp Asn Ala Lys Asn Thr Met Tyr
 65                  70                  75                  80

Leu Gln Met Asp Ser Leu Lys Pro Glu Asp Thr Ala Val Tyr Tyr Cys
                85                  90                  95

Ala Ala Arg Asp Tyr Ser Ser Arg Arg Tyr Tyr Gln Ser Arg Tyr Glu
            100                 105                 110

Tyr Asp Leu Trp Gly Leu Gly Thr Gln Val Thr Val Ser Ser
        115                 120                 125

<210> SEQ ID NO 12
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Arg Ser Tyr
            20                  25                  30

Ser Met Gly Trp Phe Arg Gln Ala Pro Gly Lys Glu Arg Glu Phe Val
        35                  40                  45

Ala Ala Ile Ser Trp Tyr Ser Gly Thr Thr Tyr Tyr Ala Asp Pro Val
 50                  55                  60

Lys Gly Arg Phe Thr Ile Ser Arg Asp Asp Ala Lys Asn Thr Leu Tyr
 65                  70                  75                  80

Leu Gln Met Asn Ser Leu Lys Pro Glu Asp Thr Ala Val Tyr Tyr Cys
                85                  90                  95

Ala Ala Asn Glu Ile Ala Thr Met Glu Ser Ser Asn Asp Tyr Trp Gly
            100                 105                 110

Gln Gly Thr Gln Val Thr Val Ser Ser
        115                 120

<210> SEQ ID NO 13
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Gly Gly Gly Leu Val Gln Pro Gly Gly
 1               5                  10                  15

Ser Leu Arg Leu Ser Cys Thr Ala Ser Gly Arg Pro Arg Thr Thr Tyr
            20                  25                  30

Ala Met Gly Trp Phe Arg Gln Ala Pro Gly Lys Glu Arg Glu Ile Val
        35                  40                  45

Ala Ala Ile Ser Lys Ala Gly Gly Ser Thr Tyr Val Ala Asp Ser Ala
 50                  55                  60
```

Lys Gly Arg Phe Ala Ile Ser Lys Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ala Gly Phe Ala Ala Gln Ile Phe Glu Tyr Asp Tyr Trp
            100                 105                 110

Gly Gln Gly Thr Leu Val Thr Val Ser Ser
            115                 120

<210> SEQ ID NO 14
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Ala Gly Gly
1               5                   10                  15

Ser Met Arg Leu Ser Cys Ala Asn Ser Gly Arg Thr Phe Gly Thr Tyr
            20                  25                  30

Ala Met Gly Trp Phe Arg Gln Ser Pro Gly Lys Glu Arg Glu Arg Val
            35                  40                  45

Ala Ser Ile Asp Arg Asp Gly Ser Met Ser Tyr Tyr Ala Asp Ser Val
        50                  55                  60

Lys Gly Arg Phe Thr Ile Ser Gly Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Arg Arg Ala Val Ile Ser Leu Gln Thr Val Asp Tyr Trp
            100                 105                 110

Gly Gln Gly Thr Gln Val Thr Val Ser Ser
            115                 120

<210> SEQ ID NO 15
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Arg Leu Val Gln Thr Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
            35                  40                  45

Ala Ala Ile Ser Trp Tyr Ser Gly Asn Thr Tyr Tyr Ala Asp Ser Val
        50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asn Gln Ile Ala Thr Met Ile Ser Val Gly Asp Tyr Trp Gly
            100                 105                 110

Gln Gly Thr Leu Val Thr Val Ser Ser
        115                 120

<210> SEQ ID NO 16
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Leu Val Glu Ala Gly Gly
1               5                   10                  15

Ser Leu Arg Leu Ala Cys Ala Ala Ser Gly Ser Ile Phe Arg Leu Asn
            20                  25                  30

Leu Met Gly Trp Tyr Arg Gln Ala Pro Gly Lys Gln Arg Glu Leu Val
        35                  40                  45

Ala His Val Gly Thr Thr Gly Asn Thr Ala Tyr Ala Asp Ser Val Lys
    50                  55                  60

Gly Arg Phe Thr Ile Ser Lys Asp Asp Ala Lys Asn Met Val Phe Leu
65                  70                  75                  80

Gln Met Asn Ser Leu Lys Pro Glu Asp Thr Ala Val Tyr Tyr Cys Tyr
                85                  90                  95

Ala Asp Arg Trp Gly Gln Phe Ser Trp Gly Gln Gly Thr Gln Val Thr
            100                 105                 110

Val Ser Ser
        115

<210> SEQ ID NO 17
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Thr Gly Tyr
            20                  25                  30

Ala Met Gly Trp Phe Arg Gln Ala Pro Gly Lys Glu Arg Glu Phe Val
        35                  40                  45

Ala Val Ile Thr Trp Ser Gly Ala Thr Thr Tyr Tyr Ser Ala Ser Val
    50                  55                  60

Lys Gly Arg Phe Thr Leu Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ile Arg Ile Arg Asp Gly Val Ser Pro Glu Asn Pro Asn Glu Tyr
            100                 105                 110

Gly Tyr Trp Gly Gln Gly Thr Gln Val Thr Val Ser Ser
        115                 120                 125

<210> SEQ ID NO 18
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Glu Ser Gly Gly Gly Leu Val Gln Ala Gly Gly
1               5                   10                  15

Ser Leu Arg Leu Ser Cys Val Ala Ser Gly Arg Thr Val Gly Tyr Gly
            20                  25                  30

Met Ala Trp Phe Arg Gln Ala Pro Gly Lys Gln Arg Asp Val Val Ala
        35                  40                  45

Ala Ile Thr Trp Ser Gly Thr Ser Thr Tyr Tyr Pro Asp Ser Val Lys
    50                  55                  60

Gly Arg Phe Thr Ile Ser Arg Asp Asn Ala Lys Asn Thr Met Tyr Leu
65                  70                  75                  80

Gln Met Ser Ser Leu Lys Pro Glu Asp Thr Ala Val Tyr Tyr Cys Ala
                85                  90                  95

Ala Gly Ser Arg Arg Arg Val Gly Val Asp Val Gly Tyr Gly Tyr Asp Tyr
            100                 105                 110

Trp Gly Gln Gly Thr Gln Val Thr Val Ser Ser
        115                 120

<210> SEQ ID NO 19
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Thr Phe Ser
            20                  25                  30

Thr His Asn Met Gly Trp Phe Arg Gln Ala Pro Gly Lys Glu Arg Glu
        35                  40                  45

Phe Val Gly Gly Ile Met Trp Thr Ser Arg Ala Ser Tyr Ala Asp Ser
    50                  55                  60

Val Lys Gly Arg Phe Thr Val Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Ala Trp Tyr Gly Asn Ser Gly Ala Ser Tyr Asp Tyr Trp
            100                 105                 110

Gly Gln Gly Thr Gln Val Thr Val Ser Ser
        115                 120

<210> SEQ ID NO 20
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Leu Val Gln Leu Val Gln
1               5                   10                  15

```
Ala Gly Gly Ser Leu Arg Leu Ser Cys Ala Ala Ser Gly Arg Thr Phe
            20                  25                  30

Ser Gly Tyr Asn Met Gly Trp Phe Arg Gln Ala Pro Gly Lys Glu Arg
            35                  40                  45

Glu Phe Val Ala Ala Ile Ala Trp Ala Gly Ser Arg Thr Tyr Tyr Thr
 50                  55                  60

Asp Ser Val Lys Gly Arg Phe Thr Ile Ser Arg Asp Asn Ala Lys Asn
 65                  70                  75                  80

Thr Met Tyr Leu Gln Met Asn Thr Leu Arg Pro Glu Asp Thr Ala Val
            85                  90                  95

Tyr Tyr Cys Ala Ala His Asp Glu Thr Tyr Tyr Arg Leu Asp Arg Val
            100                 105                 110

Asp Leu Tyr Thr His Trp Gly Gln Gly Thr Gln Val Thr Val Ser Ser
            115                 120                 125

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Leu Val Gln Pro Gly Glu
 1               5                   10                  15

Ser Leu Arg Leu Ser Cys Ala Ala Ser Gly Pro Phe Thr Arg Tyr Ala
            20                  25                  30

Met Gly Trp Phe Arg Gln Ala Pro Gly Lys Glu Arg Glu Phe Val Ala
            35                  40                  45

Ala Ile Ser Trp Ser Ser Gly Asn Thr Tyr Tyr Val Asp Ser Val Lys
 50                  55                  60

Gly Arg Phe Thr Ile Ser Arg Asp Asn Ala Lys Asn Thr Met Tyr Leu
 65                  70                  75                  80

Gln Met Asn Ser Leu Lys Pro Glu Asp Thr Ala Val Tyr Tyr Cys Ala
            85                  90                  95

Ala Asn Glu Val Ala Thr Met Ser Gly Pro Asp Asp Tyr Trp Gly Gln
            100                 105                 110

Gly Thr Gln Val Thr Val Ser Ser
            115                 120

<210> SEQ ID NO 22
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Glu Ser Gly Gly Gly Leu Val Gln Ala Gly Gly
 1               5                   10                  15

Ser Leu Arg Leu Ser Cys Ala Ala Ser Gly Gly Ser Phe Gly Arg Tyr
            20                  25                  30

Thr Met Gly Trp Tyr Arg Gln Ala Pro Gly Lys Glu Arg Glu Phe Val
            35                  40                  45

Ala Val Ile Ser Trp Ser Gly Thr Asn Thr Tyr Tyr Ala Asp Ser Val
 50                  55                  60
```

```
Lys Gly Arg Phe Thr Ile Ser Arg Asp Asn Ala Lys Asn Thr Met Tyr
 65                  70                  75                  80

Leu Gln Met Asn Asp Leu Lys Pro Glu Asp Thr Ala Val Tyr Tyr Cys
                 85                  90                  95

Ala Ala Arg Glu Thr Tyr Tyr Ser His Trp Asp Glu Arg Met Glu Tyr
            100                 105                 110

Asp Tyr Trp Gly Gln Gly Thr Gln Val Thr Val Ser Ser
        115                 120                 125

<210> SEQ ID NO 23
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Glu Ser Gly Gly Gly Leu Val Gln Ala Gly Asp
1               5                   10                  15

Ser Leu Arg Leu Ser Cys Val Ala Ser Gly Ser Ile Asp Ser Ser Tyr
            20                  25                  30

Tyr Val Ser Trp Phe Arg Gln Ala Pro Gly Lys Glu Arg Asp Leu Val
        35                  40                  45

Ala Ala Ile Asn Trp Gly Asp Ser Arg Thr Ala Tyr Ala Asp Ser Val
    50                  55                  60

Lys Gly Arg Phe Thr Ile Ser Arg Asp Asn Ala Lys Asn Thr Val Tyr
 65                  70                  75                  80

Leu Gln Met His Ser Leu Arg Pro Asn Asp Thr Ala Val Tyr Tyr Cys
                 85                  90                  95

Ala Ser Arg Ile Gly Leu Gly Gly Pro Val Val Ala Ala Pro Thr Arg
            100                 105                 110

Tyr Pro Tyr Trp Gly Gln Gly Thr Leu Val Thr Val Ser Ser
        115                 120                 125

<210> SEQ ID NO 24
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Glu Ser Gly Gly Gly Leu Val Gln Ala Gly Gly
1               5                   10                  15

Ser Leu Arg Leu Ser Cys Ala Ala Ser Glu Ser Ile Leu Arg Phe Asn
            20                  25                  30

Val Met Ser Trp Leu Arg Gln Ala Pro Gly Lys Gln Arg Glu Leu Val
        35                  40                  45

Ala Val Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Asp Glu Ser Gly Gln Tyr Tyr Trp Gly Gln Gly Thr Gln Val Thr
            100                 105                 110
```

Val Ser Ser
        115

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Thr Ser Ser Ala
            20                  25                  30

Ala Leu Ala Trp Phe Arg Gln Ala Pro Gly Lys Glu Arg Glu Leu Asp
        35                  40                  45

Pro Thr Ile Thr Ser Gly Gly Ser Thr Tyr Tyr Ala Asp Ser Val
    50                  55                  60

Lys Gly Arg Phe Thr Ile Ser Lys Asp Asn Ala Lys Asn Thr Leu Tyr
65                  70                  75                  80

Leu Gln Met Ser Ser Leu Lys Pro Glu Asp Thr Ala Val Tyr Tyr Cys
                85                  90                  95

Ala Ala Arg Phe Tyr Ser Thr Thr Tyr Tyr Arg Glu His Glu Tyr
            100                 105                 110

Ser Asp Trp Gly Gln Gly Thr Gln Val Thr Val Ser Ser
        115                 120                 125

<210> SEQ ID NO 26
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Thr Ser
            20                  25                  30

Phe Gly Ser Leu Ser Met Gly Trp Phe Arg Gln Ala Pro Gly Lys Glu
        35                  40                  45

Arg Glu Phe Val Ala Ala Ile Ser Arg Asn Ile Gly Arg Thr Tyr Tyr
    50                  55                  60

Ala Asp Ser Val Lys Asp Arg Phe Thr Ile Ser Arg Asp Asn Ala Lys
65                  70                  75                  80

Asn Thr Ala Ser Leu Gln Met Asn Ser Leu Glu Pro Glu Asp Thr Ala
                85                  90                  95

Val Tyr Asn Cys Ala Ala Thr Asn Ser Tyr Asp Asp Leu Arg Arg Ser
            100                 105                 110

Tyr Ala Tyr Asp Tyr Trp Gly Gln Gly Thr Gln Val Thr Val Ser Ser
        115                 120                 125

<210> SEQ ID NO 27
<211> LENGTH: 125
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 27

Gln Val Gln Leu Val Glu Ser Gly Gly Gly Leu Val Gln Ala Gly Gly
1               5                   10                  15

Phe Leu Arg Leu Ser Cys Ala Ala Ser Gly Arg Thr Phe Ser Ser Leu
            20                  25                  30

Ala Met Ala Trp Phe Arg Gln Ala Pro Gly Lys Glu Arg Glu Phe Val
        35                  40                  45

Ala Ala Ile Ser Arg Ser Gly Gly Ser Thr Asp Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Ser Ser Leu Lys Pro Glu Asp Thr Ala Val Tyr Tyr Cys
                85                  90                  95

Ala Ala Arg Asp Tyr Ser Thr Leu Gln Tyr Tyr Asn Glu Tyr Glu Tyr
            100                 105                 110

Ser Asp Trp Gly Gln Gly Thr Leu Val Thr Val Ser Ser
            115                 120                 125

<210> SEQ ID NO 28
<211> LENGTH: 125
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 28

Gln Val Gln Leu Val Glu Ser Gly Gly Gly Leu Val Gln Ala Gly Asp
1               5                   10                  15

Ser Leu Arg Leu Ser Cys Ala Ala Ser Gly Pro Thr Phe Ser Thr Tyr
            20                  25                  30

Ala Met Ala Trp Phe Arg Gln Ala Pro Gly Lys Glu Arg Glu Phe Val
        35                  40                  45

Ala Ala Ile Thr Gln Ser Gly Arg Thr Thr Tyr Tyr Glu Asp Ser Val
    50                  55                  60

Lys Gly Arg Phe Thr Ile Ser Lys Asp Asn Ala Lys Asn Thr Leu Tyr
65                  70                  75                  80

Leu Gln Met Asn Ser Leu Gln Pro Glu Asp Thr Ala Val Tyr Tyr Cys
                85                  90                  95

Ala Ala Arg Asp Leu Trp Ser Asp Ser Pro Asp Asp Trp Arg Ile Tyr
            100                 105                 110

Ser Phe Trp Gly Gln Gly Thr Gln Val Thr Val Ser Ser
            115                 120                 125

<210> SEQ ID NO 29
<211> LENGTH: 128
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 29

Gln Val Gln Leu Val Glu Ser Gly Gly Gly Leu Val Gln Ala Gly Gly
1               5                   10                  15

Ser Leu Arg Leu Ser Cys Ala Ala Ala Arg Arg Thr Leu His Asn Phe

-continued

```
                    20                  25                  30

Ala Met Ala Trp Phe Arg Gln Ala Pro Gly Lys Glu Arg Glu Phe Val
                35                  40                  45

Ala Ala Ile Ser Lys Gly Gly Ser Ala Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asn Asp Leu Ala Ser Tyr Ser Asp Ser Ser Tyr Thr Ser Thr
            100                 105                 110

Ser Arg Tyr Asp Tyr Trp Gly Gln Gly Thr Gln Val Thr Val Ser Ser
            115                 120                 125
```

<210> SEQ ID NO 30
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Gln Val Gln Leu Val Glu Ser Gly Gly Gly Leu Val Gln Thr Gly Gly
1               5                   10                  15

Ser Leu Arg Leu Ser Cys Ala Ala Ser Gly Arg Thr Phe Ser Ser Tyr
                20                  25                  30

Ala Met Ala Trp Phe Arg Gln Ala Pro Gly Lys Glu Arg Glu Phe Val
                35                  40                  45

Ala Ala Ile Ser Ile Leu Gly Gly Ser Ala Asp Tyr Glu Asp Ser Val
            50                  55                  60

Gln Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Arg Arg Pro Ala Pro Ser Asp Ser Tyr Trp Ser Ser Thr Ser
            100                 105                 110

Tyr Ala Tyr Trp Gly Gln Gly Thr Leu Val Thr Val Ser Ser
            115                 120                 125
```

<210> SEQ ID NO 31
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Leu
                20                  25                  30

Ala Met Ala Trp Phe Arg Gln Ala Pro Gly Lys Glu Arg Glu Phe Val
                35                  40                  45

Ala Ala Thr Thr Ile Leu Gly Gly Ser Ala Asp Tyr Gly Asp Pro Val
            50                  55                  60

Lys Gly Arg Phe Thr Ile Ser Arg Asp Asn Ala Lys Asn Thr Val Tyr
```

```
                65                  70                  75                  80
Leu Gln Met Asn Ser Leu Lys Pro Glu Asp Thr Ala Val Tyr Tyr Cys
                    85                  90                  95

Thr Gly Arg Arg Pro Ala Pro Ser Asp Asn Tyr Trp Ser Pro Ala Ser
            100                 105                 110

Tyr Ala Tyr Trp Gly Gln Gly Thr Gln Val Thr Val Ser Ser
        115                 120                 125

<210> SEQ ID NO 32
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Glu Ser Gly Gly Gly Leu Val Gln Ala Gly Gly
1               5                   10                  15

Ser Leu Arg Leu Ser Cys Ala Pro Ser Gly Arg Thr Phe Ser Ser Tyr
            20                  25                  30

Ala Met Ala Trp Phe Arg Gln Pro Pro Gly Lys Glu Arg Glu Phe Val
        35                  40                  45

Ala Ala Ile Thr Val Ser Gly Ala Ser Thr Tyr Tyr Ala Asp Ser Val
    50                  55                  60

Lys Gly Arg Phe Thr Ile Ser Arg Asp Asn Ala Lys Asn Ser Met Tyr
65                  70                  75                  80

Leu Gln Met Asn Ser Leu Lys Pro Glu Asp Thr Ala Val Tyr Tyr Cys
                    85                  90                  95

Ala Ala Gly Gly Pro Gly Thr Ile Phe Pro Asp Tyr Asp Tyr Trp Gly
            100                 105                 110

Gln Gly Thr Gln Val Thr Val Ser Ser
        115                 120

<210> SEQ ID NO 33
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Glu Ser Gly Gly Gly Leu Val Gln Ala Gly Asp
1               5                   10                  15

Ser Leu Thr Leu Ser Cys Thr Ala Ser Gly Arg Thr Phe Ser Gly Tyr
            20                  25                  30

Asn Met Gly Trp Phe Arg Gln Ala Pro Gly Lys Glu Arg Asp Phe Val
        35                  40                  45

Ala Ala Ile Asn Trp Ile Gly Gly Ala Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                    85                  90                  95

His Arg Tyr Ser Glu Lys Phe Tyr Ser Gly Lys Asp Tyr Tyr Thr Arg
            100                 105                 110

Asp Tyr Asp Tyr Trp Gly Gln Gly Thr Gln Val Thr Val Ser Ser
```

-continued

```
<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Thr Phe Thr Ser Tyr Ala Met Asn
1               5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ile Ser Trp Ser Ser Gly Asn Thr Tyr Val Ala Asp Ser Val Lys
1               5                   10                  15

Gly

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Thr Ile Ala Thr Met Ser Asp Glu Tyr Thr Tyr
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Thr Phe Ser Asn Tyr Arg Met Gly
1               5

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ile Ser Arg Gly Gly Gly Thr Thr Leu Tyr Ala Asp Ser Val Lys
1               5                   10                  15

Gly

<210> SEQ ID NO 39
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Asp Phe Ser Thr Thr Trp Asp Glu Tyr Asn Tyr
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Thr Phe Ser Ser Tyr Ala Met Gly
1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Ile Ser Arg Gly Gly Gly Ser Thr Asp Tyr Ala Asp Ser Val Lys
1               5                   10                  15

Gly

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ala Tyr Ser Gly Arg Tyr Tyr Gln Phe Leu Glu Tyr Asp Tyr
1               5                   10                  15

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Thr Phe Ser Ser Tyr Ala Val Ala
1               5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

```
Ala Leu Ser Arg Gly Gly Gly Ser Ala Tyr Tyr Thr Asp Ser Val Lys
1               5                   10                  15
Gly

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Asn Tyr Asp Gly Thr Tyr Tyr Gln Glu Asn Gln Tyr Asn Tyr
1               5                   10                  15

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Thr Phe Ser Thr Tyr Ala Met Gly
1               5

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Ile Ser Val Asn Gly Gly Ser Thr Tyr Tyr Ala Asp Ser Val Thr
1               5                   10                  15
Gly

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Arg Pro Tyr Pro Gly Ser Asp Phe Leu Thr Trp Ala Ser Tyr Asp
1               5                   10                  15
Tyr

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Thr Phe Ser Tyr Thr Thr Ile Gly
1               5
```

```
<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Ile Ser Ala Gly Gly Gly Ser Arg Asp Tyr Ala Asp Ala Leu Lys
1               5                   10                  15

Gly

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Arg Asn Thr Asp Thr Tyr Thr Thr Thr Gly Asp Tyr Asp Tyr
1               5                   10                  15

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Thr Ile Ser Ser Leu Ala Met Gly
1               5

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ile Ser Trp Ser Gly Arg Ser Thr Tyr Tyr Val Asp Ser Val Lys
1               5                   10                  15

Gly

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Glu Asp Gly His Ser Glu Tyr Asp Tyr
1               5                   10

<210> SEQ ID NO 55
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 55

Arg Ser Phe Ala Asn Tyr Ala Met Gly
1               5

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Ile Ser Arg Gly Gly Gly Ser Thr Trp Tyr Ala Asp Ser Val Lys
1               5                   10                  15

Gly

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Tyr Ser Gly Ser Tyr Thr Tyr Ser Phe Gly Glu Tyr Asp Tyr
1               5                   10                  15

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ala Phe Ser Thr Tyr Ala Leu Gly
1               5

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Ile Ser Arg Gly Gly Gly Ser Thr Asp Tyr Ala Asp Ser Val Lys
1               5                   10                  15

Gly

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 60

Arg Ser Tyr Ser Ser Tyr Tyr Ser Gln Tyr Glu Tyr Asp Tyr
1               5                   10                  15

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Thr Phe Ser Ser Val Ala Met Ala
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Ile Ser Ser Gly Gly Gly Ser Thr Asp Tyr Ala Asp Ser Val Lys
1               5                   10                  15

Gly

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Asp Tyr Ser Ser Arg Arg Tyr Tyr Gln Ser Arg Tyr Glu Tyr Asp
1               5                   10                  15

Leu

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Thr Phe Arg Ser Tyr Ser Met Gly
1               5

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ile Ser Trp Tyr Ser Gly Thr Thr Tyr Tyr Ala Asp Pro Val Lys
1               5                   10                  15
```

Gly

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asn Glu Ile Ala Thr Met Glu Ser Ser Asn Asp Tyr
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Pro Arg Thr Thr Tyr Ala Met Gly
1               5

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Ile Ser Lys Ala Gly Gly Ser Thr Tyr Val Ala Asp Ser Ala Lys
1               5                   10                  15

Gly

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ala Gly Phe Ala Ala Gln Ile Phe Glu Tyr Asp Tyr
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Thr Phe Gly Thr Tyr Ala Met Gly
1               5

<210> SEQ ID NO 71
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 71

Ser Ile Asp Arg Asp Gly Ser Met Ser Tyr Tyr Ala Asp Ser Val Lys
1               5                   10                  15

Gly

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Arg Arg Ala Val Ile Ser Leu Gln Thr Val Asp Tyr
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Thr Phe Ser Asn Tyr Ala Met Gly
1               5

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Ile Ser Trp Tyr Ser Gly Asn Thr Tyr Tyr Ala Asp Ser Val Lys
1               5                   10                  15

Gly

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asn Gln Ile Ala Thr Met Ile Ser Val Gly Asp Tyr
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76
```

```
Ser Ile Phe Arg Leu Asn Leu Met Gly
1               5
```

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
His Val Gly Thr Thr Gly Asn Thr Ala Tyr Ala Asp Ser Val Lys Gly
1               5                   10                  15
```

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Asp Arg Trp Gly Gln Phe Ser
1               5
```

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Arg Thr Phe Thr Gly Tyr Ala Met Gly
1               5
```

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Val Ile Thr Trp Ser Gly Ala Thr Thr Tyr Tyr Ser Ala Ser Val Lys
1               5                   10                  15

Gly
```

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Arg Ile Arg Asp Gly Val Ser Pro Glu Asn Pro Asn Glu Tyr Gly Tyr
1               5                   10                  15
```

<210> SEQ ID NO 82
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Thr Val Gly Tyr Gly Met Ala
1               5

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ile Thr Trp Ser Gly Thr Ser Thr Tyr Tyr Pro Asp Ser Val Lys
1               5                   10                  15
Gly

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ser Arg Arg Val Gly Val Asp Val Gly Gly Tyr Asp Tyr
1               5                   10                  15

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Thr Phe Thr Phe Ser Thr His Asn Met Gly
1               5                   10

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Ile Met Trp Thr Ser Arg Ala Ser Tyr Ala Asp Ser Val Lys Gly
1               5                   10                  15

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87
```

```
Ala Trp Tyr Gly Asn Ser Gly Ala Ser Tyr Asp Tyr
1               5                   10
```

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Arg Thr Phe Ser Gly Tyr Asn Met Gly
1               5
```

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Ala Ile Ala Trp Ala Gly Ser Arg Thr Tyr Tyr Thr Asp Ser Val Lys
1               5                   10                  15
Gly
```

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
His Asp Glu Thr Tyr Tyr Arg Leu Asp Arg Val Asp Leu Tyr Thr His
1               5                   10                  15
```

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Pro Phe Thr Arg Tyr Ala Met Gly
1               5
```

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Ala Ile Ser Trp Ser Ser Gly Asn Thr Tyr Tyr Val Asp Ser Val Lys
1               5                   10                  15
Gly
```

```
<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asn Glu Val Ala Thr Met Ser Gly Pro Asp Asp Tyr
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ser Phe Gly Arg Tyr Thr Met Gly
1               5

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Ile Ser Trp Ser Gly Thr Asn Thr Tyr Tyr Ala Asp Ser Val Lys
1               5                   10                  15

Gly

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Glu Thr Tyr Tyr Ser His Trp Asp Glu Arg Met Glu Tyr Asp Tyr
1               5                   10                  15

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Ile Asp Ser Ser Tyr Tyr Val Ser
1               5

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 98

Ala Ile Asn Trp Gly Asp Ser Arg Thr Ala Tyr Ala Asp Ser Val Lys
1               5                   10                  15

Gly

<210> SEQ ID NO 99
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ile Gly Leu Gly Gly Pro Val Val Ala Ala Pro Thr Arg Tyr Pro
1               5                   10                  15

Tyr

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Ile Leu Arg Phe Asn Val Met Ser
1               5

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Val Ile Thr Ser Gly Gly Ser Thr Asn Tyr Ala Asp Ser Val Lys Gly
1               5                   10                  15

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asp Glu Ser Gly Gln Tyr Tyr
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Thr Thr Ser Ser Ala Ala Leu Ala
1               5

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Ile Thr Ser Gly Gly Gly Ser Thr Tyr Tyr Ala Asp Ser Val Lys
1               5                   10                  15
Gly

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Phe Tyr Ser Thr Thr Tyr Tyr Tyr Arg Glu His Glu Tyr Ser Asp
1               5                   10                  15

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Thr Phe Gly Thr Ser Phe Gly Ser Leu Ser Met Gly
1               5                   10

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Ile Ser Arg Asn Ile Gly Arg Thr Tyr Tyr Ala Asp Ser Val Lys
1               5                   10                  15
Asp

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Thr Asn Ser Tyr Asp Asp Leu Arg Arg Ser Tyr Ala Tyr Asp Tyr
1               5                   10                  15

<210> SEQ ID NO 109
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 109

Arg Thr Phe Ser Ser Leu Ala Met Ala
1               5

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Ile Ser Arg Ser Gly Gly Ser Thr Asp Tyr Ala Asp Ser Val Lys
1               5                   10                  15
Gly

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Asp Tyr Ser Thr Leu Gln Tyr Tyr Asn Glu Tyr Glu Tyr Ser Asp
1               5                   10                  15

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Pro Thr Phe Ser Thr Tyr Ala Met Ala
1               5

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Ile Thr Gln Ser Gly Arg Thr Thr Tyr Tyr Glu Asp Ser Val Lys
1               5                   10                  15
Gly

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 114

Arg Asp Leu Trp Ser Asp Ser Pro Asp Asp Trp Arg Ile Tyr Ser Phe
1               5                   10                  15

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Thr Leu His Asn Phe Ala Met Ala
1               5

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Ile Ser Lys Gly Gly Gly Ser Ala Asp Tyr Ala Asp Ser Val Lys
1               5                   10                  15

Gly

<210> SEQ ID NO 117
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asn Asp Leu Ala Ser Tyr Ser Asp Ser Ser Tyr Thr Ser Thr Ser Arg
1               5                   10                  15

Tyr Asp Tyr

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Thr Phe Ser Ser Tyr Ala Met Ala
1               5

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Ile Ser Ile Leu Gly Gly Ser Ala Asp Tyr Glu Asp Ser Val Gln
1               5                   10                  15
```

Gly

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Arg Pro Ala Pro Ser Asp Ser Tyr Trp Ser Ser Thr Ser Tyr Ala
1               5                   10                  15

Tyr

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Thr Phe Ser Ser Leu Ala Met Ala
1               5

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Thr Thr Ile Leu Gly Gly Ser Ala Asp Tyr Gly Asp Pro Val Lys
1               5                   10                  15

Gly

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Arg Pro Ala Pro Ser Asp Asn Tyr Trp Ser Pro Ala Ser Tyr Ala
1               5                   10                  15

Tyr

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Thr Phe Ser Ser Tyr Ala Met Ala
1               5

```
<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ile Thr Val Ser Gly Ala Ser Thr Tyr Tyr Ala Asp Ser Val Lys
1               5                   10                  15

Gly

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Gly Pro Gly Thr Ile Phe Pro Asp Tyr Asp Tyr
1               5                   10

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Thr Phe Ser Gly Tyr Asn Met Gly
1               5

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Ile Asn Trp Ile Gly Gly Ala Thr Tyr Tyr Ala Asp Ser Val Lys
1               5                   10                  15

Gly

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Tyr Ser Glu Lys Phe Tyr Ser Gly Lys Asp Tyr Tyr Thr Arg Asp Tyr
1               5                   10                  15

Asp Tyr

<210> SEQ ID NO 130
<211> LENGTH: 363
<212> TYPE: DNA
```

<213> ORGANISM: Artificial Sequence
<220> FEATURE:
<223> OTHER INFORMATION: Description of Artificial Sequence: Synthetic
    polynucleotide

<400> SEQUENCE: 130

```
caggtgcagc tggtggagag cggaggcgga ctggtacaag cagggggttc tctcaggctg      60
agctgtgcgg cttccgggag gactttcacc tcttatgcta tgaattggtt ccgccaggcc     120
cctgggaagg aaagggagtt tgtggcagcc atctcttggt ccagcggcaa tacctacgtg     180
gccgactccg tcaagggtag gttcgccatc agccgggaca agctaagaa tactatgtac      240
ttgcagatga acagcctcgc gccggaagat actgcggtgt attactgcgc cgctactacc     300
atcgccacga tgtccgacga gtatacatat tggggacagg gaactcaggt tacagtatcc     360
tcc                                                                   363
```

<210> SEQ ID NO 131
<211> LENGTH: 363
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 131

```
caggtccagc tggtcgaatc cggtggcggg ttggtacagg cgggtggctc cctgcgcctg      60
agctgcgccg cgagtgggcg tacattttct aactacagaa tgggctggtt caggcaggct     120
ccgggaaagg agcgtgagtt cgtggctgcc atttcacgcg gaggtggcac cacactgtac     180
gccgactctg tcaaaggccg cttcaccatc tctcgcgaca acgctaagaa tactgttgat     240
ctccagatga accgcctgaa gccggaagac accgcagttt acttttgtgc cgcaggcgat     300
ttctctacca cttgggacga gtataactac tgggggcagg gaacacaagt gaccgtgtcc     360
agt                                                                   363
```

<210> SEQ ID NO 132
<211> LENGTH: 372
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 132

```
caggttcaac tggtggagag cggtgggggc ctggtgcagg caggcgggag cttgcggctt      60
tcatgtgttg catctggccg caccttctca agctatgcga tgggctggtt ccgtcagact     120
ccggggaaag agagggagtt cgtgagcgcg atttctcgcg gtggaggcag caccgactat     180
gccgattccg tgaagggcag gtttacgatc tccagagata cgccaagaa cacagtttat      240
ttgcagatga ataacctgaa atccgaggac accgcagtgt attactgcgc cctgcgggcc     300
tattcaggcc gctattacca gttcctggag tacgattact ggggccaggg cacacaggtg     360
actgtgtcct cc                                                         372
```

<210> SEQ ID NO 133
<211> LENGTH: 372
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 133

```
gaggttcagt tggtggagtc tgggggcggt ctggtccagg ctggtggatc attgcgcctg      60
agctgtaccg tttcaggcag gactttttct agctacgccg tagcttggtt ccgccaggca     120
cctggcaacg tccgggagct ggcggctgcc ctgagtcgcg ggggaggctc tgcttactat     180
acagacagtg tcaagggtcg cttcactatt agccgcgaca atgcgaaaaa caccgtctac     240
cttcagatga acagtctgaa gcccgaagac actgcggtgt attactgcgc ggccaggaac     300
tacgacggca cctattacca ggaaaaccaa tacaattact gggggcaggg aacccaggtg     360
accgtcagca gc                                                         372
```

<210> SEQ ID NO 134
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
caggtccagc tggtggaatc aggcggaggc ttggtgcagg ccggggggcag tctgttgctg      60
tcttgcgccg cgagcggacg cacattctcc acctacgcta tggggtggtt ccgccaggca     120
cctggaaaag aacgcatgtt tgtcgcggcc atctccgtta acgaggcag tacctactat      180
gcagattctg ttacgggccg tttcaccatt agccgcgaca atgcgaaaaa caccatgtat     240
ttgcaaatga ataacctgaa gcctggtgac acagccgtgt attactgcgc agcgcgtcgc     300
ccctaccccg gttccgactt tctcacatgg gcctcctacg attacagggg ccagggcacc     360
ctggtgaccg tgtctagt                                                   378
```

<210> SEQ ID NO 135
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135

```
caggttcagc tggtcgaatc tggcggtgga ctggtgcaag ctggtgggtt cctgcgcctc      60
agctgtgccg ctagtggccg tacctttagc tatacaacca tcggctggtt ccgccaggct     120
ccagggaagg aacgcgagtt cgtcgccgtg atctcagcag gaggcggttc ccgcgattac     180
gcggacgccc tcaaaggacg ctttacaatc tctcgcgata cgctaaaaa gatggtttat      240
ttgcaaatga ataacttgaa gcccgaggat accgccgtgt attactgcgc cgtgaggcgg     300
aatactgaca catataccac aaccggcgac tacgactact ggggtcaggg cacccaggtt     360
accgtttcat cc                                                         372
```

<210> SEQ ID NO 136
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
caagttcagc ttgtagagtc tggcgggggc ctggtgcaac ccggtgactc actgaggctg      60
```

```
tcttgtgtgg cctccggggg tacaatttcc tcactggcta tgggttggtt caggcaggct    120
ccgggtaagg agagggagtt tgtcgcagcc atcagctggt ctggccgctc aacatattac    180
gtggatagcg tgaaaggccg cttcactatt tctactgata cgcgaagaa taccgtgtat     240 ctccaaatga actccctgaa accgaggac acagcgtgt actattgcgt cgcaggcgag      300
gatggacaca gcgagtatga ctattggggc caaggcaccc aggtcacagt gtcctca       357
```

<210> SEQ ID NO 137
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

```
caggtgcagc ttgtggagag cggaggcggg ctggtgcagg ccgggggtag cttgcgcctc    60
agctgtgctg cctctggacg ctcatttgcc aactacgcaa tgggctggtt ccgtcaggct    120
cctgggaaag agcgcgagac cgtggcggcc atcagtcgcg ggggaggcag cacgtggtac    180
gcggactcag tcaaggggag gtttactatt tccaaggata cgctaagaa caccgtgtat     240 ctgcaaatga acagcctcaa gcccgaggac acagcaatct actattgcgc ggcccgcagt    300
tactccggct cctacactta ttccttcggc gagtacgact actggggtca gggcacccaa    360
gttaccgtgt cctcc                                                    375
```

<210> SEQ ID NO 138
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

```
caggtgcagc tggttgagtc tggaggcggt cttgtccagg ctggtggctc cttgcgcctg    60
agctgtgccg cttccgggag agctttctcc acatacgctc tcggctggtt caggcaggcc    120
cccggaaagg agcgcgagtt catcgctgca atcagccggg gcggtggcag cactgattat    180
gcagattctg tgaagggacg cttcaccatc tctcgtgata cgccaagtc taccgtatat    240 ttgcagatga atagtctgaa gcccgaagac accgctgtgt attactgtgc agcgcgtagc    300
tactcctcta gttactatta ctctcagtac gagtacgact actggggaca gggtactcag    360
gtgactgtgt ccagc                                                    375
```

<210> SEQ ID NO 139
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139

```
gaggtccagc tcgtggagag tggcggtggc ctcgtgcagg ccgggggctc cctgagactg    60
agttgtgccg cttctggccg caccttcagt tcagtcgcta tggcttggtt tcggcaggcc    120
cctggcaagg agcgcgagtt cgtgtccgct atcagttctg gaggcggttc cacggattac    180
gctgatagcg tgaagggcag attcactatc agcaaggaca acgctaagaa caccatgtat    240
```

```
ctccagatgg actctcttaa acccgaggat accgccgtgt attactgcgc cgctcgcgac      300
tattctagcc gtcgctatta ccagtcccgg tacgagtacg acctctgggg cctgggaacc      360
caagtcacag tctcctcc                                                    378
```

<210> SEQ ID NO 140
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140

```
caggtgcagt tggtggagtc cggtgggggc ctggtgcagc caggtggaag cctccgcctg       60
tcctgtgctg caagtggccg cacctttagg tcctactcaa tgggctggtt tcgtcaggct      120
ccaggaaagg aacgggagtt cgttgccgct atttcctggt attccgggac aacgtactat      180
gccgacccag tcaagggtag attcactatc agccgggacg atgcaaagaa cactctctac      240
ttgcagatga actccctgaa gcccgaggac accgccgtgt attactgcgc ggctaacgag      300
atcgccacaa tggaatcctc taacgattac tggggccagg gacccaggt taccgtctct      360 agc                                                                    363
```

<210> SEQ ID NO 141
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141

```
caggtgcagc tggtcgagag tggagggga ttggtccagc ctggtggctc tctgcgcctg        60
tcatgcactg cttcaggccg cccccgtaca acgtatgcaa tgggctggtt ccgtcaggct      120
cccggcaagg agcgcgagat cgtggcggct atttccaaag ccggaggctc tacctacgtg      180
gccgactctg cgaaaggccg ctttgccatc tctaaggaca cgccaagaa taccgtctat      240 ctgcaaatga acagcctcaa gcctgaggat accgcagttt attactgtgc agctcgcgca      300
ggcttcgctg cccaaatctt cgagtacgac tactggggac agggcaccct ggtgacagtg      360
tctagc                                                                 366
```

<210> SEQ ID NO 142
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142

```
gaggttcaac tggtcgagtc cgggggcggg ctcgtgcagg ccggaggttc catgcgcctg       60
tcctgtgcca attccggtag aacctttggg acctatgcta tggctggtt ccgccagtca      120 cccggcaaag agcgcgagcg ggtcgcgtcc atcgaccgtg acggttctat gtcctattac      180
gccgacagcg tgaaaggcag gttcacaatc agcggagaca atgcgaagaa caccgtgtat      240
ctccagatga actccctgaa acctgaggac accgccgtct attactgcgc ggcttcaaga      300
cgcgccgtta tttctctcca gacagttgat tactgggggcc agggaaccca ggtgactgtg      360
```

-continued tccagc                                                              366

<210> SEQ ID NO 143
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
gaagtgcagc tcgtggagtc tggtggccgt ttggtccaga ccggaggcag cttgaggctc      60
tcatgcgctg cctctggcag acatttttcc aattatgcaa tgggatggtt tcgtcaggct     120
cctggcaagg agagggagtt cgtggctgca atctcttggt acagcggcaa cacatactat     180
gccgactccg tgaaaggcag gtttaccatc agccgggata cgccaaaaa cactatgtat      240 ctccagatga actccctgaa gccagaggat acggcggtct attactgtgc agccaatcaa     300
atcgccacta tgattagcgt gggcgactac tggggccaag caccctggt gacagtgtca      360 tcc                                                                 363

<210> SEQ ID NO 144
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
caggtgcagt tggtcgagtc aggaggggc ctggtcgagg ccgggggctc cctgaggctc       60
gcttgcgctg cgagtggatc aatcttccgt ttgaacctga tgggatggta tagacaggct     120
cctggcaagc agcgtgaact ggtcgcacac gtgggtacta caggaaacac cgcctacgcc     180
gactctgtca aggggcgctt taccatctca aaggacgatg ctaagaacat ggtgtttctc     240
cagatgaact ccctcaagcc cgaggatact gccgtctatt actgctatgc ggaccgctgg     300
ggtcagttct cctggggcca gggaacacag gtaaccgttt cttca                    345

<210> SEQ ID NO 145
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
caggtgcagc tcgtggagtc tggcggtggc ctggtccagg ccggaggcag cctccggttg       60
agctgtgtag ctagtggccg tacctttacg ggctacgcga tgggctggtt cagacaagcg     120
cctggcaagg agagggagtt cgtcgccgtg attacttggt ccggggccac tacctattac     180
tccgcttccg tgaagggccg tttcacgctg agccgggata cgccaaaaa cacagtgtac      240 ctccagatga actccctgaa gtccgaggac actgccgttt attactgcgc cattcgcatc     300
cgggacggag tgtctcctga aaaccctaac gagtacggtt actggggcca gggcacccag     360
gtaaccgtgt cctca                                                    375

<210> SEQ ID NO 146
<211> LENGTH: 369

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
caggtccagc tcgtggagtc cggcggggc ttggttcagg ctgggggaag cctgcgtctg      60
tcatgcgtgg cgagcgggag accgtcggc tacggcatgg cttggtttag gcaggctcct     120
ggcaagcaac gcgatgttgt ggccgcgatc acttggtccg gcacttccac ctattacccc    180
gactcagtca aggggcgctt caccatctcc agagataacg ccaagaacac tatgtatctc    240
cagatgtcat ctctgaagcc agaagatacc gctgtatatt actgcgccgc tggctcccgt    300
cgccgggtgg gcgtggacgt gggtggatac gactactggg ccaaggcac tcaggtgacc    360 gtctccagc                                                            369

<210> SEQ ID NO 147
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147
caggtgcagc tcgtcgagag cggggcgga ctggtacagg ctggcgactc cttgcgtctg      60
agctgcgccg cgtccggcag gacgttcacc ttctcaactc acaatatggg ctggttccgt    120
caggcaccgg gtaaggagag agagttcgtc ggaggcatca tgtggaccag ccgggcaagt    180
tacgccgatt ctgtgaaggg tcgtttcacc gtaagccgtg ataacgcgaa gaacactgtc    240
tacttgcaga tgaactctct gaagcccgag gacactgcgg tttactattg cgctgccgca    300
tggtatggta acagcggagc ctcctacgac tactggggtc aaggaactca ggtcacggtc    360
agctcc                                                               366

<210> SEQ ID NO 148
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
caggtccaac tggtcgagtc tggcggaggc ctcgtgcaac ttgttcaagc cggggcagc     60 ctgcgccttt cttgtgctgc gagtggccgc accttttccg gtataacat gggttggttt    120 cgtcaggccc caggtaagga gcgcgagttc gtggctgcca ttgcttgggc aggcagcagg   180
acatattaca ccgatagcgt caaggggcgg tttactatct ctcgcgacaa tgcaaaaaac  240
actatgtacc tccagatgaa cacctgcgt cctgaggata cagccgtgta ttactgcgca    300
gcccatgacg agacctatta ccgccttgac cgggtggacc tctataccca ctggggccag   360
ggaacccagg tcactgtgtc ctcc                                           384

<210> SEQ ID NO 149
<211> LENGTH: 360
<212> TYPE: DNA
<213> ORGANISM: Artificial Sequence
<220> FEATURE:
<223> OTHER INFORMATION: Description of Artificial Sequence: Synthetic
```

-continued

```
      polynucleotide

<400> SEQUENCE: 149
caggtgcaac tggttgagtc cggggggcgga ctggtgcaac ctggcgagag tctgcgcctg      60
tcctgcgcgg cctccggtcc ttttactaga tatgcgatgg gttggttccg tcaagcgcct     120
gggaaggagc gtgagttcgt cgcggctatc agctggtcat ctggaaatac gtattacgtg     180
gattccgtga agggcaggtt cactatttcc agagacaacg ctaagaacac aatgtacttg     240
cagatgaaca gcctgaagcc agaggacaca gcggtttact attgtgctgc aaacgaggtc     300
gccaccatga gtggacccga tgactattgg ggacaaggta cacaagtcac tgtgtcctct     360

<210> SEQ ID NO 150
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
caggtgcagc tggtggagtc tggaggtggg ctggtgcagg cgggaggctc tctgcgtctg      60
tcttgtgctg ccagcggcgg ttcctttggc cggtacacaa tgggatggta tcgtcaagcg     120
cctggtaagg agcgcgagtt tgttgctgtg atctcatgga gcggcacaaa cacgtactat     180
gcggacagcg tgaagggtcg ctttaccatt tcccgtgata acgcgaagaa taccatgtac     240
ctgcaaatga acgatttgaa acccgaagat accgcagttt attactgtgc tgcgcgtgag     300
acttattact cacactggga cgaaaggatg gagtatgact attggggcca gggcacccag     360
gttacagtat cttcc                                                     375

<210> SEQ ID NO 151
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
caggtccagc tcgtagaaag cggaggtggc cttgtccaag ctggcgacag cctgcgcctt      60
tcctgcgttg ccagcggctc catcgactca tcctattacg tgtcttggtt ccgtcaggca     120
ccaggcaagg aacgtgatct ggtagctgcc atcaactggg gcgattctcg caccgcctat     180
gctgactccg ttaagggccg gttcacgatc tcccgtgata acgcgaaaaa tactgtgtat     240
ctccagatgc actccctgcg ccccaacgat accgcagtgt attactgtgc cagcagaatt     300
gggctgggcg ggccggtggt tgcggccccc acccgttatc cctattgggg ccagggcacc     360
ctggtaaccg tgtcttcc                                                  378

<210> SEQ ID NO 152
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
caagtgcaac tggtagagtc aggcggtggc cttgtgcagg ccggtggctc tctgcgcctg      60
```

```
tcttgcgctg cctctgagtc tatcttgcgg tttaacgtga tgtcatggtt gcgtcaggca    120
ccagggaaac agcgtgagct ggtggcagtc atcactagcg gtggcagcac gaattatgca    180
gactccgtga aaggccgctt cacgatctct cgtgacaacg ctaaaaacac cgtgtatctc    240
cagatgaaca gcctgaagcc agaagacact gccgtgtatt actgtgctgc cgacgagagc    300
gggcagtatt actggggaca gggcactcag gtgacagtca gcagc                    345

<210> SEQ ID NO 153
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
caggtccagc tcgtggagtc tgggggcggt ctcgtccagg ctgggggttc cctgcggctg    60
agctgtgccg cttctggctt gacgaccagt agcgccgctc tggcctggtt tcgtcaggct    120
cctggcaagg agcgtgagct tgatccaact attaccagcg gcggaggctc tacctactat    180
gccgacagcg ttaagggtcg gtttaccatc agcaaagaca cgctaagaa cactctttat    240 ctccagatgt caagcctcaa acctgaggac accgccgtct actattgcgc cgctcgcttt    300
tatagcacca cttactatta ccgcgaacac gagtatagtg actgggggca gggcacccaa    360
gtcacagtga gcagc                                                    375

<210> SEQ ID NO 154
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154
caggtgcaac tggtggaatc tgggggtggc ttggtgcagg ctggcgggtc tctgcgtctg    60
tcctgtgcgg cttcaggacg cactttcggc accagctttg gcagcctgag catgggctgg    120
ttcagacaag ccccccggcaa agagcgtgag ttcgtggctg ccatctctcg caacattggc    180
cgtacttatt acgcagattc cgtgaaagac aggtttacga tctctcgcga caacgctaag    240
aataccgcct ctcttcagat gaactctctg gagcccgaag acactgctgt ctataattgt    300
gccgcgacaa actcctacga tgaccttagg cgctcctacg cctacgacta ctggggacag    360
ggcacccagg tgacagtcag ctcc                                          384

<210> SEQ ID NO 155
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155
caggtccagc tggtggagag cggcggtggg ctggttcagg ctggaggctt cctgcgcctg    60
tcttgcgctg cctcaggtcg tacttttttcc tctttggcaa tggcttggtt ccgtcaagct    120
cccggcaagg agcgcgagtt cgtagccgct atctcccgct ctggaggctc taccgactac    180
gctgacagcg tcaagggacg cttcaccatc tctcgggaca cgccaagtc caccctgtac    240
```
ttgcagatgt ctagcctgaa acctgaggat acagcggtgt attactgcgc tgcacgtgac    300
tactctactc tccagtatta caatgagtat gaatactccg actggggcca aggcactctg    360
gtcactgtgt cctca                                                     375

<210> SEQ ID NO 156
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
caggtgcagc tcgtagagtc tggcggtggc ctggtccagg ctggggactc actgcgtctg     60
agttgtgccg cgtccggccc taccttcagt acgtatgcaa tggcctggtt cgccaagct    120 ccaggtaagg aacgcgagtt cgtggctgcc attacccaga gtggtcgcac cacttactat    180
gaagattctg tgaaggggcg gttcaccatt agcaaggata tgccaagaa cacccctctat   240 ctccagatga acagcctcca gcctgaagat acggcggtgt attactgcgc ggcccgcgac    300
ttgtggtctg attctcccga tgactggaga atttactctt tctggggaca ggggacccaa    360
gtaacagtca gttcc                                                    375

<210> SEQ ID NO 157
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
caggttcagc ttgtggagtc cggtggcggt ctggtccagg caggtggctc cctgcggctg     60
tcttgcgcag ccgctcgtcg cacactgcac aacttcgcaa tggcgtggtt cgccaggcc    120 cctggtaagg agagggagtt tgtggctgcc atttctaagg gaggcggttc cgccgactac    180
gccgatagcg ttaaggggcg ctttaccatt agtagggaca cgctaagaa cacagtgtac    240 ctccagatga acagcctcaa gccagaggat accgcagttt actattgcgc tgccaacgat    300
ctggcttctt atagcgacag ctcttacaca tccacaagcc gctacgacta ctggggtcag    360
ggcacccagg ttacagtgtc ctct                                          384

<210> SEQ ID NO 158
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158
caggtgcagc tcgtcgagtc tggcgggggga ctggtgcaga ctggtggctc cctgcgcctc     60
tcttgcgcgg cctctggccg caccttctca tcctatgcta tggcttggtt ccgtcaagcg    120
cccggtaaag agagggagtt tgtggccgct atctctatcc tcggtggcag cgctgactac    180
gaggattccg ttcagggacg cttcactatc tcaagagata cgccaagaa cactatgtac    240 cttcagatga actccctcaa gccagaggac accgctgtgt attactgtgc cgctcgcaga    300
ccggctccct ccgacagcta ctggagcagt acaagttacg catactgggg acaggggacc    360

```
ctggtgacag tgtccagt                                                    378
```

<210> SEQ ID NO 159
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159

```
gaggtacagc tggtcgaatc cggtggcggt ctggtgcagg ctggcggaag cctgcgcttg     60
agctgtgcgg cctctggccg cactttcagc tctcttgcaa tggcgtggtt ccgccaggcc    120
cctggaaagg agcgcgagtt cgtggccgcg accacaatcc tcggaggctc cgccgactac    180
ggcgacccgg tcaagggccg cttcacaatc tcccgcgata tgctaagaa cacggtgtat    240
ctccagatga actcactgaa gccagaggat accgccgttt attactgcac tgggagacgc    300
cccgctccat ccgacaacta ctggtcccct gccagctatg cttactgggg acaaggcacc    360
caagttaccg tgagcagt                                                    378
```

<210> SEQ ID NO 160
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160

```
caggtgcagt tggtggaaag cggcggtggc cttgtgcagg ctggcggttc actgcgcctc     60
agctgcgcac cttccggtcg caccttctcc tcttacgcga tggcgtggtt tcgccagcct    120
ccaggcaagg aacgggagtt tgtggctgcc attaccgttt ccggcgcaag tacctattac    180
gctgactctg ttaagggccg tttcaccatc tctcgcgata tgcgaaaaa ctctatgtac    240
cttcagatga actctttgaa accggaggat accgctgtgt actattgtgc agctggcggt    300
cccggaacca tcttcccaga ctatgattac tggggtcagg gtactcaggt caccgtctcc    360
tcc                                                                    363
```

<210> SEQ ID NO 161
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161

```
caagtacagc tcgtcgaatc cggcggtgga ctggtgcagg ccggagattc ccttaccctg     60
tcttgcaccg cttccggtcg cacctttca ggttacaata tggctggtt caggcaggcc    120
cctggtaagg agcgcgactt cgtcgctgcc atcaactgga tcggaggtgc tacctattac    180
gcggatagcg tgaaaggccg ctttaccatt agcagggata tgccaagaa cactgtctac    240
ctgcaaatga cagcctgaa gcccgaggat actgccgtgt attactgcca tcgctattcc    300
gagaagttct acagcgggaa ggactactat actcgtgact acgactactg gggtcagggt    360
acacaggtaa ctgtgtcctc a                                               381
```

<210> SEQ ID NO 162

<211> LENGTH: 220
<212> TYPE: PRT
<213> ORGANISM: Homo sapiens

<400> SEQUENCE: 162

```
Ser Gln Leu Pro Ala Pro Gln His Pro Lys Ile Arg Leu Tyr Asn Ala
1               5                   10                  15

Glu Gln Val Leu Ser Trp Glu Pro Val Ala Leu Ser Asn Ser Thr Arg
            20                  25                  30

Pro Val Val Tyr Gln Val Gln Phe Lys Tyr Thr Asp Ser Lys Trp Phe
        35                  40                  45

Thr Ala Asp Ile Met Ser Ile Gly Val Asn Cys Thr Gln Ile Thr Ala
50                  55                  60

Thr Glu Cys Asp Phe Thr Ala Ala Ser Pro Ser Ala Gly Phe Pro Met
65                  70                  75                  80

Asp Phe Asn Val Thr Leu Arg Leu Arg Ala Glu Leu Gly Ala Leu His
                85                  90                  95

Ser Ala Trp Val Thr Met Pro Trp Phe Gln His Tyr Arg Asn Val Thr
            100                 105                 110

Val Gly Pro Pro Glu Asn Ile Glu Val Thr Pro Gly Glu Gly Ser Leu
        115                 120                 125

Ile Ile Arg Phe Ser Ser Pro Phe Asp Ile Ala Asp Thr Ser Thr Ala
130                 135                 140

Phe Phe Cys Tyr Tyr Val His Tyr Trp Glu Lys Gly Gly Ile Gln Gln
145                 150                 155                 160

Val Lys Gly Pro Phe Arg Ser Asn Ser Ile Ser Leu Asp Asn Leu Lys
                165                 170                 175

Pro Ser Arg Val Tyr Cys Leu Gln Val Gln Ala Gln Leu Leu Trp Asn
            180                 185                 190

Lys Ser Asn Ile Phe Arg Val Gly His Leu Ser Asn Ile Ser Cys Tyr
        195                 200                 205

Glu Thr Met Ala Asp Ala Ser Thr Glu Leu Gln Gln
        210                 215                 220
```

<210> SEQ ID NO 163
<211> LENGTH: 332
<212> TYPE: PRT
<213> ORGANISM: Mus musculus

<400> SEQUENCE: 163

```
Met Arg Pro Leu Pro Leu Trp Leu Pro Ser Leu Leu Cys Gly Leu Leu
1               5                   10                  15

Gly Ala Ala Ala Ser Ser Pro Asp Ser Phe Ser Gln Leu Ala Ala Pro
            20                  25                  30

Leu Asn Pro Arg Leu His Leu Tyr Asn Asp Glu Gln Ile Leu Thr Trp
        35                  40                  45

Glu Pro Ser Pro Ser Ser Asn Asp Pro Arg Pro Val Val Tyr Gln Val
50                  55                  60

Glu Tyr Ser Phe Ile Asp Gly Ser Trp His Arg Leu Leu Glu Pro Asn
65                  70                  75                  80

Cys Thr Asp Ile Thr Glu Thr Lys Cys Asp Leu Thr Gly Gly Gly Arg
                85                  90                  95

Leu Lys Leu Phe Pro His Pro Phe Thr Val Phe Leu Arg Val Arg Ala
            100                 105                 110

Lys Arg Gly Asn Leu Thr Ser Lys Trp Val Gly Leu Glu Pro Phe Gln
        115                 120                 125
```

```
His Tyr Glu Asn Val Thr Val Gly Pro Pro Lys Asn Ile Ser Val Thr
            130                 135                 140

Pro Gly Lys Gly Ser Leu Val Ile His Phe Ser Pro Pro Phe Asp Val
145                 150                 155                 160

Phe His Gly Ala Thr Phe Gln Tyr Leu Val His Tyr Trp Glu Lys Ser
                165                 170                 175

Glu Thr Gln Gln Glu Gln Val Glu Gly Pro Phe Lys Ser Asn Ser Ile
            180                 185                 190

Val Leu Gly Asn Leu Lys Pro Tyr Arg Val Tyr Cys Leu Gln Thr Glu
        195                 200                 205

Ala Gln Leu Ile Leu Lys Asn Lys Lys Ile Arg Pro His Gly Leu Leu
    210                 215                 220

Ser Asn Val Ser Cys His Glu Thr Thr Ala Asn Ala Ser Ala Arg Leu
225                 230                 235                 240

Gln Gln Val Ile Leu Ile Pro Leu Gly Ile Phe Ala Leu Leu Leu Gly
                245                 250                 255

Leu Thr Gly Ala Cys Phe Thr Leu Phe Leu Lys Tyr Gln Ser Arg Val
            260                 265                 270

Lys Tyr Trp Phe Gln Ala Pro Pro Asn Ile Pro Glu Gln Ile Glu Glu
        275                 280                 285

Tyr Leu Lys Asp Pro Asp Gln Phe Ile Leu Glu Val Leu Asp Lys Asp
    290                 295                 300

Gly Ser Pro Lys Glu Asp Ser Trp Asp Ser Val Ser Ile Ile Ser Ser
305                 310                 315                 320

Pro Glu Lys Glu Arg Asp Asp Val Leu Gln Thr Pro
                325                 330

<210> SEQ ID NO 164
<211> LENGTH: 224
<212> TYPE: PRT
<213> ORGANISM: Mus musculus

<400> SEQUENCE: 164

Ala Ser Ser Pro Asp Ser Phe Ser Gln Leu Ala Ala Pro Leu Asn Pro
1               5                   10                  15

Arg Leu His Leu Tyr Asn Asp Glu Gln Ile Leu Thr Trp Glu Pro Ser
            20                  25                  30

Pro Ser Ser Asn Asp Pro Arg Pro Val Val Tyr Gln Val Glu Tyr Ser
        35                  40                  45

Phe Ile Asp Gly Ser Trp His Arg Leu Leu Glu Pro Asn Cys Thr Asp
    50                  55                  60

Ile Thr Glu Thr Lys Cys Asp Leu Thr Gly Gly Gly Arg Leu Lys Leu
65                  70                  75                  80

Phe Pro His Pro Phe Thr Val Phe Leu Arg Val Arg Ala Lys Arg Gly
                85                  90                  95

Asn Leu Thr Ser Lys Trp Val Gly Leu Glu Pro Phe Gln His Tyr Glu
            100                 105                 110

Asn Val Thr Val Gly Pro Pro Lys Asn Ile Ser Val Thr Pro Gly Lys
        115                 120                 125

Gly Ser Leu Val Ile His Phe Ser Pro Pro Phe Asp Val Phe His Gly
    130                 135                 140

Ala Thr Phe Gln Tyr Leu Val His Tyr Trp Glu Lys Ser Glu Thr Gln
145                 150                 155                 160

Gln Glu Gln Val Glu Gly Pro Phe Lys Ser Asn Ser Ile Val Leu Gly
```

```
            165                 170                 175
Asn Leu Lys Pro Tyr Arg Val Tyr Cys Leu Gln Thr Glu Ala Gln Leu
        180                 185                 190

Ile Leu Lys Asn Lys Lys Ile Arg Pro His Gly Leu Leu Ser Asn Val
    195                 200                 205

Ser Cys His Glu Thr Thr Ala Asn Ala Ser Ala Arg Leu Gln Gln Val
    210                 215                 220

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 165

His His His His His His
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 166

His His His His His His His His
1               5

<210> SEQ ID NO 167
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Gly
      Ser" repeating units

<400> SEQUENCE: 167

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 168
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Ser Gly" repeating units

<400> SEQUENCE: 168
```

```
Gly Gly Gly Ser Gly Gly Gly Ser Gly Gly Gly Ser Gly Gly
1               5                   10                  15

Gly Gly Ser Gly Gly Gly Ser Gly Gly Gly Ser Gly Gly
            20              25              30

Gly Ser Gly Gly Gly Ser Gly Gly Gly Ser Gly Gly Gly
        35              40              45

Ser Gly
    50

<210> SEQ ID NO 169
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Ser
      Gly" repeating units

<400> SEQUENCE: 169

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20              25              30

Gly Gly Ser Gly Gly Gly Ser Gly
        35              40

<210> SEQ ID NO 170
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(6)
<223> OTHER INFORMATION: This sequence may encompass 3-6 residues

<400> SEQUENCE: 170

His His His His His His
1               5
```